(12) United States Patent
Polak et al.

(10) Patent No.: US 11,582,856 B2
(45) Date of Patent: Feb. 14, 2023

(54) PLASMA APPLICATOR

(71) Applicant: COLDPLASMATECH GMBH, Greifswald (DE)

(72) Inventors: Martin Polak, Hinrichshagen (DE); Robert Banaschik, Greifswald (DE); Axel Kühle, Greifswald (DE); Tobias Güra, Eggesin (DE); Carsten Mahrenholz, Lubmin (DE)

(73) Assignee: COLDPLASMATECH GMBH, Greifswald (DE)

( * ) Notice: Subject to any disclaimer, the term of this patent is extended or adjusted under 35 U.S.C. 154(b) by 160 days.

(21) Appl. No.: 17/040,082

(22) PCT Filed: Mar. 22, 2019

(86) PCT No.: PCT/EP2019/057338
§ 371 (c)(1),
(2) Date: Sep. 22, 2020

(87) PCT Pub. No.: WO2019/180257
PCT Pub. Date: Sep. 26, 2019

(65) Prior Publication Data
US 2021/0022234 A1 Jan. 21, 2021

(30) Foreign Application Priority Data

Mar. 23, 2018 (DE) ...................... 10 2018 107 049.7
Sep. 10, 2018 (DE) ...................... 10 2018 121 978.4
Sep. 12, 2018 (DE) ...................... 10 2018 122 309.9

(51) Int. Cl.
*H05H 1/24* (2006.01)
*A61L 2/14* (2006.01)
(Continued)

(52) U.S. Cl.
CPC ............. *H05H 1/2406* (2013.01); *A61L 2/14* (2013.01); *A61L 2/26* (2013.01); *H05H 1/2437* (2021.05)

(58) Field of Classification Search
CPC ..... A61B 18/042; A61B 18/085; A61B 18/10; A61N 1/44; H05H 1/2406; H05H 2277/10
See application file for complete search history.

(56) References Cited

U.S. PATENT DOCUMENTS 6,565,558 B1 * 5/2003 Lindenmeier ............ H05H 1/46
607/40
10,357,580 B2 7/2019 Trutwig et al.
(Continued)

FOREIGN PATENT DOCUMENTS

CN 102316905 A 1/2012
CN 102711909 A 10/2012
(Continued)

OTHER PUBLICATIONS

Author: Lim Youboung, Title: Plasma Sterilization Film, Sterilization Packaging Container and Power Supply Device Applied to Same, p. 1-36, Publisher: WO2016182384A1, Date: Nov. 17, 2016 (Year: 2016).*
(Continued)

Primary Examiner — Wei (Victor) Y Chan
(74) Attorney, Agent, or Firm — Ware, Fressola, Maguire & Barber LLP

(57) ABSTRACT

An electrotechnical core for generating a cold atmospheric pressure or low-pressure plasma for the treatment of human, animal, or technical surfaces. The core has a side facing the surface and a side facing away from the surface and comprises the following layers, starting from the side facing the surface:
a first insulation layer,
a first electrode structure with a first contact between the first electrode structure and a power supply unit,
a second insulation layer to galvanically isolate the first electrode structure and a second electrode structure from one another,
wherein the second electrode structure is driven during operation by a voltage signal sufficient to ignite a plasma,
a third insulation layer to galvanically isolate the second electrode structure from a third electrode structure,
(Continued)

wherein the third electrode structure grounds the third electrode structure during operation.

14 Claims, 38 Drawing Sheets

(51) Int. Cl.
    *A61L 2/26*        (2006.01)
    *A61B 18/10*     (2006.01)

(56) References Cited

U.S. PATENT DOCUMENTS

| | | | |
|---|---|---|---|
| 2007/0043301 A1* | 2/2007 | Martinsen | A61B 5/0531 600/547 |
| 2009/0196800 A1 | 8/2009 | Imanishi et al. | |
| 2012/0046597 A1 | 2/2012 | Morfill et al. | |
| 2012/0271225 A1 | 10/2012 | Stieber et al. | |
| 2013/0345620 A1 | 12/2013 | Zemel et al. | |
| 2014/0217882 A1 | 8/2014 | Yagi et al. | |
| 2016/0045246 A1 | 2/2016 | Stieber et al. | |
| 2016/0331989 A1* | 11/2016 | Cho | A61N 1/326 |
| 2017/0136252 A1 | 5/2017 | Weltmann et al. | |
| 2017/0231680 A1 | 8/2017 | Mahrenholz et al. | |
| 2019/0308027 A1 | 10/2019 | Hahnl et al. | |
| 2019/0327823 A1 | 10/2019 | Hahnl et al. | |

FOREIGN PATENT DOCUMENTS

| | | |
|---|---|---|
| CN | 107535042 A | 1/2018 |
| DE | 102014013716 A1 | 3/2016 |
| DE | 102015101391 A1 | 8/2016 |
| DE | 102016108450 A1 | 11/2017 |
| DE | 102017100161 A1 | 7/2018 |
| EP | 2323600 A1 | 5/2011 |
| EP | 3171676 A1 | 5/2017 |
| GB | 2551890 A | 1/2018 |
| WO | 2010/094304 A1 | 8/2010 |
| WO | 2014/040630 A1 | 3/2014 |
| WO | 2016/055654 A1 | 4/2016 |
| WO | 2016/182384 A1 | 11/2016 |

OTHER PUBLICATIONS

Author: Lim Youboung, Title: Plasma Sterilization Film, Sterilization Packaging Container and Power Supply Device Applied to Same, p. 1-36, Publisher: WO2016182384A1 (Translation), Date: Nov. 17, 2016 (Year: 2016).*

Author: Mahrenholz Carten, Title: Device for Generating a Cold Atmospheric Pressure Plasma, p. 1-33, Publisher: WO2016055654 (Translation) Date: Apr. 14, 2016 (Year: 2016).*

Author: Mahrenholz Carten, Title: Device for Generating a Cold Atmospheric Pressure Plasma, p. 1-33, Publisher: WO2016055654 (Original) Date: Apr. 14, 2016 (Year: 2016).*

Author: Hee-Soo, Jung, Title: Plasma Generating Apparatus, Publisher: GB2551890A, p. 1-28, Date: Nov. 5, 2016 (Year: 2016).*

Search Report and Written Opinion dated Jan. 25, 2022 issued by the IPOS in corresponding SG Application No. 11202009277P, 12 pages.

Office Action dated Jul. 19, 2021 issued by the Eurasian Patent Office in corresponding EA Application No. 564972EA, together with machine translation, 4 pages.

Third Party Observations filed with the European Patent Office on Sep. 25, 2020 in corresponding Application No. EP 19713755.7, 7 pages.

Search Report dated Sep. 13, 2019 issued by the German Patent Office in corresponding Application No. DE 10 2018 122 309.9, 8 pages.

PCT International Search Report and Written Opinion dated Jun. 28, 2019 issued by the European Patent Office in corresponding Application No. PCT/EP2019/057338, 21 pages.

Chinese Office Action issued in corresponding Chinese patent application No. 201980033357.0 dated Aug. 18, 2022; 11 pages.

\* cited by examiner

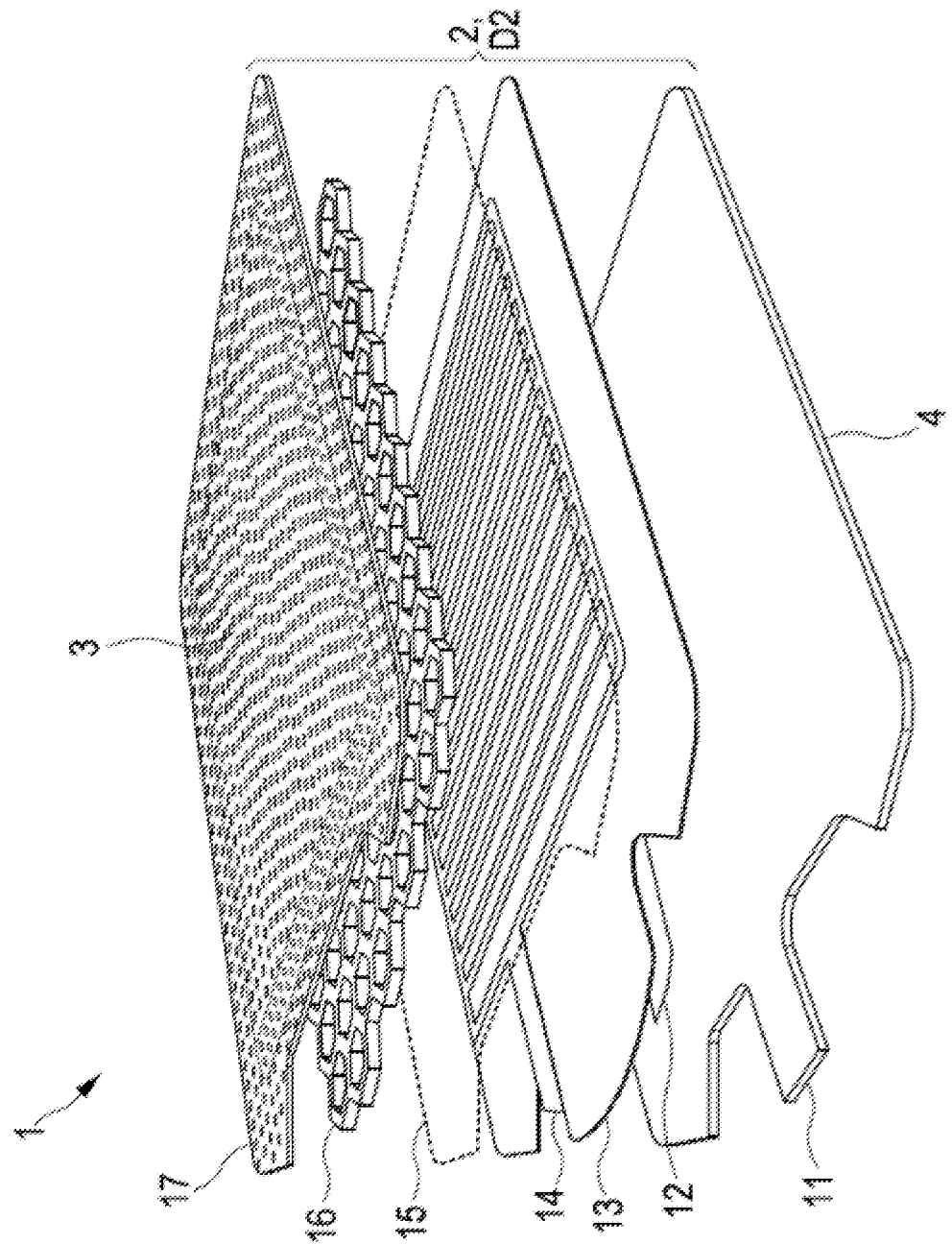

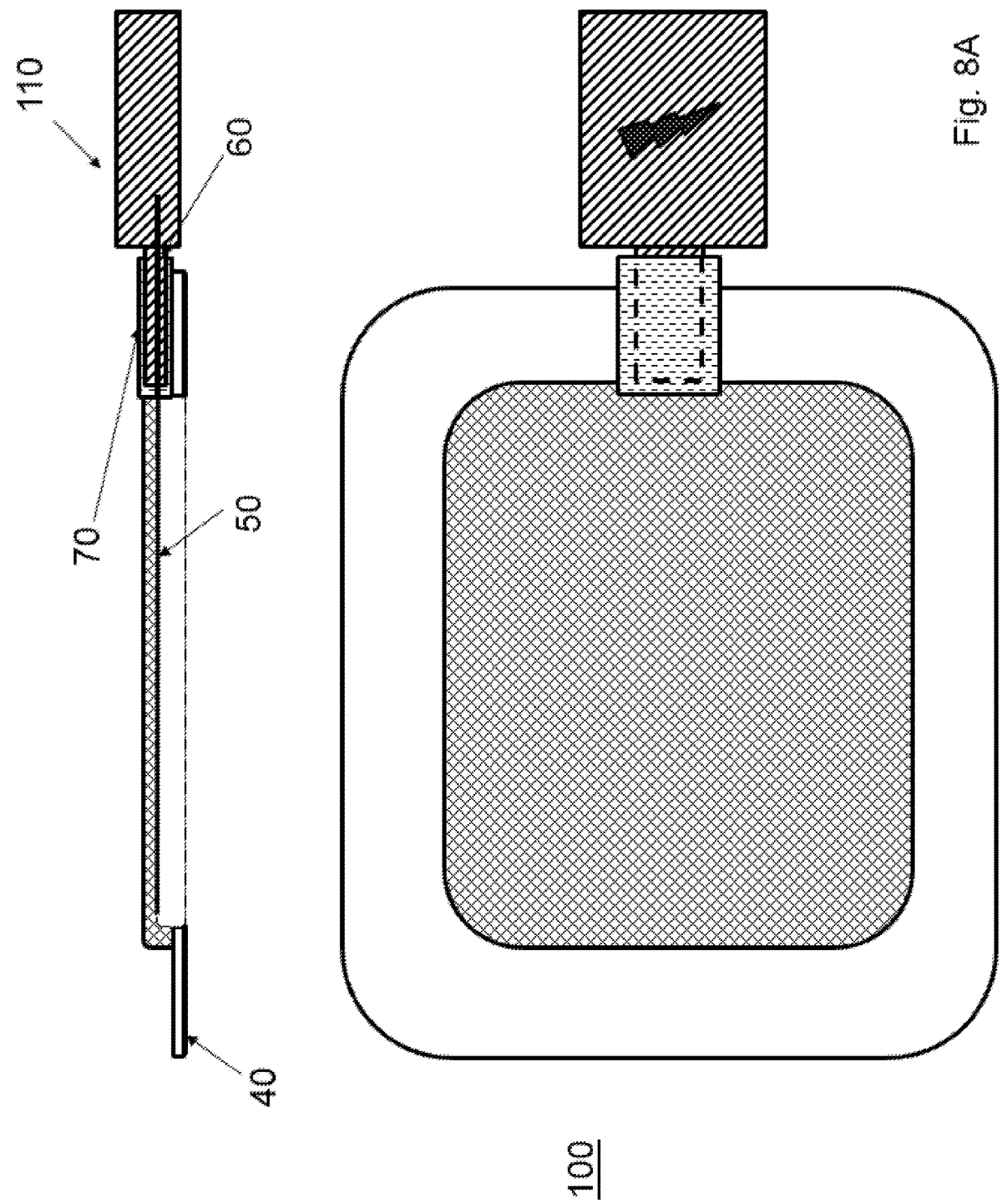

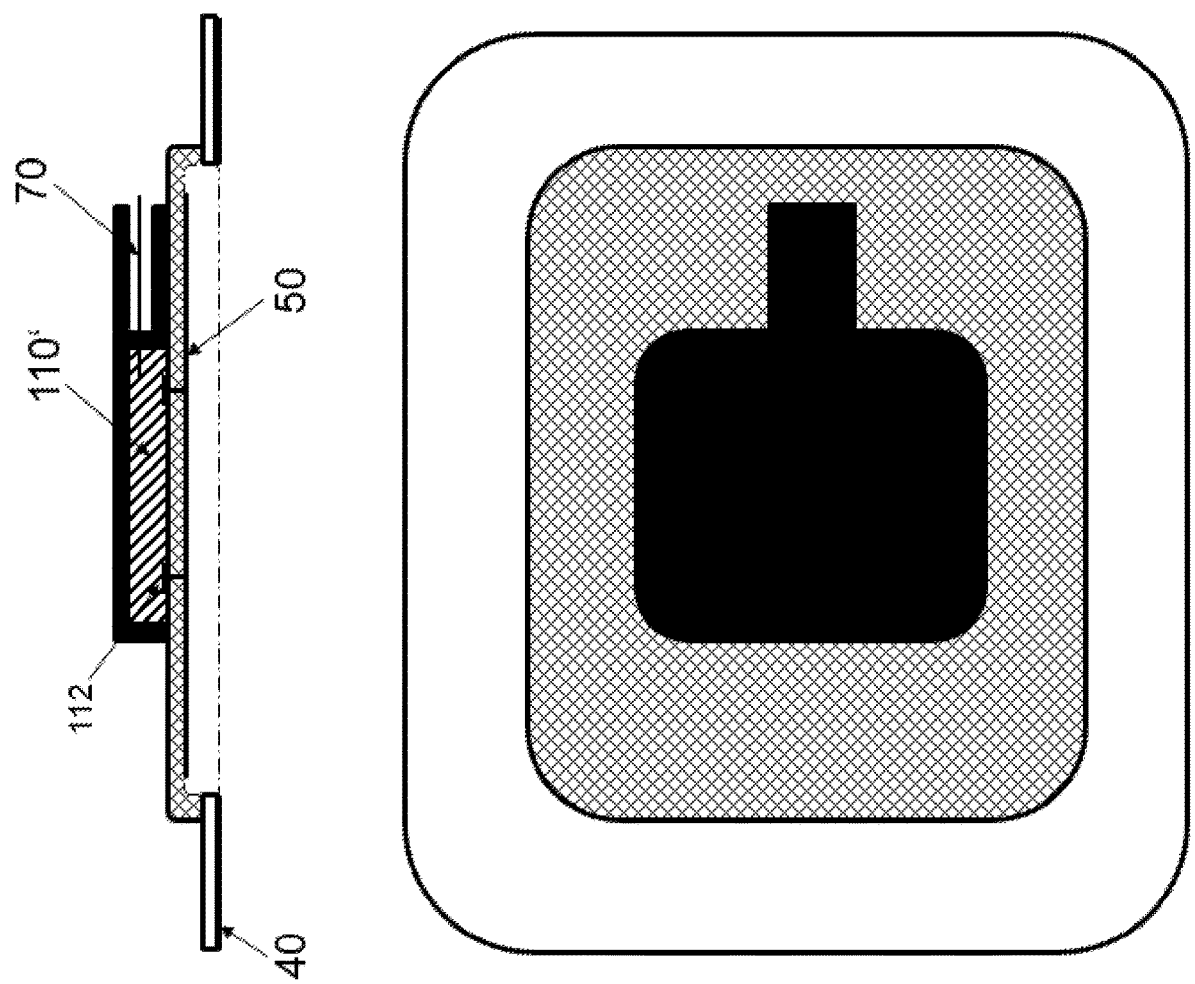

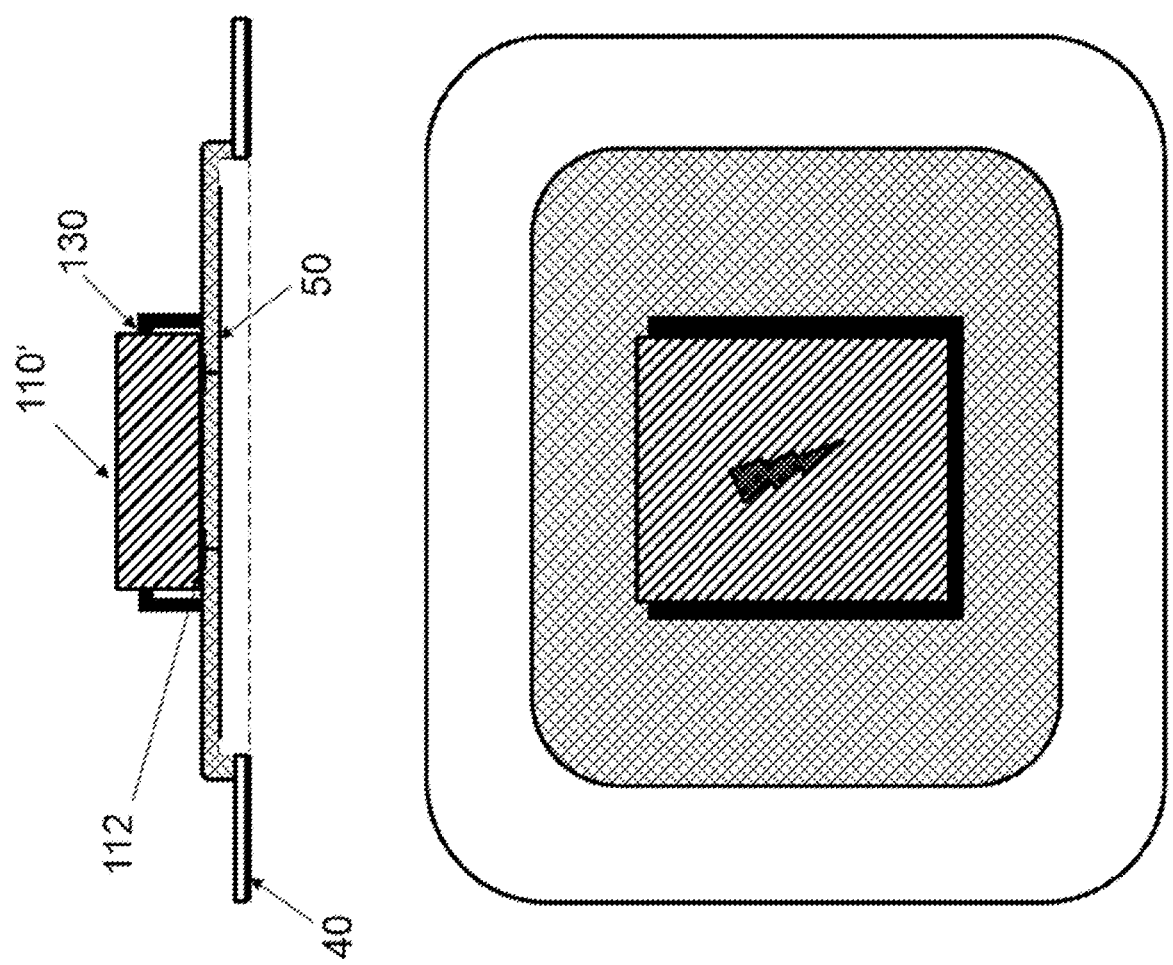

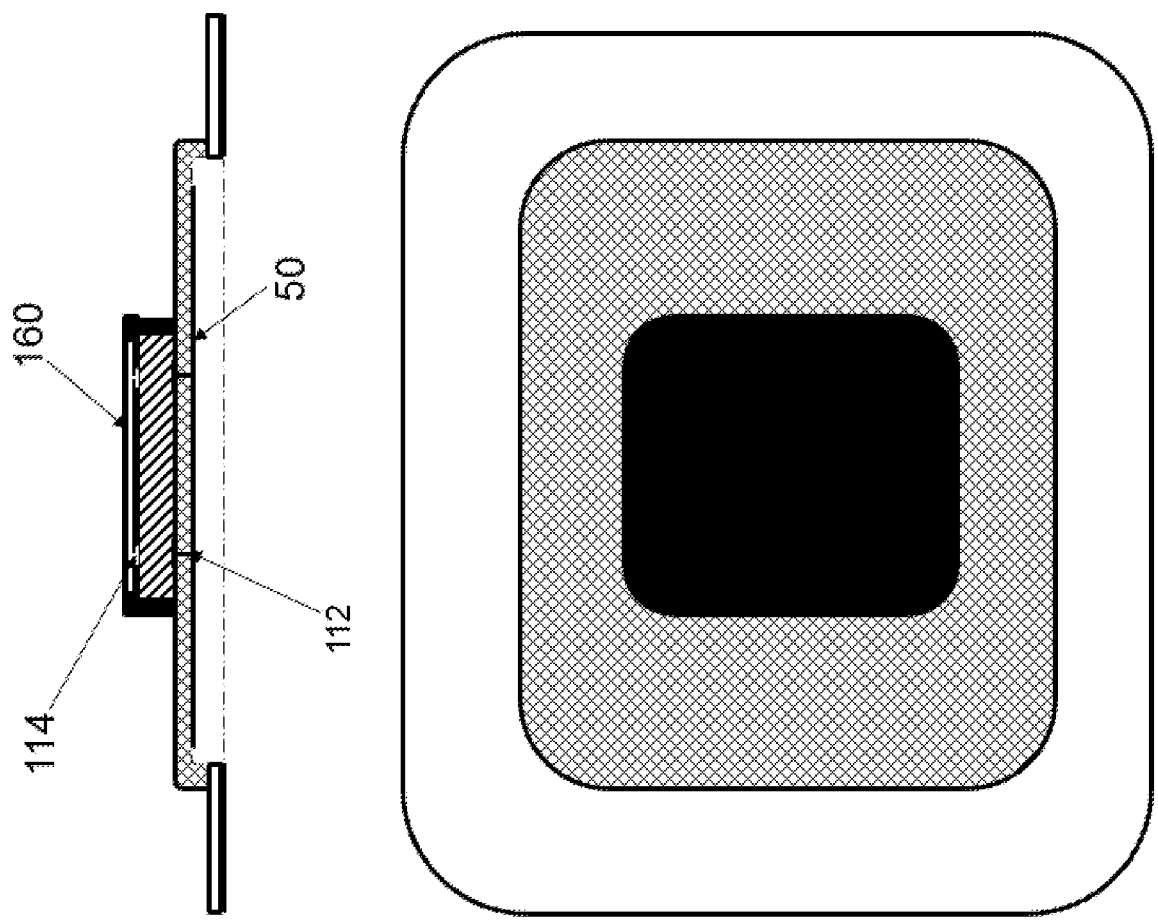

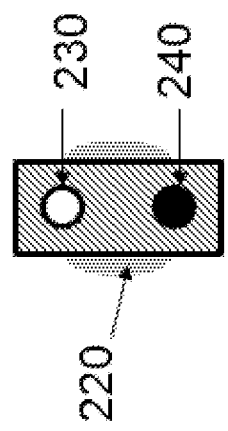
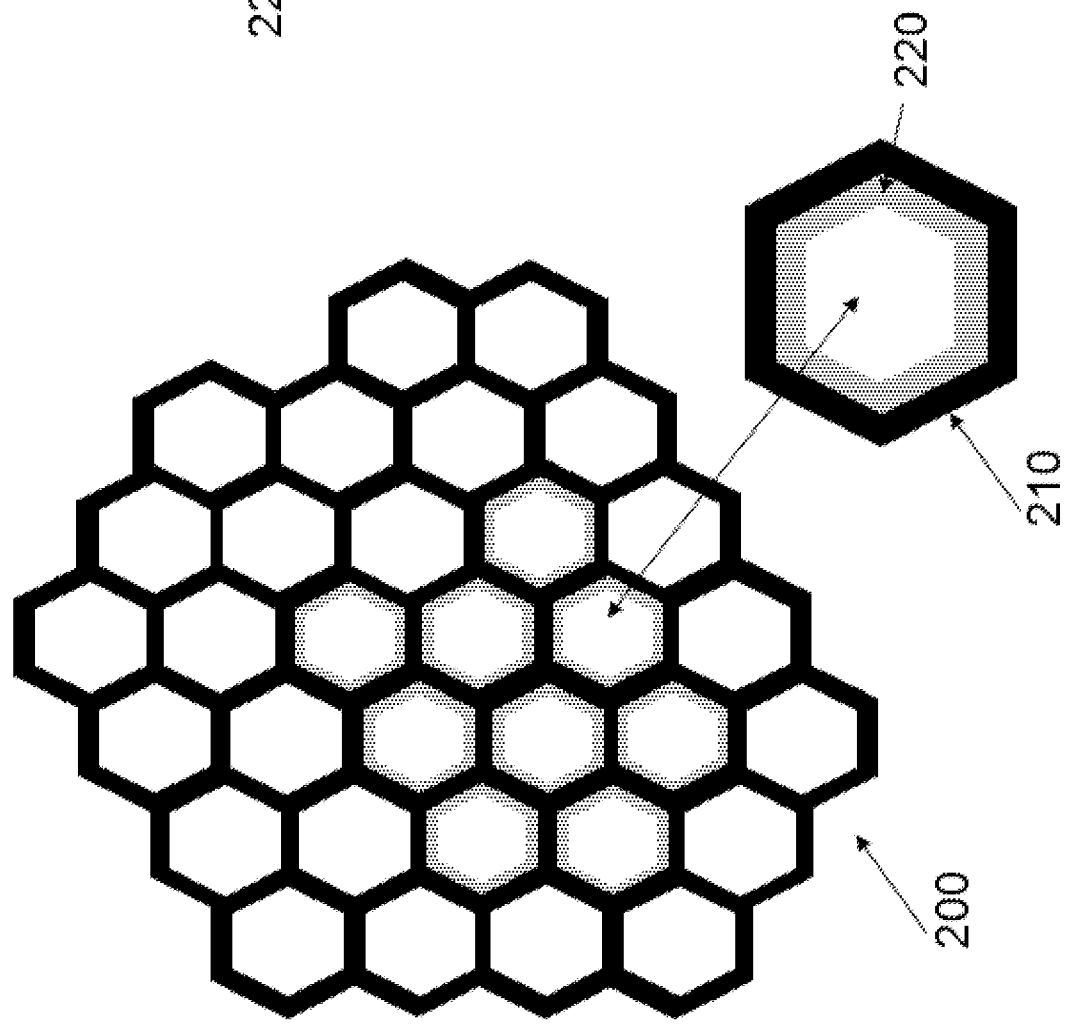

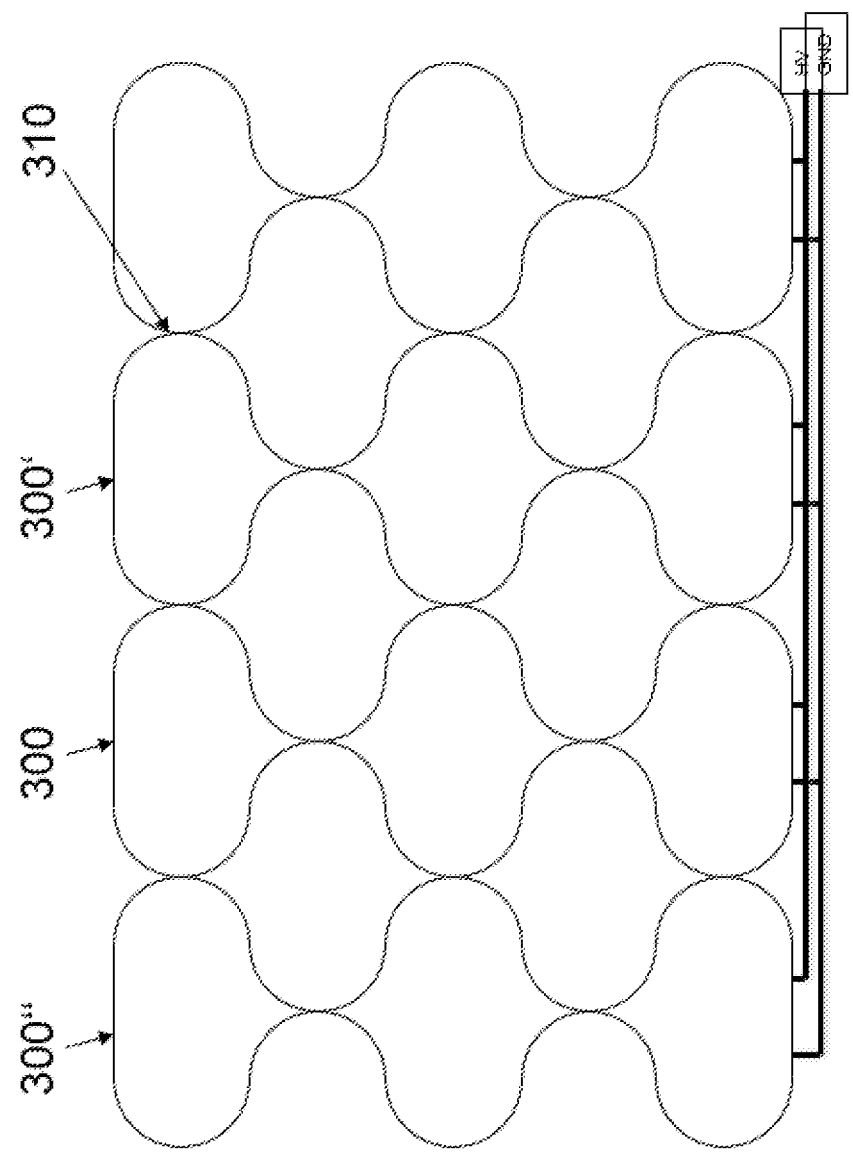

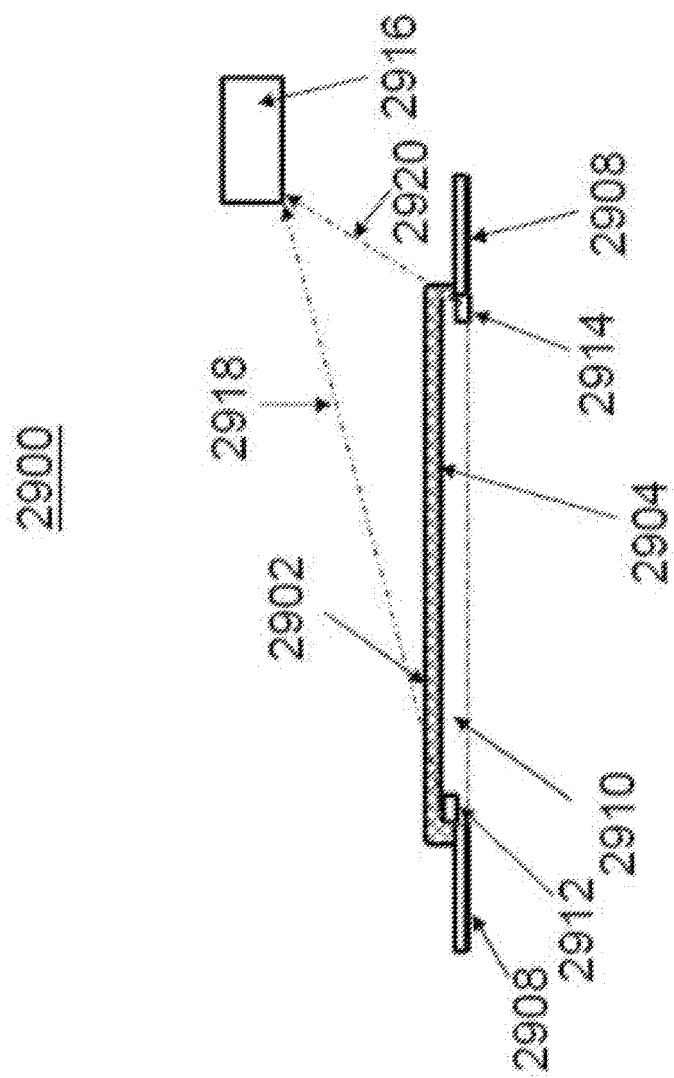

PLASMA APPLICATOR

CROSS REFERENCE TO RELATED APPLICATIONS

This application is the U.S. National Stage of PCT/EP2019/057338 filed on Mar. 22, 2019, which application claims priority under 35 USC § 119 to German Patent Application No. 102018107049.7 filed on Mar. 23, 2018, German Patent Application No. 102018121978.4 filed on Sep. 10, 2018 and German Patent Application No. 102018122309.9 filed on Sep. 12, 2018. All of these applications are hereby incorporated by reference in their entirety.

TECHNICAL FIELD

The invention relates to a plasma applicator for generating a cold plasma for the treatment of human or animal or technical surfaces. The invention furthermore relates to an electrotechnical core for a plasma applicator.

BACKGROUND OF THE INVENTION

For operation, a plasma applicator is typically connected via a cable to a power supply unit, e.g., a high-voltage generator, which provides a voltage signal that is sufficient to ignite a physical plasma. The power supply unit can comprise a controller which controls current, voltage or treatment time, for example.

The plasma applicator typically comprises an electrotechnical core. An electrotechnical core comprises a multi-layer system which, in the layer thickness direction, comprises the following layers in succession: a first insulation layer, a first electrode structure, a second insulation layer, in particular a dielectric layer, a second electrode structure. When a plasma applicator with such an electrotechnical core is placed on a surface to be treated, the first insulation layer, as the lowermost layer, is assigned to a surface to be treated. Typically, the second electrode structure is typically actively driven by a voltage signal and often embodied as a surface electrode. As a rule, the first electrode structure forms a counter electrode and is at ground potential.

A voltage, which may be modulated and typically is modulated, is applied during operation between the second electrode structure and a counter electrode, which may also be formed by a surface to be treated.

The potential of the counter electrode can be a ground potential or a potential deviating therefrom. Here, the voltage signal refers to the voltage applied, which may be modulated in sinusoidal, triangular or rectangular fashion, for example. Furthermore, the voltage signal can also be composed of individual pulses.

For reasons of simplicity, this description refers again and again to a "driven" electrode structure. The voltage—i.e., the voltage signal—is always applied between the driven electrode structure and the counter electrode. Since the counter electrode typically—but not necessarily—is at ground potential, the simplified expression "the voltage signal is applied to the driven electrode structure" is used to describe that the applied voltage acts between driven electrode structure and counter electrode.

As a rule, an electrotechnical core comprises a ground connector, which is electrically conductively connected to the first electrode structure, and a high-voltage connector, which is electrically conductively connected to the second electrode structure. The first and second electrode structure are typically connected to a power supply unit via a cable at the ground connector and the high-voltage connector, said power supply unit, during operation, providing a voltage signal that is sufficient to ignite a plasma and transmitted to the second electrode structure.

The second insulation layer is typically arranged between the first and the second electrode structure and electrically insulates the first and second electrode structure from one another. Consequently, the second insulation layer prevents a short circuit between the first and second electrode structure by way of galvanic isolation. By means of a voltage applied to the second electrode structure in the form of a voltage signal, a supplied gas or gas mixture, such as air, is ionized and converted into a reactive state in the sealed gas space formed between the plasma applicator and the surface to be treated. Thus, a physical plasma is generated. The plasma distributes uniformly in the sealed gas space and interacts with the surface to be treated.

Electrotechnical cores only comprising the second electrode structure and the second insulation layer are also known. Then, the second insulation layer is situated during operation on the side facing the surface to be treated. The first electrode structure, in particular, is not provided in such electrotechnical cores; instead, the function of the ground electrode is realized during operation by the human or animal body or the surface to be treated itself. By way of example, such an electrotechnical core is described in DE 10 2017 100 161 A1. In this case, the surface to be treated forms a counter electrode.

In addition to the three states of matter of solid, liquid and gas, plasma is referred to as the fourth state of matter. If sufficient amounts of energy, for example in the form of electrical energy, are supplied to a gas or gas mixture, some of the atoms in the gas are ionized, i.e., electrons are removed from the atomic shell and move as free particles, leaving the positively charged atom. If a gas consists of a sufficiently high proportion of free ions and electrons, the state of matter is referred to as physical plasma. Thus, physical plasma is matter, some of whose constituents are charged components, ions and electrons, which move as free charge carriers.

Collision processes cause some atoms of the ionized gas or gas mixture to be converted into an excitable state. Upon de-excitation, these atoms emit their energy in the form of electromagnetic radiation, the spectrum of which extends from the UV range via the visible spectral range up to the IR range. Additionally, the excited atoms and the ions can interact chemically and bind to form new molecules.

For the purposes of generating a plasma, plasma jets, torches, corona discharges and the dielectric barrier discharge (DBD) are known. In the case of dielectric barrier discharges (DBD), plasmas are typically generated at atmospheric pressure, far from thermal equilibrium. An applied AC voltage leads to the formation of tiny discharge channels with each period. Since the discharge channels only make up a fraction of the entire discharge volume and the time duration of the discharge is severely constrained by the capacitive coupling, the mean gas temperature in the discharge remains close to room temperature. Consequently, a cold plasma at atmospheric pressure or low pressure can be generated by way of the dielectric barrier discharge (DBD). Atmospheric pressure plasma refers to the special case of a physical plasma where the gas pressure in the plasma approximately corresponds to that of the surrounding atmosphere—so-called normal pressure. If the gas pressure in the plasma is lower than atmospheric pressure then this is referred to as a low-pressure plasma. Cold plasma, with a temperature below 40° C., is currently investigated for applications in plasma medicine and has already found its first applications.

The principal goal of plasma medicine lies in therapeutic use of plasma; i.e., physical plasma should be applied directly to the human or animal body. The primary targets here are plasma-assisted modification of bio-relevant surfaces, a plasma-based bio-decontamination/sterilization and a direct therapeutic use for promoting wound healing.

Possible applications lie, firstly, in the area of antimicrobial effects and, secondly, in the targeted and controllable modification of mammalian cells and tissue. Medical plasma applications are discussed, in particular, in the context of the support of healing processes, with a particular focus on the treatment of chronic wounds, the treatment of infectious skin diseases and the treatment of inflammatory skin diseases (dermatitis).

According to the current state of research, the principal active components of cold plasmas are reactive nitrogen and oxygen species, UV radiation, charged particles and electric fields. Reactive nitrogen and oxygen species are formed short-term and locally by coupling electrical energy into gases that are not biologically effective per se (argon, helium, nitrogen, oxygen, air and mixtures thereof) and by way of subsequent interaction with adjacent media (atmospheric air, liquids, surfaces). Electric fields and signals caused thereby play an important role in regulating body-inherent healing processes. In the case of an injury, these signals are some of the first signals that the body receives about said injury. Thus, for example, the electrostimulation of wounds is a recognized treatment method which can reactivate and maintain body-inherent and physiological repair processes in a targeted fashion.

Here, planar plasma applications which allow human and/or animal surfaces, in particular wounds, to be treated completely and homogeneously using a cold atmospheric pressure plasma are of particular medical interest.

DE 10 2014 220 488 A1 describes an apparatus for generating a cold atmospheric pressure plasma for treating human and/or animal surfaces. The apparatus comprises a flexible, planar multi-layer system with a side facing the surface to be treated and a side facing away from the surface to be treated. The multi-layer system, which forms an electrotechnical core, comprises the following layers:

a first electrode layer on the averted side of the multilayer system, a second electrode layer on the facing side of the multilayer system, wherein the electrode layer has a multiplicity of cutouts or a grid-like or meandering embodiment, a dielectric layer, which is arranged between the first electrode layer and the second electrode layer, and a spacer layer, which is arranged adjacent to the second electrode layer on the facing side of the multi-layer system and which, during operation, ensures a distance between the surface to be treated and the second electrode layer arranged at the bottom.

The described apparatus should facilitate large-area wound treatment, in particular of wounds greater than 200 cm².

To generate the cold atmospheric pressure plasma, an apparatus as described in DE 10 2014 220 488 A1 is typically connected via a cable to a high-voltage generator in order to transfer a high voltage to the first electrode layer. Typically, the cable for transferring the high voltage can be connected to an electrode layer of an apparatus as described in DE 10 2014 220 488 A1 by means of a high-voltage-suitable plug-in apparatus.

DE 10 2015 101 391 B4 describes a plasma generating device, which comprises an electrode carrier and a first electrode and a second electrode. The first electrode is arranged on or in the electrode carrier. Furthermore, it comprises a high-voltage-suitable plug contact connection for electrically contacting at least one of the electrodes. The plug contact connection comprises a plug and a plug-in socket for receiving the plug. The plug-in socket is securely arranged on or in the electrode carrier and electrically conductively connected to one of the electrodes.

SUMMARY OF THE INVENTION

It is an object of the present invention to facilitate an improved plasma applicator.

According to a first aspect, the object is achieved by an electrotechnical core for generating a cold atmospheric pressure or low-pressure plasma for the treatment of human and/or animal and/or technical surfaces.

The electrotechnical core has a side facing the surface to be treated and a side facing away from the surface to be treated and comprises the following layers, arranged above one another, starting from the side facing the surface to be treated:

a first insulation layer,
a first electrode structure which is provided with a first contact for establishing electrical contact between the first electrode structure and a power supply unit and which is grounded during operation,
a second insulation layer, which is embodied to galvanically isolate the first electrode structure and a second electrode structure from one another,
a second electrode structure which is provided with a second contact for establishing electrical contact between the second electrode structure and a power supply unit and which is driven during operation by a voltage signal that is supplied by a power supply unit and that is sufficient to ignite a plasma,
a third insulation layer, which is embodied to galvanically isolate the second electrode structure and a third electrode structure from one another,
a third electrode structure which is provided with a third contact in order to ground the third electrode structure during operation.

The invention is based on the discovery that the vertical integration of a conventional plasma applicator can be reduced if an electrotechnical core is designed to be safe to touch per se. If an electrotechnical core itself already provides contact protection, it is possible to dispense with an enclosure that is safe to touch, which is complex in production, and it is possible to use an alternative enclosure which only comprises a single injection molded layer and itself does not guarantee contact protection.

The inventors have recognized that an electrotechnical core that is already safe to be touched on its own can be used as an independent module. That is to say, such an electrotechnical core can be inserted into various enclosures or can be arranged in the latter without any special requirements being placed on an enclosure in respect of contact protection.

The inventors have furthermore recognized that if an electrotechnical core comprises a third electrode structure, which fulfills the function of a ground electrode, on the side facing away from the surface to be treated, then contact protection and EMC shielding can be ensured particularly easily. The third insulation layer is then arranged between the second and the third electrode structure and electrically insulates the second and the third electrode structure from one another. Consequently, the third insulation layer prevents a short circuit between the second electrode structure, to which voltage is applied during operation, and the shielding third electrode structure by way of galvanic isolation.
Preferred Embodiments of the Electrotechnical Core According to the First Aspect The third electrode structure is preferably embodied so as to have a shielding effect. The third electrode structure is preferably embodied as a surface electrode without relatively large gaps. In contrast thereto, the first electrode structure preferably has a special geometry and is embodied in such a way that suitably high electric field strengths form at its electrode sections, preferably on the side facing away from the second electrode structure, so that a generated plasma is distributed as a surface plasma on the body-facing side of the first electrode structure. This can be achieved by virtue of the first electrode structure having correspondingly large gaps, which could be formed, for example, by appropriate distances between the electrode sections of the first electrode structure. The first electrode structure is that electrode structure which is situated closest to the surface to be treated during use. During operation, the plasma forms directly at the first electrode structure, i.e., between the body and the first electrode structure. This works if the first electrode structure has cutouts through which—if the "field line" concept is considered—field lines can emerge from the electrotechnical core.

The first insulation layer is preferably formed by a biocompatible material.

The second electrode structure can likewise have a specific geometry and, particularly in that case, be arranged with a defined overlap with the first electrode structure.

The electrotechnical core can have such a flexible embodiment that the latter, for the purposes of a plasma treatment, can be adapted in terms of its shape to a shape of a surface to be treated.

The electrotechnical core can also be rigidly embodied in a specified shape, which may already be, for example, particularly suitable for a plasma treatment of a certain body segment or a certain technical surface.

By way of example, the basic shape of the electrotechnical core could be angular, round, or any polygonal shape.

In one embodiment, the electrotechnical core comprises a plug-in apparatus, wherein the first and second contact of the first and second electrode structure, respectively, accordingly form a first and second conductor track of the plug-in apparatus. The conductor tracks preferably each protrude at the same longitudinal side of the electrotechnical core from the longitudinal side of the respective corresponding electrode structure. The plug-in apparatus preferably furthermore comprises a tab, which is connected accordingly to the second insulation layer. Preferably, the first and the second conductor track are galvanically isolated from one another by the tab.

In one embodiment, the electrotechnical core furthermore comprises a spacer structure which is arranged adjacent to the first insulation layer on the side of the electrotechnical core facing the surface to be treated such that the spacer structure is situated between a surface to be treated and the first insulation layer during a plasma treatment.

The spacer structure can be formed by a biocompatible material. By way of example, the spacer structure can have a honeycomb shape or an X, O, Z, M, E or W shape.

A contact or an electrode structure of the electrotechnical core can also have at least one feature that changes in such a way as a consequence of a first use that it is no longer possible to transmit a voltage signal sufficient to ignite a plasma to the second electrode structure. This can ensure single use of the electrotechnical core. By way of example, such a feature could be a taper of an electrode section of an electrode structure, which is destroyed shortly before the end of the first use by a high current pulse to be provided at that point. The aspect of single use is discussed in more detail below.

Further Aspects

Further aspects which can contribute to an improved plasma applicator, in each case on their own and independently of the other further aspects, are described below.

A further aspect relates to a feature which changes in such a way as a consequence of use that it is no longer possible to transmit a voltage signal sufficient to ignite a plasma to an electrotechnical core. This feature can be realized for different plasma applicators and, in particular, for different electrotechnical cores or plug-in apparatuses of a plasma applicator, in combination with the remaining aspects described herein, or else independently thereof.

This aspect, which itself can contribute to an improved plasma applicator, consists of a contact or an electrode structure having at least one feature that changes in such a way as a consequence of use that it is no longer possible to transmit a voltage signal sufficient to ignite a plasma to an electrotechnical core. A feature which changes in such a way as a consequence of use that it is no longer possible to transmit a voltage signal sufficient to ignite a plasma to an electrotechnical core serves to ensure that a plasma application is used only once.

This aspect can preferably be realized on an electrotechnical core of the type described here, in particular on an electrotechnical core as per the first aspect, but it could also be realized in other plasma applicators. In particular, another plasma applicator could comprise an electrotechnical core with only a second electrode structure and a second insulation layer such that a counter electrode is realized during the application by a surface to be treated. Another plasma applicator could also comprise an electrotechnical core with a first insulation layer, a first electrode structure, a second insulation layer, and a second electrode structure. The feature ensuring single use in an electrotechnical core is preferably realized as a constituent part of an electrode structure to which a voltage signal is applied during operation.

In one embodiment variant of this aspect, the feature is formed by a taper of a contact or of an electrode section of an electrode structure, which is destroyed shortly before the end of the first use by a high current pulse to be provided at that point.

As an alternative or in addition thereto, provision can be made of, for example, a memory, e.g., in the form of a memory chip, the content of which is altered upon first use and read before each application.

A plasma applicator having a feature ensuring single use can also comprise an electrotechnical core which is formed by a wire mesh, wire cloth or wire netting.

Optionally, a plasma applicator having a feature ensuring single use can comprise an enclosure and/or a distance structure and/or an access port for supplying and removing a fluid medium to and from a gas space, respectively. Optionally, a plasma applicator having a feature ensuring single use can also comprise an integrated power supply unit.

A plasma applicator having at least one feature serving to ensure the plasma applicator is only able to be used once can also comprise at least one sensor which is embodied, during operation, to capture and output measurement variables relevant to a plasma treatment and/or wound healing, in particular physiological and/or physical measurement variables of a body segment covered by the plasma applicator during use.

A further aspect which can contribute to an improved plasma applicator, on its own and independently of the remaining aspects described herein or in combination therewith, relates to an enclosure with a pocket, in which an electrotechnical core can be arranged in removable fashion. An enclosure with a pocket can be realized as a constituent part of different plasma applicators and can also be combined, inter alia, with the aspect relating to single use.

According to this aspect, the object is achieved by a plasma applicator with an electrotechnical core and an enclosure with a pocket. The pocket is preferably embodied in such a way that an electrotechnical core can be inserted into said pocket and then be at least partly enclosed by the enclosure. An electrotechnical core that can be inserted into the pocket is preferably embodied in accordance with at least one of the described embodiments of the first aspect. However, an electrotechnical core that can be inserted into the pocket can also be an electrotechnical core with a design deviating from that of the first aspect. By way of example, such an electrotechnical core could be an electrotechnical core which only comprises a second electrode structure and a second insulation layer. It is also conceivable for an electrotechnical core that can be inserted into a pocket to comprise only a first insulation layer, a first electrode structure, a second insulation layer, and a second electrode structure. A plasma applicator comprising an enclosure with a pocket can also comprise an electrotechnical core which is formed by a wire mesh, wire cloth or wire netting and which is inserted into the pocket. Optionally, a plasma applicator comprising an enclosure with a pocket can comprise a spacer structure and/or an access port for a fluid medium. Optionally, a plasma applicator comprising an enclosure with a pocket can also comprise an integrated power supply unit. A plasma applicator comprising an enclosure with a pocket can also comprise a contact or an electrode structure with at least one feature that changes in such a way as a consequence of use that it is no longer possible to transmit a voltage signal sufficient to ignite a plasma to the second electrode structure. The enclosure is preferably formed by a biocompatible material. Particularly if the electrotechnical core itself ensures contact protection, such as the electrotechnical core as per the first aspect, the enclosure can have a single layer embodiment and not provide contact protection. The enclosure can comprise silicone and/or lacquers and/or a parylene coating. The enclosure can also have a region occupied by barbed hooks, in which the plasma applicator can be fastened to a textile, for example a bandage. The plasma applicator could also comprise a separate layer which comprises an adhesion layer on one side and which is occupied by barbed hooks on the other side. With the side on which the adhesion layer is situated, this layer can be fastened to the plasma applicator and the plasma applicator can then be fastened to the layer on a textile with the side occupied by barbed hooks. In principle, such a layer within an adhesive layer on one side and with a barbed hook-occupied other side is also suitable for use with any other one of the plasma applicators described here, which should be releasably fastened to a textile.

A plasma applicator with an electrotechnical core and an enclosure with a pocket can also comprise at least one sensor which is embodied, during operation, to capture and output measurement variables relevant to a plasma treatment and/or wound healing, in particular physiological and/or physical measurement variables of a body segment covered by the plasma applicator during use.

A further aspect which can contribute to an improved plasma applicator, both on its own and independently of the remaining aspects described herein or in combination with one or more of these aspects, relates to a plasma applicator arranged on a bag. The plasma applicator can be realized in various variations and can, for example, also comprise an enclosure with a pocket and/or a feature ensuring single use. In addition or as an alternative thereto, the plasma applicator can also comprise an electrotechnical core according to the first aspect.

Thus, this aspect relates to a plasma applicator which comprises an electrotechnical core and an enclosure and which is affixed to a bag provided to enclose a certain body segment, for example a foot, and thus form a sealed gas space. The bag can be formed by a thin film. For a plasma treatment, a foot to be treated can be pushed into the bag. Then, the bag can be affixed, for example above the ankle, e.g., by means of a rubber band or a strap, in order to form a sealed gas space. The bag can have at least one hole, which preferably has a diameter of between 1 cm and 8 cm. The plasma applicator is arranged in such a way that the latter covers the hole. The plasma applicator is preferably arranged above the hole in such a way that the electrotechnical core adjoins the hole. On the side facing the hole, the plasma applicator can be affixed at the outer edge of the plasma applicator to the bag in a manner surrounding the at least one hole. During use, an ignited plasma can enter the bag through the hole and can interact with the surface to be treated. Consequently, this facilitates a large-area treatment of, e.g., a foot or at least a foot lower side.

A further aspect which can contribute to an improved plasma applicator, either on its own and independently of the remaining aspects described herein or in combination with individual aspects or a plurality of these aspects, relates to an access port. An access port can be realized as a constituent part of various plasma applicators. By way of example, a plasma applicator comprising an access port as per this aspect could comprise an electrotechnical core embodied according to the first aspect and/or an enclosure with a pocket and/or a feature for ensuring single use.

Thus, according to this aspect, a plasma applicator comprises an access port, wherein the access port is arranged and embodied in such a way that, before, during and/or after the plasma treatment, a fluid medium can be supplied to or removed from a sealed gas space formed by the enclosure between an electrotechnical core and a surface to be treated. A fluid medium is a gaseous and/or liquid medium and/or a liquid medium with added solid constituents in the form of, e.g., soluble and/or insoluble microparticles. A plasma applicator with an access port can have different designs and, in particular, be realized with various electrotechnical cores. An electrotechnical core of this plasma applicator with an access port preferably has a flexible embodiment and can be realized with different basic shapes, for example in round or quadrilateral fashion. An electrode structure of an electrotechnical core of a plasma applicator with an access port can have a specific geometry. If the electrotechnical core comprises at least two electrode structures with a specific geometry, the electrode sections of the two electrode structures can be arranged, for example, with a defined overlap with respect to one another. In particular, an electrotechnical core of a plasma applicator with an access port can comprise only a second electrode structure and a second insulation layer or only a first insulation layer, a first electrode structure, a second insulation layer, and a second electrode structure, or can be embodied in accordance with the above-described first aspect. An electrotechnical core of a plasma applicator with an access port can also be formed by a wire mesh, wire cloth or wire netting. By way of example, a suitable electrotechnical core can be produced by virtue of an electrode carrier, which represents an insulation layer, being respectively printed with an electrode structure on one or both sides. This can be carried out using a rotary screen printing method. Furthermore, an access port can comprise a valve and/or a socket or a mating thread for a socket.

A plasma applicator with an access port can also comprise a contact or an electrode structure with at least one feature that changes in such a way as a consequence of use that it is no longer possible to transmit a voltage signal sufficient to ignite a plasma to the second electrode structure.

Preferably, the enclosure of a plasma applicator with an access port can at least partly enclose the electrotechnical core. A plasma applicator with an access port can also comprise an enclosure with a pocket, into which an electrotechnical core can be inserted. Preferably, an enclosure of a plasma applicator with an access port is formed by a biocompatible material. By way of example, an enclosure can comprise silicone, lacquers, textile and/or a parylene coating. The enclosure can also comprise a VAC film. If the electrotechnical core itself already has an embodiment that is safe to touch, the enclosure can have a single layer embodiment and can be designed in such a way that the latter itself need not ensure contact protection. The enclosure can also comprise an access port, by means of which a fluid medium can be discharged from the sealed gas space. A plasma applicator with an access port can also comprise an integrated power supply unit. A plasma applicator with an access port can also comprise a spacer structure. The spacer structure is preferably formed by a biocompatible material. By way of example, the spacer structure can be formed by a VAC foam. A plasma applicator with an access port can also comprise an adhesion layer, which is preferably arranged as a last layer on the side of the plasma applicator facing a surface to be treated and which is embodied to affix the plasma applicator to a surface to be treated. A plasma applicator with an access port can also comprise a plug-in apparatus that can be securely connected to the electrotechnical core. The plug-in apparatus preferably has a tab-shaped embodiment. A plasma applicator with an access port can also comprise at least one sensor which is embodied to capture and output measurement variables during use, said measurement variables being relevant to a plasma treatment and/or to wound healing, in particular physiological and/or physical measurement variables of a body segment covered by the plasma applicator during use.

A plasma applicator with an access port can also be embodied to remain on a surface to be treated over a relatively long period of time for treatment purposes, in particular over the period of time required for wound healing. Such a plasma applicator with an access port can be embodied to seal a surface to be treated. In the case of such a plasma applicator, provided for sealing, with an access port, the adhesion layer is preferably formed by a silicone or a PU adhesive and the enclosure is formed by an air-impermeable material. In particular, the adhesion layer can comprise an adhesive which loses its adhesive properties by way of UV light exposure or by contact with alcohol.

A further aspect which can contribute to an improved plasma applicator, on its own and independently of the remaining aspects described herein or in combination with individual aspects or a plurality of these aspects, relates to an integrated power supply unit. A power supply unit as per this aspect can be integrated in various plasma applicators. By way of example, the power supply unit can be integrated in a plasma applicator comprising an access port and/or an electrotechnical core embodied according to the first aspect and/or an enclosure with a pocket and/or a feature for ensuring single use.

This aspect can be realized by a plasma applicator with an integrated power supply unit, the latter comprising an energy store that is electrically connected to an electrotechnical core of the plasma applicator and embodied to transmit a voltage signal sufficient to ignite a plasma to an electrode structure of the electrotechnical core during operation. By way of example, the energy store can be an accumulator, a battery or a capacitor. A power supply unit of this type, integrated in the plasma applicator, can be implemented in combination with various types of plasma applicators. In particular, an electrotechnical core of a plasma applicator of this aspect can comprise only a second electrode structure and a second insulation layer or only a first insulation layer, a first electrode structure, a second insulation layer, and a second electrode structure, or can be embodied in accordance with the above-described first aspect. A suitable electrotechnical core can be produced using a rotary screen printing method, in which a respective electrode structure is printed onto one or both sides of an electrode carrier. The insulation layer between the two electrode structures is then realized by the electrode carrier. An electrotechnical core of a plasma applicator with an integrated power supply unit can also be formed by a wire mesh, wire cloth or wire netting. An insulation layer arranged on the side of the plasma applicator facing a surface to be treated is preferably formed by a biocompatible material. Preferably, the electrotechnical core of the plasma applicator with the integrated power supply unit has a flexible embodiment such that the plasma applicator can be adapted in terms of its shape to the shape of a surface to be treated. The electrotechnical core of the plasma applicator with an integrated power supply unit can comprise at least one electrode structure with a specific geometry. If a plurality of electrode structures of the electrotechnical core have a specific geometry, these can be arranged with respect to one another in such a way that the electrode sections of the respective electrode structures have a defined overlap with one another.

A plasma applicator with an integrated power supply unit can also comprise a contact or an electrode structure with at least one feature that changes in such a way as a consequence of use that it is no longer possible to transmit a voltage signal sufficient to ignite a plasma to the second electrode structure. A plasma applicator with an integrated power supply unit can also comprise an enclosure with a pocket, into which an electrotechnical core can be inserted.

Preferably, a plasma applicator with an integrated power supply unit has an enclosure which at least partly, or even completely, encloses the electrotechnical core. In particular, a plasma applicator with an integrated power supply unit, in which the electrotechnical core is completely enclosed by an enclosure, is suitable for being implanted in a human or animal body for a plasma treatment. An enclosure of a plasma applicator with an integrated power supply unit is preferably formed by a biocompatible material. An enclosure of a plasma applicator with an integrated power supply unit can comprise silicone, lacquers, textiles and/or a parylene coating. If the electrotechnical core of a plasma applicator with an integrated power supply unit itself has an embodiment that is safe to touch, the enclosure can have a single layer embodiment and need not ensure contact protection itself. A plasma applicator with an integrated power supply unit can also comprise a spacer structure, which is preferably formed of a biocompatible material and intended to create a defined distance between the plasma applicator and a surface to be treated, in which distance a plasma can ignite.

A plasma applicator with an integrated power supply unit can also comprise an access port through which a fluid medium can be supplied to or removed from a sealed gas space that is formed before, during or after a plasma treatment.

A plasma applicator with an integrated power supply unit can comprise an electrical circuit which is preferably connected between the integrated power supply unit and the electrotechnical core and which, during operation, is embodied to convert a voltage signal provided by the power supply unit into a voltage signal sufficient to ignite a plasma and to transmit the converted voltage signal to the electrotechnical core. The electrical circuit is then integrated in the plasma applicator as a component of said plasma applicator. The electrical circuit could also be realized as a constituent part of the power supply unit such that the power supply unit is embodied to provide during operation a voltage signal sufficient to ignite a plasma. The integrated power supply unit can also comprise receiver coil arrangements electrically connected to the energy store and can be embodied in such a way that the energy store can be charged by virtue of electrical energy being inductively transferred from a transmitter coil arrangement to the receiver coil arrangement in the plasma applicator by way of said transmitter coil arrangement. A power supply unit with receiver coil arrangements is particularly suitable for a plasma applicator that is intended to be implanted. Particularly if a plasma applicator with an integrated power supply unit is not intended to be implanted in a body, said plasma applicator can comprise a plug-in apparatus that is electrically conductively connected to the integrated power supply unit and intended to be connected to an external power supply unit in order to charge the energy store of the integrated power supply unit.

A plasma applicator with an integrated power supply unit can also comprise at least one sensor which is embodied to capture and output measurement variables during use, said measurement variables being relevant to a plasma treatment and/or to wound healing, in particular physiological and/or physical measurement variables of a body segment covered by the plasma applicator during use. Particularly if a plasma applicator with an integrated power supply unit is intended to be implanted in a human or animal body, it may be advantageous if said plasma applicator comprises at least one sensor. Then, the plasma applicator can remain implanted in the body over a relatively long period of time, which includes the time for a wound to heal, in particular, but may also include months or even years. During this period of time, the at least one sensor of the plasma applicator can capture and output measurement variables relevant to a plasma treatment and/or to wound healing. The state of a wound and/or the progress of wound healing can then be assessed on the basis of these output measurement variables. Particularly if a plasma applicator is intended to be implanted, it is preferable for measurement variables captured by a sensor to be able to be transferred and/or read wirelessly. By way of example, the plasma applicator can comprise an RFID transponder, which can access data representing the captured measurement variables stored in a memory chip and can transfer said data to a reader if a corresponding request is made to the transponder by a reader.

Even if the plasma applicator with an integrated power supply unit is not intended to be implanted but is applied or affixed from the outside to a surface to be treated during use, it may be advantageous if said plasma applicator remains after a plasma treatment on a wound to be treated for a relatively long period of time, in particular for the time the wound takes to heal, e.g., even over weeks or months. Preferably, the plasma applicator with an integrated power supply unit is embodied in such a way that a surface to be treated can be sealed with the plasma applicator. In the case of a such a plasma applicator, provided for sealing, with an integrated power supply unit, the adhesion layer is preferably formed by a silicone or a PU adhesive and the enclosure is formed by an air-impermeable material. In particular, the adhesion layer can comprise an adhesive which loses its adhesive properties by way of UV light exposure or by contact with alcohol. If a plasma applicator with an integrated power supply unit intended for sealing comprises at least one sensor, this sensor can output and capture measurement variables during the application, said measurement variables being relevant to a plasma treatment and/or to wound healing, when a surface to be treated is sealed by the plasma applicator.

A further aspect which can contribute to an improved plasma applicator, on its own and independently of the remaining aspects described herein or in combination therewith, relates to an autonomous, mobile power supply unit. The power supply unit as per this aspect can be used to provide a voltage signal to different plasma applicators. By way of example, such different plasma applicators can comprise an integrated power supply unit and/or an access port and/or an electrotechnical core embodied according to the first aspect and/or an enclosure with a pocket and/or a feature for ensuring single use.

According to this aspect, the object set forth at the outset is achieved by an autonomous, mobile power supply unit with an insertion apparatus and an energy store, for connection to a plug-in apparatus of a plasma applicator and for providing a voltage signal sufficient to ignite a plasma to a plug-in apparatus plugged together with the insertion apparatus. The power supply unit preferably comprises an electrical circuit which is embodied to convert a voltage provided by the energy store into a voltage signal sufficient to ignite a plasma and to transmit said voltage signal to the insertion apparatus. Such a power supply unit is preferably embodied as an autonomous unit only a few cubic centimeter big, which is to be connected mechanically and electrically to a plasma applicator and which can be fastened to, e.g., a patient together with the plasma applicator. In contrast to the power supply unit integrated in a plasma applicator, the autonomous, mobile power supply unit as per this aspect is replaceably connected to the plasma applicator. An insertion apparatus as per this aspect can be implemented in combination with various plasma applicators and, for example, can be connected to a plasma applicator which comprises an electrotechnical core with only a second electrode structure and a second insulation layer or with only a first insulation layer, a first electrode structure, a second insulation layer and a second electrode structure or which is embodied in accordance with the above-described first aspect. An insertion apparatus as per this aspect can be connected to a plasma applicator comprising an electrotechnical core which is formed by a wire mesh, wire cloth or wire netting. An insertion apparatus as per this aspect can be connected to a plasma applicator having at least one feature that changes in such a way as a consequence of use that it is no longer possible to transmit a voltage signal sufficient to ignite a plasma to the plasma applicator. An insertion apparatus as per this aspect can also comprise a tube which can be connected to, or plugged together with, an access port of a plug-in apparatus or of a plasma applicator.

A further aspect which can contribute to an improved plasma applicator, on its own and independently of the remaining aspects described herein or in combination with one or more of these aspects, relates to an electrotechnical core comprising at least one insulated electrically conductive wire. The electrotechnical core as per this aspect can be implemented as a constituent part of various plasma applicators. By way of example, it could be implemented in plasma applicators comprising an integrated power supply unit and/or an access port and/or an enclosure with a pocket and/or a feature for ensuring single use.

Thus, this aspect relates to an electrotechnical core comprising at least one insulated electrically conductive wire, which is driven by a voltage signal during operation, with a counter electrode in that case being realized, preferably, by a further insulated electrically conductive wire or by a surface to be treated itself. Preferably, an enclosure is provided in order to enclose the at least one insulated electrically conductive wire on a surface to be treated, in such a way that a gas space sealed to the best possible extent is formed, within which a plasma can ignite during the plasma treatment. An enclosure can also comprise a pocket, into which the electrotechnical core formed by the electrically conductive wire can be inserted. By way of example, such an electrotechnical core can be a wire mesh, a wire cloth or a wire netting, which is formed by one or more electrically conductive, insulated wires.

In particular, an electrode structure, which is driven during the application and formed by one or more insulated, electrically conductive wires, and a further electrode structure, which is likewise formed by one or more insulated, electrically conductive wires and which realizes a counter electrode during operation, can together form a wire mesh, a wire fabric or a wire netting by virtue of corresponding insulated wires of the two electrode structures being interwoven, for example. It is also conceivable that an electrically conductive wire forming the driven electrode structure during use and a further wire realizing a counter electrode during operation are arranged together in a cable sheathing but are galvanically isolated from one another. It is also conceivable that a simple electrically conductive, insulated wire forms a simple electrode structure without the wire being arranged in a comparatively complicated structure such as a fabric or a mesh. During use, a counter electrode is then preferably realized by a surface to be treated. A plasma applicator with an electrotechnical core in the form of an insulated wire can also be provided with a plug-in apparatus of the type described here. Such a plug-in apparatus can also have a feature ensuring single use of the plasma applicator. An electrical conductor can also be connected to a mobile power supply unit which, during operation, transmits a voltage signal sufficient to ignite a plasma to the electrically conductive, insulated wire by switching a switching contact. A plasma applicator with an electrotechnical core which comprises at least one insulated electrically conductive wire can also comprise at least one sensor which is embodied, during operation, to capture and output measurement variables relevant to a plasma treatment and/or wound healing, in particular physiological and/or physical measurement variables of a body segment covered by the plasma applicator during use.

A further aspect which can contribute to an improved plasma applicator, on its own and independently of the remaining aspects described herein or in combination with one or more of these aspects, relates to a plasma applicator with an electrotechnical core, an enclosure, a spacer structure, an adhesion layer, and a plug-in apparatus. The plasma applicator as per this aspect can also comprise an integrated power supply unit and/or an access port and/or an enclosure with a pocket and/or a feature for ensuring single use and/or an electrotechnical core comprising at least one insulated electrically conductive wire or an electrotechnical core embodied as per the first aspect. To ignite a plasma, the plasma applicator as per this aspect can also be connected to a mobile power supply unit.

According to this aspect, a plasma applicator comprises an electrotechnical core, an enclosure, a spacer structure, an adhesion layer, and a plug-in apparatus. The electrotechnical core preferably has a flexible embodiment. The electrotechnical core can be realized with the different basic shapes, for example a round or a polygonal basic shape and, in particular, a quadrilateral basic shape. Preferably, the electrotechnical core is an electrotechnical core as per the first aspect; i.e., it has an embodiment with six layers and is itself safe to touch during operation. However, the plasma applicator as per this aspect can also be implemented with various different electrotechnical cores. At least one electrode structure of the electrotechnical core can have a specific geometry. If at least two electrode structures of the electrotechnical core have a specific geometry, the electrode sections of these electrode structures are preferably arranged with a defined overlap with respect to one another. If the electrotechnical core comprises a plurality of electrode structures, an insulation layer is preferably arranged between two of the electrode structures in each case in order to galvanically isolate the corresponding electrode structures from one another. Preferably, at least one further insulation layer is arranged on the side of the plasma applicator facing the surface to be treated and is preferably formed by a biocompatible material. Preferably, the enclosure at least partly encloses the electrotechnical core. This enclosure can be embodied in such a way that, during operation, it forms a sealed gas space between the electrotechnical core and a surface to be treated. Preferably, the enclosure is formed by a biocompatible material. Particularly if the electrotechnical core itself already has an embodiment that is safe to touch, the enclosure can have a single layer embodiment and need not ensure contact protection itself. By way of example, the enclosure can comprise silicone, lacquers or a parylene coating. The spacer structure is preferably formed by a biocompatible material. The spacer structure is preferably arranged on the side of the plasma applicator facing the surface to be treated and adjacent to the electrode structure of the plasma applicator facing the surface to be treated and is embodied to create between an electrotechnical core and a surface to be treated a defined distance, and hence a defined gas volume, in which a generated plasma can be distributed. By way of example, the spacer structure can have a honeycomb shape or an X, O, Z, M, E or a W shape. The adhesion layer is embodied to affix the plasma applicator on a surface to be treated and is preferably arranged as a last layer on the side of the plasma applicator facing the surface to be treated. By way of example, the adhesion layer can be arranged along the perimeter of the plasma applicator like a frame at the side of the plasma applicator facing the surface to be treated. However, the adhesion layer could be arranged over the entire area on the side of the plasma applicator facing a surface to be treated. The plug-in apparatus is preferably securely connected to an electrotechnical core and embodied to transmit a voltage signal to a driven electrode structure of the electrotechnical core during operation. Such plug-in apparatuses are described in detail below. The plug-in apparatus preferably has a tab-shaped embodiment. A tab-shaped plug-in apparatus can be formed by virtue of the electrode structures and the insulation layers of the electrotechnical core being extended onto this tab. The size of the plug-in apparatus is preferably dimensioned in such a way depending on the length of the creepage distances that no partial discharges arise within a plugged together plug-in apparatus and an insertion apparatus during operation.

A further aspect which can contribute to an improved plasma applicator, both on its own and independently of the remaining aspects described herein or in combination with individual aspects or a plurality of these aspects, relates to an adhesion layer for a plasma applicator, embodied to simultaneously fulfill the function of a spacer structure. In particular, the adhesion layer as per this aspect represents a dedicated product and can be used as a module together with differently embodied plasma applicators. By way of example, such plasma applicators can comprise an integrated power supply unit and/or an access port and/or an enclosure with a pocket and/or a feature for ensuring single use and/or an electrotechnical core comprising at least one insulated electrically conductive wire or an electrotechnical core embodied as per the first aspect.

This aspect relates to an adhesion layer for a plasma applicator, embodied to simultaneously fulfill the function of a spacer structure. An adhesion layer as per this aspect is embodied such that, during operation, it can be used to affix a plasma applicator on a surface to be treated and it then allows a defined distance to be established between an electrotechnical core of a plasma applicator and a surface to be treated such that a plasma arising can be distributed over the surface to be treated. By way of example, such an adhesion layer can be formed by an adhesive, in particular a silicone or polyurethane (PU) adhesive. By way of example, an adhesive forming the adhesion layer can have a specific geometry, for example a honeycomb pattern or an X, O, Z, M, E or an W shape and can be applied on the side of a plasma applicator facing a surface to be treated. For a plasma treatment, the plasma applicator with an applied adhesion layer is placed on a surface to be treated and affixed on the latter by means of the adhesion layer. When in contact with the surface to be treated, the adhesive forming the adhesion layer adheres with a specific geometry to the surface to be treated such that a defined gas volume is created in each region without adhesive, in which the generated plasma can be distributed. Alternatively, the adhesion layer can be applied on the surface to be treated, preferably around the wound to be treated, for the purposes of the plasma treatment and the wound-facing side of the plasma applicator can subsequently be affixed to the wound-distant side of the adhesion layer affixed to the surface to be treated such that a defined gas volume is created in each region without adhesive, in which a generated plasma can be distributed.

A further aspect which can contribute to an improved plasma applicator, on its own and independently of the remaining aspects described herein or in combination with at least one of these aspects, relates to an enclosure with insertion slots, into which a power supply unit or an insertion apparatus can be inserted. An enclosure as per this aspect can be realized for various plasma applicators which, for example, comprise an integrated power supply unit and/or an access port and/or an enclosure with a pocket and/or a feature for ensuring single use and/or an electrotechnical core comprising at least one insulated electrically conductive wire or an electrotechnical core embodied as per the first aspect. The power supply unit that can be inserted into the insertion slots can be an autonomous, mobile power supply unit, in particular. The insertion apparatus that can be inserted into the insertion slots can be connected, in particular, by way of a cable to a power supply unit that tends to be used in stationary fashion.

According to this aspect, a plasma applicator with an electrotechnical core comprises an enclosure with insertion slots. The electrotechnical core can be an electrotechnical core as per any one of the embodiment variants described herein. The electrotechnical core preferably has a flexible embodiment. The electrotechnical core can be designed with any basic shape. However, a quadrilateral or round basic shape is preferred. Preferably, the electrotechnical core is a six-layer electrotechnical core which itself already has an embodiment that is safe to touch, as per the first aspect. At least one electrode structure of the electrotechnical core can have a specific geometry. However, the electrotechnical core could also have four layers and consequently not be safe to touch. The electrotechnical core could also comprise a plurality of electrode structures with a specific geometry. If an electrotechnical core comprises a plurality of electrode structures with specific geometries, the electrode sections of the respective electrode structures can be arranged with a defined overlap with respect to one another. If the electrotechnical core comprises a plurality of electrode structures, at least one insulation layer is preferably arranged between two adjacent electrode structures in each case in order to galvanically isolate the corresponding two electrode structures from one another. By way of example, a suitable electrotechnical core can be produced using a rotary screen printing method by virtue of a respective electrode structure being printed onto one or both sides of an electrode carrier. Preferably, the electrotechnical core comprises a further insulation layer, which is arranged on the side of the plasma applicator facing a surface to be treated. This further insulation layer is preferably formed by a biocompatible material. The enclosure can be designed such that it completely encloses the electrotechnical core. By way of example, the enclosure can comprise silicone, lacquers or a parylene coating. Preferably, the enclosure comprises insertion slots which are arranged on the side of the plasma applicator facing away from the surface to be treated and which are embodied such that a power supply unit, complementary to the insertion slots, or an insertion apparatus can be inserted into the insertion slots in order then to be connected to contacts of the electrotechnical core.

A further aspect which can contribute to an improved plasma applicator, on its own and independently of the remaining aspects described herein or in combination with at least one of these aspects, relates to an enclosure with absorbing properties. Additionally, the enclosure can have a pocket, into which an electrotechnical core can be inserted, and/or insertion slots, into which a power supply unit or an insertion apparatus can be inserted.

An enclosure as per this aspect can be realized for various plasma applicators which, for example, comprise an integrated power supply unit and/or an access port and/or a feature for ensuring single use and/or an electrotechnical core comprising at least one insulated electrically conductive wire or an electrotechnical core embodied as per the first aspect.

According to this aspect, a plasma applicator can comprise an electrotechnical core, an enclosure with absorbing properties, an adhesion layer, a spacer structure, and a plug-in apparatus. Preferably, the electrotechnical core is embodied as per one of the variants of an electrotechnical core described herein. By way of example, the electrotechnical core can be embodied as per the electrotechnical core of the first aspect and can itself already ensure contact protection. A suitable electrotechnical core can be produced using a rotary screen printing method, in which a respective electrode structure is printed onto one or both sides of an electrode carrier. Preferably, the electrotechnical core has a flexible embodiment. The electrotechnical core can be implemented in various basic shapes. The electrotechnical core can have a basic shape which is, e.g., round or polygonal, preferably quadrilateral. At least one electrode structure of the electrotechnical core can have a specific geometry. If a plurality of electrode structures of the electrotechnical core have a specific geometry, these electrode structures, in particular, can be arranged with respect to one another in such a way that the electrode sections of the respective electrode structures have defined overlap with one another. If the electrotechnical core comprises a plurality of electrode structures, respectively adjacent electrode structures are preferably galvanically isolated from one another by an insulation layer. Preferably, a further insulation layer is arranged on the side facing a surface to be treated and is situated during use between a surface to be treated and that electrode structure which has the smallest distance from the surface to be treated during use. Even if the electrotechnical core only comprises one electrode structure, an insulation layer is preferably arranged adjacent to this electrode structure on the side of the plasma applicator facing a surface to be treated. An insulation layer arranged on the side of the plasma applicator facing a surface to be treated is preferably formed by a biocompatible material.

The enclosure preferably completely encloses the electrotechnical core and has absorbing properties at least in one portion. The enclosure can also have a pocket, in which the electrotechnical core is arranged in removable fashion. The enclosure with absorbing properties preferably consists of at least one layer of liquid-absorbing and/or liquid-removing and/or liquid-distributing materials, such as, e.g., textile, gauze, PU foam, distributor layer, wound contact layer, spacer structure. The spacer structure is preferably formed by a biocompatible material and can be realized by the enclosure itself. Preferably, the spacer structure is formed by an air-permeable material. The spacer structure can also comprise gauze, absorber, textiles, cellulose or PE foam. The adhesion layer is preferably arranged, over the whole area, as a last layer on the side of the plasma applicator facing a surface to be treated and is embodied to affix the plasma applicator to a surface to be treated. The adhesion layer can also have larger and/or smaller cutouts. The plug-in apparatus can be securely connected to the electrotechnical core and preferably has a tab-shaped embodiment. A tab-shaped plug-in apparatus can be realized by virtue of the electrode structures and the insulation layers of the electrotechnical cores being extended in tab shape. The size of the plug-in apparatus is preferably dimensioned in such a way depending on the length of the creepage distances that no partial discharges arise within a plugged together plug-in apparatus and an insertion apparatus during operation.

A further aspect which can contribute to an improved plasma applicator, on its own and independently of the remaining aspects described herein or in combination with at least one of these aspects, relates to a plasma applicator which is intended to remain on a surface to be treated for a relatively long period of time. The plasma applicator as per this aspect can also comprise an integrated power supply unit and/or an access port and/or a feature for ensuring single use and/or an electrotechnical core comprising at least one insulated electrically conductive wire or an electrotechnical core embodied as per the first aspect and/or an enclosure with absorbing properties and/or with a pocket and/or insertion slots.

Thus, this aspect relates to a plasma applicator intended to remain on a surface to be treated for a relatively long period of time, which comprises an electrotechnical core, an enclosure, an adhesion layer, a spacer structure, a plug-in apparatus and at least one sensor. The plasma applicator can be realized with various electrotechnical cores. However, the electrotechnical core preferably is an electrotechnical core as per the first aspect; i.e., it has an embodiment with six layers that is itself safe to touch. Preferably, the electrotechnical core has such a flexible embodiment that the latter can be adapted in terms of its shape to a shape of a surface to be treated. By way of example, the electrotechnical core can have a round basic shape, a quadrilateral basic shape or any other polygonal basic shape. At least one electrode structure of the electrotechnical core can have a specific geometry. If a plurality of electrode structures of the electrotechnical core have a specific geometry, these electrode structures, in particular, can be arranged with respect to one another in such a way that the electrode sections of the respective electrode structures have a defined overlap with one another. If the electrotechnical core comprises a plurality of electrode structures, respectively adjacent electrode structures are preferably galvanically isolated from one another by an insulation layer. Preferably, a further insulation layer is arranged on the side facing a surface to be treated and is situated during use between a surface to be treated and that electrode structure which is arranged at the shortest distance from the surface to be treated during use. Even if the electrotechnical core only comprises one electrode structure, an insulation layer is preferably arranged adjacent to this electrode structure on the side of the plasma applicator facing a surface to be treated. An insulation layer arranged on the side of the plasma applicator facing a surface to be treated is preferably formed by a biocompatible material.

The enclosure at least partly encloses the electrotechnical core. Preferably, the enclosure is formed by a biocompatible material. By way of example, the enclosure can comprise silicone, lacquers or a parylene coating. Particularly if the electrotechnical core of the plasma applicator itself already has an embodiment that is safe to touch, the enclosure can have a single layer embodiment and need not ensure contact protection itself. The spacer structure is preferably arranged adjacent to the electrotechnical core on the side of the plasma applicator facing a surface to be treated. The spacer structure is preferably formed by a biocompatible material. The adhesion layer is preferably arranged as last layer on the side of the plasma applicator facing a surface to be treated. By way of example, the adhesion layer can be guided along the perimeter of the plasma applicator like a frame on the side of the plasma applicator facing a surface to be treated and can thus form an adhesive edge.

The plug-in apparatus can be securely connected to the electrotechnical core. The plug-in apparatus preferably has a tab-shaped embodiment by virtue of the electrode structures and the insulation layers of the electrotechnical core being extended in a tab shape. The at least one sensor is preferably embodied to capture and output measurement variables during use, said measurement variables being relevant to a plasma treatment and/or to wound healing, in particular physiological and/or physical measurement variables of a body segment covered by the plasma applicator during use.

For treating a surface over a relatively long period of time, which may, in particular, include the time it takes for a wound to heal, the plasma applicator can be embodied in such a way that a surface to be treated is sealed by the plasma applicator during use. Then, the adhesion layer is preferably formed by a silicone or PU adhesive and the enclosure is formed by an air-impermeable material. In particular, the adhesion layer can have an adhesive which loses its adhesive properties when exposed to UV light or when it comes into contact with alcohol so that the plasma applicator can be removed from a surface to be treated after a relatively long treatment. During the duration of a long-term treatment, measurement variables output by the at least one sensor, for example within the scope of telemonitoring or home monitoring, can be evaluated and the progress of wound healing can be assessed on the basis thereof.

A further aspect which can contribute to an improved plasma applicator, on its own and independently of the remaining aspects described herein or in combination with at least one of these aspects, relates to a spacer structure, itself a plasma source, for a plasma applicator. A spacer structure as per this aspect represents an independent product and can be used as a module together with differently embodied plasma applicators. By way of example, such plasma applicators can comprise an integrated power supply unit and/or an access port and/or a feature for ensuring single use and/or an electrotechnical core comprising at least one insulated electrically conductive wire or an electrotechnical core embodied as per the first aspect and/or an enclosure with absorbing properties and/or with a pocket and/or insertion slots.

This aspect relates to a spacer structure, itself a plasma source, for a plasma applicator. Thus, the spacer structure fulfills both the function of a spacer structure and that of the plasma source. Such a spacer structure has at least one electrode structure and is preferably designed with a specific geometry. In particular, the spacer structure can have a number of cavities or passages, which are designed such that a plasma generated during the application can interact with a surface to be treated. If the spacer structure only comprises an electrode structure, a voltage signal is applied to the latter during use for the purposes of igniting a plasma. Then, the counter electrode is preferably realized by the surface to be treated itself. The spacer structure can also have an electrode structure, which is driven during use, and a counter electrode. By way of example, the spacer structure can be formed by a ribbon cable which is a plasma source at the same time. The ribbon cable can also be a two-core ribbon cable. An insulation of a ribbon cable preferably has a thickness of between 5 µm and several 100 µm, preferably of less than 100 µm, preferably of between 40 µm and 60 µm, preferably of 50 µm.

At least the regions of the spacer structure which come into contact with a surface to be treated during use are preferably formed by a biocompatible material.

The spacer structure can be connected to a plug-in apparatus. In the case of a spacer structure with a plug-in apparatus, at least one electrode structure of the spacer structure, in particular, is electrically conductively connected to a conductor track of the plug-in apparatus such that when the plug-in apparatus is connected to a power supply unit, for example via a cable, a voltage signal sufficient to ignite a plasma can be transmitted to the at least one electrode structure during use.

During use, the spacer structure can be affixed to a surface to be treated by means of an adhesion layer. However, it is preferable for the spacer structure for a plasma treatment to be affixed to a surface to be treated by means of a film, in particular a film that has adhesive properties on one side. Then, the film is pulled over the spacer structure and the surface to be treated such that the spacer structure is affixed to the surface to be treated by the film. Preferably, a sealed gas space is formed by the applied film, in which gas space a plasma can be generated during use and said plasma can interact with the surface to be treated. Use can also be made of a film that has no surface with adhesive properties. Such a film, which itself does not adhere to the surface to be treated, can be affixed to the surface to be treated by way of an adhesion layer. Furthermore, such a film can be affixed to the surface to be treated by virtue of generating a vacuum in the sealed gas space. Use can also be made of a film in which an adhesive contact between sections of this film arises when said sections are brought together. Such a film can be found with overlap over a body segment of a patient, for example, in order thus to affix the spacer structure on a surface to be treated and form a sealed gas space.

A further aspect which can contribute to an improved plasma applicator, on its own and independently of the remaining aspects described herein or in combination with at least one of these aspects, relates to a plasma applicator which is intended to be applied to a surface to be treated in certain three-dimensional shapes. A plasma applicator as per this aspect can also comprise an integrated power supply unit and/or an access port and/or a feature for ensuring single use and/or an electrotechnical core comprising at least one insulated electrically conductive wire or an electrotechnical core embodied as per the first aspect and/or an enclosure with absorbing properties and/or with a pocket and/or insertion slots.

A further aspect relates to a plasma applicator which is embodied to be applied to a surface to be treated in a specific form, for example in the form of a tent or a cone, for a plasma treatment. A plasma applicator as per this aspect comprises an electrotechnical core, an enclosure, an adhesion layer, and a plug-in apparatus. The plasma applicator can be realized with various electrotechnical cores. However, the electrotechnical core preferably is an electrotechnical core as per the first aspect; i.e., it is itself safe to touch. A suitable electrotechnical core can be produced using a rotary screen printing method, for example, in which a respective electrode structure is printed onto one or both sides of an electrode carrier. The basic shape of the plasma applicator can arise, in particular, from that three-dimensional shape into which the plasma applicator should be brought for a plasma treatment. By way of example, if the plasma applicator is intended to be brought into a conical form for a plasma treatment, the basic shape of the plasma applicator can correspond to the rolled-open lateral face of the cone. Such a plasma applicator preferably has a flexible shape. For a plasma treatment, a flexible plasma applicator can be placed around a tube or a cable of an existing access to a patient, for example, without the access to the body to be treated, already laid, having to be removed for a plasma treatment.

However, the plasma applicator can also have a rigid shape; for example, it can already have the shape of a cone. In particular, such a plasma applicator with a rigid shape can have a hole or a slot, through which a tube or cable can be guided. By way of example, such a hole or such a slot can be found at the tip of the cone or in the lateral face of a conical plasma applicator.

At least one electrode structure of the electrotechnical core can have a specific geometry. If a plurality of electrode structures of the electrotechnical core have a specific geometry, the electrode sections of the respective electrode structures are preferably arranged with respect to one another with a defined overlap. Preferably, an insulation layer is arranged between adjacent electrode structures, said insulation layer being embodied to galvanically isolate the two adjacent electrode structures from one another. On the side facing a surface to be treated, the plasma applicator preferably comprises a further insulating layer, which is preferably formed by a biocompatible material.

The enclosure can partly or even completely enclose the electrotechnical core. The enclosure is preferably formed by a biocompatible material. If the electrotechnical core itself already has an embodiment that is safe to touch, it may be sufficient for the enclosure to be formed by only one layer and not to ensure a contact protection itself. By way of example, the enclosure can comprise silicone, lacquers, textiles and/or a parylene coating. The adhesion layer is preferably arranged in such a way that the plasma applicator can be affixed in the shape provided for a plasma treatment to a surface to be treated. By way of example, if the plasma applicator is intended to be applied in a conical form to a surface to be treated, the adhesion layer is preferably arranged on the side of the lateral face facing the surface to be treated.

A further aspect which can contribute to an improved plasma applicator, on its own and independently of the remaining aspects described herein or in combination with at least one of these aspects, relates to a plasma applicator which is suitable, in particular, for treating large area wounds with an area of some and/or several decimeters squared (e.g., burns and, in particular, large area burns). By way of example, such a plasma applicator can also comprise an integrated power supply unit and/or an access port and/or a feature for ensuring single use and/or an electrotechnical core comprising at least one insulated electrically conductive wire or an electrotechnical core embodied as per the first aspect and/or an enclosure with absorbing properties and/or with a pocket and/or insertion slots.

A further aspect relates to a plasma applicator which is suitable, in particular, for the treatment of large area wounds (e.g., large area burns). The plasma applicator is suitable for being fastened with a side facing away from the surface to be treated to a carrier material and for being used together with this carrier material. By way of example, this carrier material can be a space blanket or a bandage or a large film. The plasma applicator as per this aspect comprises an electrotechnical core, an enclosure, and an adhesion layer. Preferably, the plasma applicator furthermore comprises an integrated power supply unit. The plasma applicator can be realized with various electrotechnical cores. By way of example, a suitable electrotechnical core can be produced using a rotary screen printing method. The electrotechnical core can also have at least one layer in which a plurality of independent electrode structures are arranged and not electrically interconnected, and respectively form electrically independent treatment regions. The plurality of electrode structures within a layer can be driven with a time offset, i.e., in cascaded fashion. However, the electrotechnical core preferably is an electrotechnical core as per the first aspect and is itself safe to touch. The electrotechnical core can also be implemented in various basic shapes. At least one electrode structure of the electrotechnical core can have a specific geometry. If a plurality of electrode structures of the electrotechnical core have a specific geometry, these electrode structures, in particular, can be arranged with respect to one another in such a way that the electrode sections of the respective electrode structures have a defined overlap with one another. If the electrotechnical core comprises a plurality of electrode structures, respectively adjacent electrode structures are preferably galvanically isolated from one another by an insulation layer. Preferably, at least one further insulation layer is arranged on the side of the plasma applicator facing a surface to be treated and is preferably formed by a biocompatible material. The enclosure at least partly encloses the electrotechnical core and is preferably formed by a biocompatible material. If the electrotechnical core itself already has an embodiment that is safe to touch, the enclosure can have a single layer embodiment and need not ensure contact protection itself. By way of example, the enclosure can comprise silicone, lacquers, textiles and/or a parylene coating.

The adhesion layer is preferably arranged as last layer on the side of the plasma applicator facing away from a surface to be treated. The adhesion layer is preferably embodied to fasten the plasma applicator on its side facing away from a surface to be treated to a carrier material, for example a space blanket or a film.

The plasma applicator can also have a plug-in apparatus, which preferably has a tab-shaped embodiment. The plug-in apparatus can be securely connected to the electrotechnical core.

The power supply unit optionally integrated into the plasma applicator comprises an energy source, which can be an accumulator, a battery or a capacitor. The power supply unit is preferably connected to an electrode structure of the electrotechnical core and is embodied to provide a voltage signal sufficient to ignite a plasma. The power supply unit can comprise an electrical circuit which is embodied to convert a voltage signal into a voltage signal sufficient to ignite a plasma. The integrated power supply unit can also comprise receiver coil arrangements electrically connected to the energy store and can be embodied in such a way that the energy store can be charged by virtue of electrical energy being inductively transferred from a transmitter coil arrangement to the receiver coil arrangement in the plasma applicator by way of said transmitter coil arrangement. If a plasma applicator comprises a plug-in apparatus, the plug-in apparatus is preferably electrically conductively connected to the power supply unit such that the power source, in particular an accumulator or capacitor, of the power supply unit can be charged by connecting the plug-in apparatus to an external power supply unit.

Preferred Embodiment Variants of a Plasma Applicator

In an embodiment variant in which a plasma applicator comprises an enclosure, the latter can be formed by a biocompatible material, such as medical silicone, a lacquer, an adhesive, a film, a textile, a compression textile or organic material such a gauze, cellulose or cotton.

In an embodiment variant in which a plasma applicator comprises an enclosure, said enclosure of the plasma applicator can comprise at least one layer with liquid-absorbing and/or liquid-removing and/or liquid-distributing materials.

In an embodiment variant in which a plasma applicator comprises an access port, said access port is arranged and embodied in such a way that, during the plasma treatment, a fluid medium can be supplied to or removed from a sealed gas space formed by the enclosure between the electrotechnical core and a surface to be treated. A fluid medium is a gaseous or liquid medium.

In an embodiment variant in which a plasma applicator comprises an enclosure, the enclosure of the plasma applicator can comprise insertion slots which are arranged on the side of the plasma applicator facing away from the surface to be treated and which are embodied such that a power supply unit or an insertion apparatus, complementary to the insertion slots, can be inserted into the insertion slots in order then to be electrically connected to the contacts of the electrotechnical core.

A plasma applicator as described here, or else another plasma applicator, can comprise a barbed hook-occupied part of a hook-and-loop closure on a side of the plasma applicator facing a surface to be treated.

In an embodiment variant in which a plasma applicator comprises an integrated power supply unit, said integrated power supply unit can comprise a power store electrically connected to contacts of the electrotechnical core in order to transmit a voltage signal sufficient to ignite a plasma to the second electrode structure during operation.

In an embodiment variant in which a plasma applicator comprises an integrated power supply unit, the integrated power supply unit can comprise an electrical circuit which is embodied to convert a voltage provided by the energy store into a voltage signal sufficient to ignite a plasma and to transmit said voltage signal to the contact of the second electrode structure.

In an embodiment variant in which a plasma applicator comprises a power receiving apparatus electrically connected to at least the contact of the second electrode structure, the power receiving apparatus can respectively contain one or more receiver coil arrangements. Electrical energy can be transferred from a transmitter coil arrangement of a power dispensing apparatus to the receiver coil arrangements in the plasma applicator by means of electromagnetic induction.

Plasma Treatment

A plasma treatment with a plasma applicator is carried out over a certain treatment time. This treatment time is typically 1 to 10 minutes, preferably 2 minutes. In the case where the plasma is provided in pulsed fashion during the plasma treatment, the summed time duration within which plasma is in fact ignited during plasma treatment corresponds to a comparatively small portion, for example 10%, of the overall time duration of the plasma treatment. Thus, if the overall duration of a plasma treatment is two minutes, for example, and a duty cycle of plasma on to plasma off equals 1 to 9, a plasma is only ignited during a accumulated time duration of 12 seconds. The use of the plasma applicator typically ends with the end of the plasma treatment. Even though the use of a plasma applicator is restricted to the time period of a plasma treatment, a plasma applicator itself can be applied to a surface to be treated both before and after a plasma treatment. By way of example, it can be advantageous for the treatment success if a plasma applicator is applied above a wound even for a certain amount of time after a plasma treatment. By way of example, after a plasma treatment with the duration of one minute, a plasma applicator can remain above the wound for a further five minutes in order thus to improve the treatment success. Wearing a plasma applicator over a relatively long period of time can be advantageous as a plasma applicator covers the surface to be treated and seals off a wound area from recolonization by external microorganisms. If a plasma applicator is worn applied to a wound over a relatively long period of time, e.g., over several days or else several weeks, it is advantageous if a plasma applicator is embodied such that a plasma treatment can be carried out multiple times with the plasma applicator.

A first use of a plasma applicator relates to the first plasma treatment performed with the plasma applicator.

Plasma Applicator

A plasma applicator essentially serves to treat human or animal surfaces. A plasma applicator is particularly suitable for the treatment of wounds, such as chronic wounds and/or wounds after surgery. Moreover, a plasma applicator is also suitable for the treatment of burns, grazes, etc. The use for disinfecting, treating wrinkles, reducing scars and/or other cosmetic treatments is also conceivable. An application in the field of the plasma treatment of technical surfaces is likewise possible. By way of example, technical surfaces could be refined by a plasma treatment. In this case, plasma activation, plasma-assisted chemical vapor deposition and physical vapor deposition should be mentioned as primary active principle.

For the plasma treatment of a human or animal or technical surface, a plasma applicator is preferably attached in such a way that the electrotechnical core is situated on or near the human or animal or technical surface to be treated.

Further Preferred Embodiment Variants of a Plasma Applicator

A plasma applicator can comprise an electrotechnical core and a plug-in apparatus, an enclosure, and an adhesion layer. Then, the plug-in apparatus is preferably electrically connected to at least one electrode structure of the electrotechnical core and suitable for the transmission of voltage signals, preferably with an amplitude ranging from several hundred volts up to 10 kV.

A plasma applicator can have a planar electrotechnical core with at least one electrode structure. Preferably, such a plasma applicator comprises a plug-in apparatus which is electrically conductively connected to the at least one electrode structure in order to transmit a voltage signal to at least this electrode structure.

A plasma applicator can be embodied in such a way that it can flexibly adapt, in particular in interlocking fashion, to any curved surface and can consequently also be used for a plasma treatment for treating areas of skin that are difficult to treat, such as, e.g., the foot.

In such an embodiment variant, the plasma applicator comprises an electrotechnical core, which can be flexibly brought into an appropriate shape.

Alternatively, a plasma applicator can be embodied not in a flexible and pliable form but in a rigid form with a specified shape. In this case, an electrotechnical core can comprise at least one layer or structure which is not flexible and predetermines a rigid shape for the plasma applicator. The predetermined shape is advantageously adapted to the use of the plasma applicator on a specifically shaped surface or a certain body segment. A plasma applicator with a rigid shape can be advantageous, for example, for affixment to soft tissue or soft wound structures.

A plasma applicator can also be embodied to be attached in conical form around a tube or a cable. In this case, a plasma applicator is preferably placed around a tube or a cable such that a sealed gas space with the shape of a cone arises under a plasma applicator, wherein the surface to be treated is located under the cone and a plasma is ignited during use in the sealed gas space between the cone interior and the surface to be treated. Advantageously, it is then not necessary to remove an already laid access to the body to be treated in order to carry out a treatment with a plasma applicator at the access to the body to be treated. If it is known before an access is laid that a treatment with a plasma applicator should take place, it may be advantageous if a plasma applicator has a hole or a slot, e.g., in a cone tip, through which the cable or a tube can be guided. As a result, an access can be laid first and a plasma treatment can occur at a later time without the access having to be removed.

It may be advantageous if a plasma applicator wound dressing area or a plasma applicator itself has a scalable embodiment. A scalable plasma applicator can have a multiplicity of shapes, such as, e.g., polygonal, round, 8-shaped (butterfly), or a shape adapted to specific body structures, e.g., the region under the breast or the heel. In particular, the plasma applicator wound dressing area can be scalable in a range of a few centimeters to many tens of centimeters. Here, it is preferable for a plasma applicator with an area greater than approximately 20 cm×20 cm to have a rectangular or round embodiment. A plasma applicator with a smaller area is particularly suitable for having a shape that is adapted to specific body structures.

Electrotechnical Core

Within the scope of this description, a multilayer system made of adjoining electrode structures and insulation layers, which generates a plasma during operation, is referred to as an electrotechnical core. The arrangement of the structures and layers in such an electrotechnical core can be different in different electrotechnical cores. In various variants of an electrotechnical core, the individual structures and layers can be embodied with a closed surface or a specific geometry.

Various preferred embodiments of an electrotechnical core are described below; these are suitable for an electrotechnical core of a plasma applicator as described here and/or of any other plasma applicator. An electrotechnical core typically has a sequence of insulation layers and electrode structures, which are arranged in a layer stack of adjoining layers and consequently form a multilayer system.

In one embodiment, an electrotechnical core has a planar embodiment and comprises at least one electrode structure, which is preferably driven by a voltage signal during operation, and at least one insulation layer which, during use, is situated between the driven electrode structure and a surface to be treated. Thus, during use, the driven electrode structure is situated on the side of the electrotechnical core facing away from the surface to be treated.

As a rule, an electrotechnical core has a rectangular shape. In various variants, an electrotechnical core has a circular form, an oval form, a hexagonal form or any other polygonal form. In various further variants, an electrotechnical core has a three-dimensional shape, for example the shape of a cylinder or a cuboid. In further variants, the electrotechnical core has a shape that is specifically adapted to a certain body segment (e.g., a heel, a finger, a chest).

In one embodiment, an electrotechnical core comprises at least a first and a second electrode structure, wherein the first and the second electrode structure have a different respective potential which deviates from ground potential in each case (floating electrodes).

In one embodiment, an electrotechnical core comprises, starting from the side facing the surface to be treated, a first insulation layer, which is preferably biocompatible and consequently particularly suitable for treatment of a human or animal surface. A first electrode structure, typically at ground potential, is arranged on the insulation layer. The first electrode structure is followed by a second insulation layer, which is a dielectric layer, to be precise serving for galvanically decoupling the first electrode structure from a second electrode structure arranged on the second insulation layer. During use, the second electrode structure is typically driven with a voltage signal for igniting a plasma.

In one embodiment, an electrotechnical core only comprises a second electrode structure, which is preferably driven by a voltage signal during operation, and a second insulation layer which, during use, is arranged between the second electrode structure and the surface to be treated. During the operation of the electrotechnical core, the counter electrode then is realized, in particular as constituent part of a plasma applicator, by the human or animal or technical body or the surface to be treated itself.

Advantageously, all layers and/or structures of an electrotechnical core are connected to one another in interlocking fashion and without air inclusions, foreign bodies or foreign materials, at least by means of adhesion.

An electrotechnical core can also be provided with holes or passages in one portion, or else these can be distributed over the entire area of said electrotechnical core. The holes or passages can facilitate a media transport through the electrotechnical core, from the side facing a surface to be treated to the side of the plasma applicator facing away from a surface to be treated or, in the reverse direction, from the side facing away from a surface to be treated to the side of the plasma applicator facing a surface to be treated.

In one embodiment variant, in which the electrotechnical core has holes or passages in part or distributed over the entire area of said electrotechnical core, the holes or passages have a diameter ranging between 1 mm and 10 mm.

In one embodiment variant, in which an electrotechnical core has holes or passages in part or distributed over the entire area of said electrotechnical core, the holes or passages are arranged in those regions where there is no electrode structure. Then, the electrode structures are not damaged when drilling or punching the holes.

Preferably, creepage distances are taken into account when arranging holes or passages and designing the diameters thereof in an electrotechnical core with holes or passages in order to facilitate a homogeneous plasma formation on the side of the electrotechnical core facing a surface to be treated.

An electrotechnical core described within the scope of this description can be produced, for example, by means of a dispensing method, by 3D printing or by screen printing or rotary screen printing. Here, one or else more electrode structures are constructed stepby-step within a plurality of process steps. The electrode structures are separated by insulation layers. Dispensing or printing can be carried out alternately with conductive and electrically insulating material. Preferably, an electrotechnical core described within the scope of this description is produced using rotary screen printing. Preferably, at least one insulation layer of the electrotechnical core is formed by a film on which further layers of the electrotechnical core, i.e., electrode structures and/or insulation layers formed by lacquers and/or films, are printed above one another using the rotary screen printing method. These insulation layers of the electrotechnical core, formed by a film and/or lacquer, preferably have a thickness ranging between 10 μm and 500 μm. Preferably, the thickness of an insulation layer is chosen in such a way that there is no electrical breakdown during use between the electrode structures printed on each side of the film or the lacquer. To determine a suitable thickness, it is possible to take account of, inter alia, the breakdown strength of the lacquers or the film, which forms this insulation layer, as the magnitude of the voltage which is applied during the application between the electrode structures printed on the film. An insulation layer formed by a film is preferably free from pores, which are also referred to as pinholes.

In terms of its lateral extent, an electrotechnical core can be greater than an electrode structure of said electrotechnical core. By way of example, an electrotechnical core can have an area of 20 cm×20 cm or else 30 cm×30 cm or even larger, whereas the area of an electrode structure of the electrotechnical core is only 10 cm×10 cm.

An electrotechnical core having an area greater than the electrode structures of the electrotechnical core can be cut to size as desired for a plasma treatment. However, the minimum size is determined by the area of the electrode structures. Particularly in the case of an electrotechnical core whose area is greater than the electrode structures of the electrotechnical core, the electrode structures can be arranged in any desired way in relation to the area of the electrotechnical core within the area.

Electrode Structure

Preferred embodiments of an electrode structure are described below; these are suitable for an electrode structure of an electrotechnical core as described here and/or of any other electrotechnical core. An electrode structure described here is typically formed by an electrically conductive structure. The electrically conductive structure then represents an electrode structure.

An electrode structure of an electrotechnical core or, in the case of a plurality of electrode structures, the electrode structures of an electrotechnical core preferably has/have a planar embodiment and forms/form a layer of an electrotechnical core. An electrode structure can be arranged on or in an electrode carrier. An electrode structure can be formed by a conductive material, in particular with a metal, for example in the form of a thin metal layer, metal film, metal mesh and/or a conductive polymer layer. By way of example, an electrode carrier can be an unprinted film. An electrode structure, or electrode structures, can then be printed onto the unprinted film or an alternative electrode carrier, for example using silver conductive varnish.

In one embodiment, an electrode structure that is 10 µm thick and made of silver conductive varnish, for example, is directly printed onto one of the two sides of an insulation layer, in particular a dielectric layer, such that the dielectric layer itself is the electrode carrier.

An electrode structure of an electrotechnical core can also be formed by electrically conductive threads which are woven into a textile. In this case, the electrode carrier is realized by the textile and the electrode structure is arranged in the electrode carrier. It may also be advantageous to form at least one electrode structure of an electrotechnical core from a conductive, preferably flexible material, such as a conductive plastic, a material enriched with conductive particles, a metallic film or graphite. As a rule, an electrode structure embodied thus does not require an additional electrode carrier. By way of example, an electrode structure embodied thus can be produced by means of a dispensing method.

An electrotechnical core preferably comprises at least two electrode structures, specifically a first and a second electrode structure, wherein the second electrode structure is driven during use by means of a voltage in the form of a voltage signal, applied with respect to reference potential. The first electrode structure is typically grounded. Should an electrotechnical core have a first and a second electrode structure, the first electrode structure typically faces the surface to be treated during use. The distance between the first electrode structure and the second electrode structure is preferably less than 1 mm, in particular less than 200 µm, preferably less than 100 µm. Advantageously, a lower voltage signal is required to ignite a plasma as a result of a small distance.

An electrode structure of an electrotechnical core can be embodied as a layer with a closed area, which extends completely or else only partly over the area of the electrotechnical core. A second and a third electrode structure, in particular, are preferably embodied as such surface electrodes since no electric field lines for generating a plasma should pass through these electrode structures during a plasma treatment. An electrode structure and, in particular, the first electrode structure, which is situated on the side of an electrotechnical core facing the surface to be treated, can also have a specific geometry and can be arranged within a layer. An electrode structure with a specific geometry can have, e.g., a meandering form, a spiral form, be formed by an area with holes, have a square form, a U-shape, an E-shape, an M-shape, an L-shape, a C-shape, an X-shape or an O-shape and can extend laterally within a layer of an electrotechnical core of a plasma applicator. An electrode structure with a specific geometry is preferably formed by regularly arranged electrode sections, which preferably form a regular pattern.

In one embodiment of an electrotechnical core with a plurality of electrode structures, a first and a second electrode structure, in particular, have the same specific geometry and their electrode sections are arranged in different layers of an electrotechnical core with an offset with a defined overlap with respect to one another. In particular, at least one insulation layer, e.g., in the form of a film, an adhesive or a lacquer, is situated between two electrode structures. It can also be advantageous if the plurality of electrode structures of an electrotechnical core have different geometries.

The overlap of the electrode sections can have significant influence on the capacitance of an electrotechnical core and the magnitude of the electric field strength generated by the electrotechnical core during operation. If the electrode sections of a first and a second electrode structure are arranged congruent to one another such that the electrode sections completely overlap, the field strength is typically small and the capacitance is at a maximum. What typically applies is that the capacitance is greatest when the electrode sections completely overlap while the capacitance decreases with reduced overlap of the electrode sections. In general, a high electric field strength with a small distance between the two electrode structures is advantageous for igniting a plasma. As the distance increases, so does the amplitude of the voltage signal required to ignite a plasma. However, a comparatively small capacitance is advantageous since an electrotechnical core then reacts more quickly and distortions in the voltage signal are weak on account of a small capacitive component.

In an electrotechnical core of a plasma applicator, a plurality of electrode structures can also be arranged within a layer of said electrotechnical core. Each of the electrode structures represents an individual electrode structure per se, which, in terms of its lateral extent, only extends over a part of the area of an electrotechnical core. Preferably, the plurality of electrode structures in this layer are distributed uniformly over the area of an electrotechnical core, i.e., over the area of the wound dressing. The plurality of electrode structures within a layer can all be electrically interconnected. It is also conceivable that only certain individual electrode structures within the layer are electrically interconnected such that groups of electrically interconnected electrode structures are formed. Moreover, it can be advantageous if electrode structures within a layer are not electrically interconnected and each form electrically independent treatment regions. The plurality of electrode structures within a layer can be driven with a time offset, i.e., in cascaded fashion. Advantageously, cascaded driving can lead to reduction of a power uptake per time interval and/or to a reduction in the treatment time.

The plurality of electrode structures within a layer of an electrotechnical core of a plasma applicator can be formed from the aforementioned materials and in the aforementioned shapes, which were specified above in relation to the above-described electrode structures.

The electrode structures described herein preferably have a thickness of a few μm up to several hundred μm.

If an electrode structure is not formed over the whole area, i.e., not as a surface electrode, but instead as one of the above-described special geometries, the thickness and the width of the electrode sections of the electrode structure with one of the special geometries are preferably chosen in such a way that the electrode structure is not destroyed by the thermal load during the operation of a plasma applicator or that the plasma applicator does not exceed a temperature of 40° C. during operation. Unless, of course, single use of an electrotechnical core should be ensured.

The material property decisive in this case is the electrical resistance or the impedance which, depending on material and geometry, should not exceed a certain value of, as a rule, a few ohm. Depending on the material employed and its conductance, the electrode sections of such an electrode structure advantageously have an appropriately chosen cross section. Electrode sections with a width of 5 mm and a thickness of 14 μm were found to be advantageous. However, in various variants, these values can deviate from the values specified and nevertheless lead to material properties that are advantageous for specific applications. By way of example, for some applications it could be advantageous if the electrode sections of an electrode structure have a width of 1 mm and a thickness of 70 μm. By way of example, for other applications it could be advantageous if the electrode sections of an electrode structure have a width of 10 mm and a thickness of 7 μm.

In one embodiment, an electrode structure is formed from long polymer snakes. The interior of a polymer snake produced thus preferably comprises a conductive polymer, such as silicone enriched with conductive particles such as carbon or carbon nanotubes. Preferably, a biocompatible material (e.g., silicone) is printed or dispensed around the electrode structure. Advantageously, the electrode structure produced thus can have a multiplicity of different shapes and need not necessarily be flat.

In one embodiment, an electrode structure is formed by a wire mesh, a wire fabric or a wire netting. Such a wire mesh, wire fabric or wire netting can be formed by a single insulated wire or a plurality of insulated wires. If the wires are insulated, a separate insulation layer in which the wires are embedded becomes obsolete. A corresponding wire mesh, wire fabric or wire netting thus already represents a comparatively simple electrotechnical core.

Thus, a comparatively simple plasma source can be realized by a wire mesh, wire fabric or wire netting. If a wire mesh, wire fabric or wire netting is formed by a single wire, a counter electrode is realized during use by a surface to be treated itself. If a wire mesh, wire fabric or wire netting is formed by a plurality of wires, at least one wire can be driven by a voltage signal during use and at least one further wire can be grounded; the latter then represents a counter electrode.

A wire of a wire mesh, wire fabric or wire netting represents a comparatively simple electrical conductor. A wire mesh, wire fabric or wire netting can also be formed by a simple electrical conductor in the form of at least one ribbon cable. A ribbon cable within this meaning can have a square or rectangular cross section. A simple electrical conductor preferably has an insulation sheath.

It is also conceivable for a plasma source to be formed by a single insulated electrical conductor, for example an insulated wire, without the latter being arranged in a comparatively complicated structure such as a fabric or a mesh. If an electrical conductor, e.g., an insulated wire, is arranged above a surface to be treated and a current is applied thereto, the surface to be treated can act as a counter electrode and can ignite a plasma between the surface to be treated and the insulated wire. Thus, in this case, an insulated wire is placed over or on a surface to be treated, e.g., as a loop or in one dimension.

Insulation Layer

Preferred embodiments of an insulation layer are described below; within the scope of this description, said insulation layer is also referred to as a dielectric layer and it is suitable as a constituent part of an electrotechnical core as described herein and/or of any other electrotechnical core. An insulation layer as described herein can be formed by an electrically insulating structure. The electrically insulating structure then represents an insulation layer.

To prevent a current flow between an electrode structure driven during use and a possible further electrode structure at ground potential, at least one insulation layer is preferably situated in an electrotechnical core between the respective electrode structures or the at least one electrode structure driven by a voltage signal during operation and a human or animal or technical surface to be treated.

An insulation layer can consist of plastic or ceramic or both, for example. An insulation layer preferably has a thickness between a few μm and a few 100 μm. Like in the case of an electrode structure, the choice of the thickness of an insulation layer depends on the electrical material constants, in particular the dielectric constant and the breakdown strength.

It can be advantageous for the thickness of an insulation layer to be chosen to be comparatively thin and, for example, lie in the region of 50 μm. As a rule, a low thickness leads to a lower amplitude of a voltage signal being required to ignite a plasma. Moreover, a low thickness can be advantageous to ensure a high flexibility of the plasma applicator.

Depending on use, e.g., in the case of a plasma applicator with a rigid form, a thickness of 200 μm and more can be advantageous. Particularly when using inflexible materials, such as ceramics that cannot be produced to be arbitrarily thin, a thickness of at least 200 μm can be advantageous.

Preferably, an insulation layer has a thickness that is less than 1 mm, in particular less than 200 μm, preferably less than 100 μm.

Preferably, an insulation layer is embodied as a whole-area layer.

Preferably, an insulation layer is pore-free, i.e., there are no or very few holes or cavities present, and so no discharge channels form through the insulation layer. Preferably, an insulation layer has a dielectric strength of at least 5 kV per mm thickness. Moreover, it is preferable for the lateral extent of an insulation layer to correspond to the dimension of an electrode structure in an electrotechnical core plus an edge projecting therebeyond, wherein the edge is preferably dimensioned in such a way that it at least covers the length of the creepage distances.

In one embodiment, the lateral extent of an insulation layer is chosen in such a way that there is no arc discharge between a second electrode structure, which is driven during use, and a first and/or third electrode structure at reference potential or a surface to be treated.

Advantageously, creepage distances can be undercut by at least partly enclosing an electrotechnical core with an enclosure. In one embodiment in which an electrotechnical core is at least partly enclosed by an enclosure, a lateral extent of an insulation layer can be dimensioned on the basis of the employed enclosure in such a way that an edge of the insulation layer projecting beyond an electrode structure is dimensioned to be smaller than a creepage distance which would specify the amplitude of a voltage signal required to ignite a plasma per se.

A first insulation layer which directly faces a surface to be treated during use preferably comprises a biocompatible material such as lacquer, silicone, PU or coatings. Coatings can be applied, for example, using wet chemical processes, plasma-assisted chemical vapor deposition (PACVD), chemical vapor deposition (CVD), anodizing processes or electroplating.

Plug-in Apparatus

Preferred embodiments of a plug-in apparatus are described below. A plug-in apparatus as described herein can be a constituent part of a plasma applicator as described herein and/or of any other plasma applicator, and it serves to connect an electrotechnical core of a plasma applicator, in particular, to a power supply unit by way of establishing a connection to an insertion apparatus with a complementary embodiment. Since a plug-in apparatus is a constituent part of a plasma applicator, it represents an applicator plug-in contact apparatus.

A plug-in apparatus is preferably securely connected to an electrotechnical core and, in particular, to a second electrode structure which is driven during use and—if present—to the grounded electrode structures of an electrotechnical core. Preferably, a plug-in apparatus is suitable for transmitting a voltage signal in the kV-range, particularly in the range from several 100 volts to 10 kV, to a second electrode structure.

A plug-in apparatus preferably has at least one electrical conductor track, which is an electrically conductive conductor structure and which leads to at least one electrode structure. Thus, a conductor track is arranged in electrically conductive contact with an electrode structure, preferably at a longitudinal side of the corresponding electrode structure, and it preferably extends in perpendicular fashion in relation to the longitudinal side of the corresponding electrode structure in a common plane with the electrode structure. If an electrotechnical core comprises a plurality of electrode structures, at least one conductor track, as a rule, is arranged at each of the electrode structures. To electrically insulate the conductor tracks from one another, at least one insulating tab is arranged between the conductor tracks in each case. Preferably, it is securely connected to an insulation layer and formed by the same electrically insulating material as the insulation layer. In particular, the tab can be an integral constituent part of the respective insulation layer.

A plug-in apparatus can be securely connected to an electrotechnical core by means of, e.g., lamination, laminating, adhesion, soldering or an alternative material-connecting method. A conductor track of a plug-in apparatus preferably has a comparable thickness as an electrode structure of a corresponding electrotechnical core and preferably consists of the same material or the same materials as well, and it preferably has a conductance of a comparable order of magnitude as this electrode structure.

Preferably, an electrotechnical core and a plug-in apparatus are produced in a common manufacturing process. Then, for example, a conductor track and an electrode structure electrically connected to said conductor track are co-produced simultaneously and directly as an electrode structure with the conductor track in a manufacturing step. Then, for example, an insulation layer and a tab are produced simultaneously and directly as an insulation layer with an integral tab in a further manufacturing step, and these are applied together to an electrode structure with a conductor track. Thus, an electrotechnical core with a plug-in apparatus is produced as a common product in such a manufacturing process. An electrode structure with a conductor track then consists of the same material and has a homogeneous thickness. Likewise, an insulation layer with an integrally formed tab consists of one material and has the same thickness everywhere. Advantageously, an electrotechnical core and a plug-in apparatus then need not be produced in separate manufacturing processes and be subsequently connected to one another.

Such an electrotechnical core with a plug-in apparatus thus deviates from the aforementioned basic shapes of an electrotechnical core without a plug-in apparatus to the extent that the basic shape is complemented by, e.g., a tab-shaped plug-in apparatus. Here, the electrode structures and insulation layers of the electrotechnical core are preferably extended to this tab.

A perforation can be provided between the electrotechnical core and plug-in apparatus at the transition from the plug-in apparatus to electrotechnical core or at that position where a plug-in apparatus is connected to the electrotechnical core. The function of the perforation lies in the reduction of the strength between the plug-in apparatus and electrotechnical core. The perforation represents an intended breaking point. Following a plasma treatment, the plug-in apparatus can be torn off or removed from the electrotechnical core at this perforation. As a result, a plasma applicator can remain on a surface to be treated for a relatively long period of time, from days to weeks, independently of a power supply unit since the plug-in apparatus, no longer needed, can be removed.

The plug-in apparatus preferably has the form of a chip card, i.e., a length of approximately 5 cm to 16 cm, a width of 1 cm to 3 cm, and a height between approximately 0.2 mm and 1 mm. The dimensions of a plug-in apparatus can also deviate from the specified values and are dimensioned on the basis of the length of creepage distances, depending on the amplitude of a voltage signal for igniting a plasma. Advantageously, the lateral extent of a plug-in apparatus is a chosen in such a way that there is no arc discharge between the second electrode structure, which is driven during use, and a further electrode structure at reference potential, for example a first or third electrode structure, or a surface to be treated.

In a preferred configuration, a plug-in apparatus or an insertion apparatus is embodied as a plug-in apparatus with a reinforcement, with a height of between 0.2 mm and 1.5 cm, with a length of between 5 cm and 20 cm, and with a width of between 1 cm and 3 cm. A corresponding insertion apparatus has a complementary embodiment for the purposes of receiving the plug. As a result of the chip card-like form of the plug-in apparatus, i.e., a small height and a comparatively long length, it is possible to maintain creepage distances, in particular, in such a way that no partial discharges arise within the plugged together plug-in apparatus and insertion apparatus. The specified dimensions for the length, width, and the height can also advantageously be realized independently of one another so that the creepage distances continue to be maintained. Furthermore, it is preferable for the insertion apparatus to comprise an insulation sheath for reducing the emitted electromagnetic waves, taking into account the creepage distance. Using the specified dimensions, it is possible, in particular, to realize creepage distances between applied conductor tracks of a plurality of centimeters. The decisive factor here is the applied voltage for generating the plasma. Typically, the higher the intended voltage to be applied for the purposes of generating a plasma, the greater the creepage distances must be as well. The properties, in particular the dielectric properties, of the material employed and the degree of contamination of the material employed are also decisive. Even in the case of a contaminated surface of the material employed, creepage distances must typically be designed to be comparatively large.

A plug-in apparatus with a reinforcement in a chip card form preferably has a permanent connection to an electrotechnical core, realizable, for example, by laminating, adhesive bonding, soldering or as a direct extension of the electrotechnical core in the form of a tab. The plug-in apparatus is preferably partly enclosed by the material of an enclosure of a plasma applicator, for example by virtue of being overmolded with silicone. Furthermore, the plug-in apparatus can comprise printed or vapor-deposited or etched conductor tracks.

A plug-in apparatus can furthermore comprise a reinforcement which is preferably applied above and/or below the tab and which mechanically strengthens the plug-in apparatus. The conductor tracks can also be embodied as a coil wire with an insulating sheath of the wire. Optionally, a plug-in apparatus can also have a data line, e.g., as a conductor track or as a ribbon cable. By way of example, it may be advantageous to install a memory in a plasma applicator or in a corresponding coupling or in a power supply unit in order to collect data about the use of the plasma applicator.

Using an appropriate data cable with coupling, an RFID transponder or a nonvolatile electronic memory chip, which is situated in a plug-in apparatus, for example, can also be read by a reader integrated in an insertion apparatus with a complementary embodiment in order to ensure single use.

Advantageously, data in respect of a plasma applicator itself can be stored in an appropriate memory chip. If the plasma applicator with a memory chip is connected to a power supply unit via an appropriate a data cable, the power supply unit is able to read the data stored and able to automatically provide a certain voltage, a certain pulse pattern, a certain treatment time or further treatment parameters for operating the specific plasma applicator. Preferably, the parameters employed are stored in a targeted fashion in the power supply unit for different plasma applicator shapes and sizes or for a specific set-up of the electrotechnical core of a plasma applicator, and are retrieved and used by the power supply unit in accordance with the connected plasma applicator.

Preferably, a plug-in apparatus is attached to a longitudinal side of an electrotechnical core and electrically connected to at least one electrode structure of the electrotechnical core. It is also conceivable for a plug-in apparatus to be applied in the form of an insertion slot to the upper side of an electrotechnical core, i.e., that side of an electrotechnical core facing away from a side to be treated, and to be connected to at least one electrode structure.

Preferably, the plug-in apparatus is embodied as a plug-in apparatus with a reinforcement with a height of between 0.5 mm and 1.5 cm, a length of between 5 cm and 20 cm, and a width of between 1 cm and 3 cm, and a corresponding insertion apparatus, complementary to the plug-in apparatus, is embodied as a receiving socket for receiving the plug-in apparatus.

By way of example, in order to transmit a voltage signal to a second electrode structure by means of a power supply unit, an insertion apparatus, complementary to a plug-in apparatus, can be connected to the plug-in apparatus, for example. The insertion apparatus can be connected to a cable which is connected to a predominantly stationary power supply unit. By way of example, a corresponding power supply unit can be a high-voltage generator with a control unit.

Single Use

Various means and features that can ensure single use of an electrotechnical core and, in particular, of a plasma applicator are described below. Preferably, the means and features that ensure single use are realized as a constituent part of a plasma applicator, in particular as a constituent part of a plug-in apparatus as described here and/or of any other plug-in apparatus or as a constituent part of an electrotechnical core as described here and/or of any other electrotechnical core.

In one embodiment of a plasma applicator, an electrotechnical core has at least one feature which changes in such a way as a consequence of a first use that it is no longer possible to form a sufficiently strong electric field for igniting a plasma between the electrode structure driven during use and the grounded electrode structure. As a result, single use of a plasma applicator is advantageously ensured. A feature of an electrotechnical core that ensures single use of the plasma applicator can be, for example, a self-destructing apparatus such as an electrical fuse. By way of example, such an electrical fuse can be provided by a taper of an electrode section of an electrode structure in the electrotechnical core, which is destroyed at the end of the treatment by a high current pulse provided at that point as it has a higher resistance than the remainder of the electrode structure and therefore heats more quickly. Preferably, such a taper is situated in the electrode structure that is driven during use.

The following means and features which ensure single use of a plasma applicator, described in relation to a plug-in apparatus, can also be realized as features of an electrode structure, in particular as a constituent part of an electrode section of an electrode structure of an electrotechnical core. Preferably, an electrode structure driven during operation by a voltage signal has at least one feature or means as described in relation to a plug-in apparatus in order to ensure single use of an electrotechnical core, in particular as a constituent part of a plasma applicator.

In one embodiment of a plasma applicator, a plug-in apparatus has at least one feature which changes in such a way as a consequence of a first use that a plug-in apparatus can no longer transmit a voltage signal sufficient to ignite a plasma to an electrode structure of an electrotechnical core any more or that the electrotechnical core can no longer form a sufficiently strong electric field to ignite a plasma. As a result, single use of a plasma applicator is advantageously ensured. A feature of a plug-in apparatus that ensures single use of a plasma applicator can be, for example, a self-destructing apparatus such as an electrical fuse. By way of example, such an electrical fuse can be provided by a taper of a conductor track, which is destroyed at the end of the treatment by a high current pulse provided at that point as it has a higher resistance than the remainder of the conductor track and therefore heats more quickly.

In one embodiment, a plasma applicator for generating a cold plasma for the treatment of human or animal or technical surfaces comprises a planar electrotechnical core with at least one electrode structure and an insulation layer. The plasma applicator furthermore comprises a plug-in apparatus which is electrically conductively connected to the at least one electrode structure in order to transmit a voltage signal to at least this electrode structure. The plug-in apparatus is preferably embodied to ensure single use of the plasma applicator by virtue of the plug-in apparatus having at least one mechanical and/or electrical component which is designed in such a way that, as a consequence of a first use of the plasma applicator, it changes its technical properties in such a way that the plug-in apparatus, after first use, can no longer transmit a voltage signal sufficient to ignite a plasma to the at least one electrode structure.

Ensuring single use can thus be realized, for example, by virtue of an electrical component being destroyed on account of the current flow as a consequence of the first use or by virtue of a mechanical or electrical component being destroyed when mechanically separating the plug-in apparatus from a complementary insertion apparatus.

The mechanical and/or electrical component changing its structure in such a way as a consequence of a first use of the plasma applicator that the plug-in apparatus can no longer transmit a voltage signal sufficient to ignite a plasma to the at least one electrode structure after first use ensures that the plasma applicator can only be used once. Advantageously, this can prevent multiple use of an already used plasma applicator, which no longer meets certain requirements in respect of hygiene as a consequence of the first use. Accordingly, a wound only being treated by an unused plasma applicator is ensured.

The use of a plasma applicator relates to a plasma treatment being carried out. That is to say, a voltage signal is initially provided with the aid of a power supply unit, said voltage signal being transmitted to an electrode structure for the purposes of igniting a plasma.

A corresponding feature of single use can also be realized by a chemical reaction with atmospheric oxygen or nitrogen or an electrochemical reaction which is induced by an applied voltage signal during a plasma treatment. By way of example, an applied voltage signal can trigger an electrochemical reaction in the conductor tracks, consisting of, e.g., silver conductive varnish, of a plug-in apparatus, which accelerates an oxidation of a conductor track, in particular at exposed contact faces, and consequently increases the resistance at this point. A voltage signal for operating a plasma applicator is significantly changed as a result of an increased or reduced resistance. This change can be detected in a power supply unit and a release of the voltage signal can consequently be prevented. Thus, in general, it is conceivable for, e.g., an oxidation or nitriding of the conductor track in air to reduce its conductivity and thereby alter a voltage signal in such a way in terms of, e.g., amplitude, frequency and/or signal profile (e.g., as a result of the fact that a pure sinusoidal oscillation is no longer present) that it can be detected as a fault signal by a power supply unit and leads to an automatic termination of the energy output by the power supply unit. A further option consists of exploiting an electrochemical reaction, induced by a voltage signal, for changing the conductor track of the plug-in apparatus, which leads to the voltage signal being changed in such a way in terms of, e.g., amplitude, frequency and/or signal profile (e.g., as a result of the fact that a pure sinusoidal oscillation is no longer present) that it can be detected as a fault signal by a power supply unit and leads to an automatic termination of the energy output by the power supply unit.

A plug-in apparatus is preferably embodied in such a way that it can be connected in electrically conductive and mechanical fashion to an insertion apparatus which has a complementary embodiment to the plug-in apparatus. The mechanical component of the plug-in apparatus can be embodied in such a way that it changes its structure in such a way during the mechanical separation of the plug-in apparatus from the insertion apparatus that, following the separation, it is no longer possible to electrically conductively connect the plug-in apparatus to the insertion apparatus for the purposes of transferring a high voltage.

Such a mechanical change can comprise the breaking off of terminals of a clamping contact or of locking elements and/or a scratching and/or cutting of the conductor structure of the plug-in apparatus.

A plug-in apparatus can comprise at least one locking element which is embodied and arranged in such a way that it locks with the insertion apparatus when the plug-in apparatus is connected to said insertion apparatus and it becomes irreversibly unusable when the plug-in apparatus is separated from an insertion apparatus.

A mechanically stable connection is preferably established by connecting an insertion apparatus to the plug-in apparatus, which can only be separated again by an active application of force by a person. The force required to this end typically lies between 5 and 50 N, preferably between 10 and 30 N. So that a mechanical component of the plug-in apparatus changes its structure in such a way as a consequence of the first use of the plasma applicator that the electrotechnical core can no longer form a sufficiently strong electric field for igniting a plasma, provision can be made, for example, for locking elements of the plug-in apparatus to break off or be destroyed. Accordingly, it is then no longer possible to establish a stable mechanical connection between the plug-in apparatus and the insertion apparatus. Consequently, following separation, i.e., as a consequence of first-time use, the electrotechnical core connected to the plug-in apparatus is no longer able to form a sufficiently strong electric field to ignite a plasma.

In one embodiment of a plasma applicator, a plug-in apparatus or an electrotechnical core comprises an electrical component which changes its structure in such a way as a consequence of a first-time use of a plasma applicator that the plug-in apparatus or the electrotechnical core can no longer generate an electric field sufficient to ignite a plasma after first-time use. By way of example, the plug-in apparatus can comprise a conductor track which is intended to transmit a voltage signal to an electrode structure and which is destroyed by a high current pulse at the end of the first time use of a plasma applicator. Thereafter, the plug-in apparatus can no longer transmit a voltage signal sufficient to ignite a plasma to an electrode structure.

In one embodiment of a plasma applicator, a second electrode structure of an electrotechnical core comprises a region which is destroyed by a high current pulse at the end of a first time use of a plasma applicator. Thereafter, the electrotechnical core can no longer form a sufficiently strong electric field to ignite a plasma.

In one embodiment, a plasma applicator comprises a plug-in apparatus which can be electrically conductively and mechanically connected to an insertion apparatus with a complementary embodiment to the plug-in apparatus, wherein the mechanical component of the plug-in apparatus changes its technical properties in such a way during the mechanical separation of the plug-in apparatus from the insertion apparatus that, following the separation, it is no longer possible to electrically conductively bring together the plug-in apparatus and the insertion apparatus for the purposes of transmitting a voltage signal sufficient to ignite a plasma. Changing the technical properties of the mechanical component preferably comprises a breaking off of terminals of a clamping contact, scratching or cutting.

Preferably, a plug-in apparatus or an electrotechnical core of a plasma applicator are designed in such a way that they are changed in such a way as a consequence of a current flow at the end of the first time use that the plug-in apparatus, after first time use, can no longer transmit a voltage signal sufficient to ignite a plasma to an electrode structure of the electrotechnical core.

A power supply unit can be embodied to provide a high current pulse at the end of a plasma treatment, which current pulse changes or destroys parts of a conductor track in the plug-in apparatus such that, when a power supply is connected anew, it is no longer possible to transmit a voltage signal sufficient to ignite a plasma to the at least one electrode structure in the electrotechnical core. Preferably, the power supply unit combined with the plasma applicator automatically emits an excessive current pulse at the end of the plasma treatment, preferably for much less than one second, preferably in the millisecond or even microsecond range. To ensure that corresponding parts of a conductor track in the plug-in apparatus are destroyed, the current intensity of the current pulse provided is preferably chosen in such a way that the melting point of the conductor track of the plug-in apparatus is significantly exceeded and the conductor track is destroyed. Advantageously, this ensures single use of a plasma applicator.

Preferably, a plug-in apparatus has a conductor track which leads from a contact face in the plug-in apparatus to at least one electrode structure, wherein this conductor track can be destroyed at at least one point by a current with a current intensity that is greater than a current intensity occurring during the operation for generating the plasma. The at least one point preferably has a higher electrical resistance than the remainder of the conductor track and/or the at least one point has a lower thermal stability than the remainder the conductor track and/or the at least one point has a taper with a smaller conductor track cross section than the remainder of the conductor track. A corresponding conductor track preferably consists of, e.g., silver conductive varnish, metal, metal film, a polymer enriched with conductive particles or a conductive polymer.

In particular, the at least one point has a higher electrical resistance than the remainder of the conductor track. As an alternative or in addition thereto, the at least one point can also have a lower thermal stability than the remainder of the conductor track. As yet a further alternative or in addition thereto, the at least one point can also have a taper with a smaller cross section than the remainder of the conductor track. At the point of the conductor track with a higher electrical resistance than in the remainder of the conductor track, the increased current intensity leads to strong heating of the conductor track and consequently to a destruction of the conductor track. This ensures that the plasma applicator can only be used once.

Single use of a plasma applicator with a plug-in apparatus with a corresponding conductor track can also be realized by a point of the conductor track with the same resistance as the remainder of the conductor track but with a lower thermal stability. If a current pulse with an increased current intensity is provided, preferably at the end of the plasma treatment with a duration significantly below approximately 1 second, the thermal load on the conductor track is increased. The point with a lower thermal stability can be embodied in such a way that it melts as a result of the current pulse provided, as a result of which single use of a plasma applicator is ensured.

Single use of a plasma applicator can also be ensured by a taper of the corresponding conductor track. As a result of the taper, the resistance at this point is increased such that the elevated current intensity provided at the end of the treatment leads to the conductor track melting at this point. The overvoltage thus leads to temperature increase at the point with the taper and consequently to the melting of the conductor track. By way of example, the dimension of the conductor track can be calculated in accordance with the material employed in such a way that, given a certain current flow over a defined period of time, the material increases to a temperature that preferably lies significantly above the melting point of the material such that the conductor track melts at this point.

Preferably, the conductor track has a height that is less than 0.8 mm and a width that is less than 1 cm. Such conductor tracks can be realized by means of, e.g., screen printing with a conductive material, targeted etching of conductor tracks or printed conductor tracks (e.g., printed electronics).

A plug-in apparatus can have a nonvolatile electronic memory chip which can be read by a corresponding contact in the insertion apparatus when the insertion apparatus and the plug-in apparatus are interconnected, wherein the nonvolatile electronic memory chip provides information that prompts the connected power supply unit to prevent power being output to a connected plasma application during operation.

A plug-in apparatus comprises an RFID transponder in one embodiment. The RFID transponder is embodied in such a way that it can be read by a reader integrated in an insertion apparatus when the corresponding insertion apparatus and the plug-in apparatus are interconnected.

The RFID transponder preferably provides information which prevents the release of a high voltage by a power supply unit. It is conceivable for an identity to be assigned to a plasma applicator, which identity can be read by a reader integrated in an insertion apparatus. By way of example, in a controller of a power supply unit, unique and individual identifiers for each plasma applicator that was connected to the power supply unit can be stored. Thus, a reader can identify whether or not a plasma applicator has already been used. As an alternative or in addition thereto, provision can also be made of a read/write device in order to change or set a value stored in the RFID transponder—e.g., a flag—which indicates that the plasma applicator has been used.

In one embodiment, a plasma applicator is embodied to store a special code or hash value in a memory. Preferably, a power supply unit is embodied to set certain values for treatment parameters on the basis of a read code or hash value and to output during operation an appropriate voltage signal to a plasma applicator connected to the power supply unit. Preferably, a power supply unit is embodied to read values of the treatment parameters for the size of a plasma applicator or in relation to the type of disease that should be treated by the connected plasma applicator from a list stored in the power supply unit. Preferably, a power supply unit is embodied to check whether a read plasma applicator has already been used or whether it is suitable for a certain plasma treatment. Following a plasma treatment, a read/write device is preferably embodied either to destroy the chip with the value or to write a new value to memory. The new value contains, e.g., only zeros such that the specific plasma applicator can no longer be used for a plasma treatment since the connected power supply unit is preferably embodied to refuse the release of a voltage signal should invalid numbers be used.

An RFID transponder can also be integrated not in a plug-in apparatus but in the remaining plasma applicator.

In one configuration, a plug-in apparatus has a nonvolatile electronic memory chip, e.g., an EPROM (erasable programmable read-only memory), which can be read by a corresponding contact in the insertion apparatus when the insertion apparatus and the plug-in apparatus are interconnected. Similar to the case of an RFID transponder, a value can be written to the nonvolatile electronic memory chip upon first use, said value indicating during the subsequent readout that the plasma applicator has already been used. A release of a high voltage by a power supply unit can no longer be implemented after the first use. In conjunction with a corresponding controller this can prevent multiple use.

Rather than in a plug-in apparatus, a nonvolatile electronic memory chip can also be integrated in the remaining plasma applicator.

Insertion Apparatus

Embodiments of an insertion apparatus are described below. An insertion apparatus represents a unit complementary to a plug-in apparatus and it is embodied to establish a secure mechanical and electrical connection with a plug-in apparatus.

Accordingly, an insertion apparatus represents a complementary plug-in contact apparatus with an embodiment that is complementary to a plug-in apparatus. Thus, an insertion apparatus represents a counterpart to a plug-in apparatus. An insertion apparatus can preferably be arranged at an end of a cable or be part of a power supply unit.

Preferably, provision is made for an insertion apparatus which is embodied to transmit a voltage signal to a plug-in apparatus, plugged together with the insertion apparatus, of an electrotechnical core, in particular a plasma applicator.

An insertion apparatus is preferably embodied in such a way that it can be connected in electrically conductive fashion to a complementary plug-in apparatus. By bringing together a plug-in apparatus and an insertion apparatus, an electrical and a mechanical connection are established at the same time. Here, the conductor tracks of the insertion apparatus and the plug-in apparatus are electrically insulated to the outside in the brought-together state.

An insertion apparatus can be connected to a cable. By way of the cable, a plasma applicator connected to a corresponding insertion apparatus can be connected to a predominantly stationary power supply unit. A predominantly stationary power supply unit can also comprise a controller. An insertion apparatus can be separated from the plug-in apparatus at any time, and so, together with a plasma applicator, the user of said plasma applicator can move independently of the power supply unit and the insertion apparatus. In the case where a plug-in apparatus is embodied in the form of a plug, in particular in the form of a chip card, an insertion apparatus is embodied as a corresponding coupling for receiving the plug-in apparatus.

An insertion apparatus can also be embodied as part of a mobile power supply unit, which preferably comprises an energy store, for example a battery, an accumulator or a capacitor. Then, an insertion apparatus is typically electrically connected to an energy store in order to provide electrical power provided by the energy store to an electrotechnical core—when said insertion apparatus is connected to a plug-in apparatus. Advantageously, an insertion apparatus need not be connected to a comparatively long cable in that case in order to connect the insertion apparatus to a predominantly stationary power supply unit.

To supply a plasma applicator with a voltage signal, an insertion apparatus of a mobile power supply unit can be connected to a plug-in apparatus and can be separated from the latter again following a plasma treatment. In the brought-together state, a DC voltage provided by an energy store is then transformed by means of an electrical circuit integrated in the mobile power supply unit into a voltage signal sufficient to ignite the plasma and said sufficient voltage signal is transferred to the plug-in apparatus via the insertion apparatus.

Since a battery or an accumulator typically provides a DC voltage of a few volt, an electrical circuit can be provided in a plasma applicator or in a mobile power supply unit, said electrical circuit transforming the DC voltage provided by the battery or the accumulator of the compact and mobile power supply unit into a voltage signal sufficient to ignite a plasma, which sufficient voltage signal is transferred to at least one electrode structure for the purposes of igniting a plasma. Advantageously, a mobile power supply unit forms a small and compact unit in comparison with the plasma applicator, said small and compact unit being able to be carried along over long distances and for relatively long periods of time of a plurality of weeks, even if it is connected to the plasma applicator.

Thus, in the brought-together state, the plasma applicator and the mobile power supply unit, which is comparatively small in comparison with the plasma applicator, form a unit that can easily be carried by a patient during a plasma treatment. Thus, a mobile power supply unit represents an autonomous power supply which does not make it necessary to connect a power supply unit predominantly used in stationary fashion, such as a high-voltage generator, to the plasma applicator via a cable and an insertion apparatus in order to transmit a voltage signal to at least one electrode structure and ignite a plasma.

This gives a user of a mobile power supply unit independence from a power supply unit predominantly used in stationary fashion, which is large in comparison with a mobile power supply unit, connected to a local power supply such as a high-voltage generator, and typically only transported over short distances, e.g., within a hospital. In particular, a user of a mobile power supply unit can make a decision themselves as to when and where they would like to carry out a plasma treatment. A user of a mobile power supply unit is accordingly independent of local infrastructure, such as the power grid and available power sockets. This is particularly advantageous if a user is, for a relatively long period of time of a number of weeks, in an area where the closest hospital is far away and moreover only little luggage can be carried along, or, in general, for the home care sector, i.e., the application outside of a clinic or in a non-clinical setting.

A voltage signal provided by a mobile power supply unit can be transferred from an insertion apparatus to a plug-in apparatus, for example by establishing galvanic coupling.

In a further embodiment, a plasma applicator has no plug-in apparatus and accordingly cannot be connected by means of an insertion apparatus to a predominantly stationary or a mobile power supply unit. To provide a voltage signal, an energy store, e.g., a battery or an accumulator, can be integrated into the plasma applicator itself and can be electrically connected to at least one electrode structure of an electrotechnical core by way of a suitable electrical circuit, e.g., a blocking oscillator circuit, for the purposes of generating a voltage sufficient to ignite a plasma.

Should an accumulator or a capacitor be integrated in a plasma applicator with a plug-in apparatus, the accumulator or the capacitor can be charged by connecting the plug-in apparatus to a power supply. Here, too, the accumulator or the capacitor is electrically connected to at least one electrode structure of an electrotechnical core via a suitable electrical circuit, e.g., a blocking oscillator circuit, for the purposes of generating a voltage sufficient to ignite a plasma. By switching a switching contact, the energy stored in the accumulator or the capacitor can then be output to at least one electrode structure at a later time.

Inductive Energy Transfer

In one embodiment, a plasma applicator does not comprise a plug-in apparatus but a power receiving apparatus, which contains one or more receiver coil arrangements in each case. By means of a mobile power supply unit containing one or more transmitter coil arrangements, electrical energy can be transferred from the transmitter coil arrangements in the mobile power supply unit to the receiver coil arrangements in the plasma applicator by way of electromagnetic induction. It is likewise conceivable for a transmitter coil arrangement to be contained in a power dispensing apparatus. The power dispensing apparatus is preferably connected to a cable and can be connected to a stationary power supply unit. The electrical energy provided by a stationary power supply unit can be transferred from a transmitter coil arrangement in the power dispensing apparatus to a receiver coil arrangement in the plasma applicator by means of electromagnetic induction. Advantageously, the energy dispensing apparatus can be completely enclosed by, e.g., a silicone or a lacquer in this embodiment and it is possible to dispense with freely accessible electrical contacts, both in or on the energy dispensing apparatus and in or on the plasma applicator. A plasma applicator configured thus and an energy dispensing apparatus can be cleaned, disinfected and sterilized or autoclaved comparatively easily.

In contrast to the above-described variants of a plasma applicator with a plug-in apparatus, which can be brought together with an insertion apparatus, an energy transfer in the variant of a plasma applicator described here is implemented not by way of galvanic coupling but by way of electromagnetic induction. Preferably, an electrical circuit embodied to generate a voltage signal sufficient to ignite a plasma is provided either in the plasma applicator or in a mobile power supply unit, or in both. By way of example, an electrical circuit which transforms a DC voltage of a few volt, as is typically provided by accumulators and/or batteries, into an AC voltage signal suitable for inductive transfer can be provided in a mobile power supply unit. Then, an electrical circuit which transforms the voltage signal induced in the receiver coil arrangements contained in the plasma applicator into a voltage signal sufficient to ignite a plasma can be integrated in the plasma applicator.

In a further embodiment, a plasma applicator does not comprise a plug-in apparatus but instead comprises an integrated energy store, e.g., an accumulator or a capacitor, and an integrated coil arrangement for charging the accumulator or the capacitor. In this embodiment, an electrical circuit which transforms the current induced in the coil arrangement in the plasma applicator into a current-voltage signal sufficient to charge an accumulator or capacitor can additionally be integrated in the plasma applicator. A corresponding plasma applicator requires no plug-in apparatus and can be embodied without freely accessible electrical contacts. A plasma applicator embodied in this manner can be cleaned, disinfected and sterilized or autoclaved comparatively easily. Furthermore, such a plasma applicator can be implanted, for example, into the human or animal body.

In one embodiment, a plasma applicator is coated or equipped with one or more active ingredients, effective in pharmacological and/or non-pharmacological fashion, in the form of individual molecules, agglomerates or tablets (e.g., morphines, coagulants, cytokines, hydrocolloids).

In embodiments of a plasma applicator without a plug-in apparatus, an electrotechnical core can be embodied with the aforementioned features, in particular with the features specified in relation to the electrode structure and the insulation layer. Even in these embodiments without a plug-in apparatus, it is possible to ensure single use of the plasma applicator by changing electrical or mechanical components. By way of example, an electrical component intended to transmit a voltage signal sufficient to ignite a plasma to at least one electrode structure can be altered in such a way as a consequence of a first time use that, following the first time use, no voltage signal sufficient to ignite a plasma can be transmitted to an electrode structure any more.

Enclosure

Preferably, a plasma applicator for the treatment of human or animal surfaces comprises an enclosure, in particular made of a biocompatible material, such as medical silicone, a lacquer, an adhesive, a film, a textile, a compression textile or organic material such as gauze, cellulose or cotton. An enclosure comprising a combination of the aforementioned materials can also be advantageous for some applications. In particular, an electrotechnical core of a plasma applicator can be enclosed entirely or at least in part by an enclosure.

Usually, an enclosure comprises a plurality of over-molded silicone encapsulations. On the side facing the side to be treated, provision is made of a first over-molded silicone encapsulation, which fulfills the function of electrical insulation. On the side facing away from the side to be treated, the first over-molded silicone encapsulation is followed by a second over-molded silicone encapsulation, which comprises an electrically conductive silicone. This second over-molded silicone encapsulation is at ground potential and fulfills the function of contact protection such that a plasma applicator can be touched without an electrical breakdown arising between electrotechnical core and the reference potential directly applied to the outer side or a virtual reference potential in the form of the surface to be treated.

A third over-molded silicone encapsulation made of an electrically insulating silicone is applied to the second over-molded silicone encapsulation. The production of such enclosures requires a comparatively high vertical integration.

An enclosure can be formed, for example, using an injection molding method, a dipping method or a painting method. The use of other coating methods, such as plasma coating or parylene coating, is also conceivable. An enclosure can be embodied in complete or only partial fashion. By way of example, it can be advantageous if the side facing the wound is not enclosed or only partly enclosed and the side facing away from the wound is completely enclosed.

In a preferred embodiment, an electrotechnical core comprises a first insulation layer, a first electrode structure, which is grounded during operation, a second insulation layer, which is embodied to galvanically isolate the first electrode structure from a second electrode structure, a second electrode structure, which is driven during operation by a voltage signal that is provided by a power supply unit and sufficient to ignite a plasma, a third insulation layer, which is embodied to galvanically isolate the second electrode structure from a third electrode structure, and a third electrode structure, which is grounded during operation. Such an electrotechnical core already provides contact protection per se. Thus, contact protection need not be ensured subsequently by way of an applied enclosure. An electrotechnical core according to this preferred embodiment can preferably be realized by an enclosure in the form of merely a single silicone layer, which can advantageously be embodied to be comparatively thin and hence flexible. In particular, the enclosure no longer needs to ensure contact protection since this function is fulfilled by the first and third electrode structure. Thus, such an enclosure is comparatively simple and can be applied in just one production step. This significantly reduces the vertical integration during the production of a plasma applicator in comparison with a plasma applicator with a conventional enclosure as described above since an enclosure must typically be applied separately to each electrotechnical core. An electrotechnical core embodied as described herein, by contrast, can be produced comparatively easily in large numbers by way of the use of laminating machines and subsequent punching.

An electrotechnical core as per this preferred embodiment can be integrated in various enclosures in module-like fashion, without particular requirements having to be placed on an enclosure used. By way of example, a possible enclosure can be realized by a conventional plaster without overmolding, in which the electrotechnical core is integrated. A possible enclosure can also be realized by an absorbent pad, in which the electrotechnical core is integrated. A possible enclosure can also be realized by compression stockings. The electrotechnical core can also be sewn into a pocket or adhesively bonded with its back side to a blanket, a cloth, a thermal film, etc., or it can be integrated in a vacuum-assisted wound closure therapy system (VAC).

An enclosure can have a structured embodiment, e.g., in the form of a mesh or in diamond shape or with cutouts. Such a structured enclosure is particularly advantageous if it is embodied on a body-facing side of an electrotechnical core with, for example, an adhesive silicone (not completely vulcanized silicone) or any other adhesive, e.g., on acrylate basis or polyurethane basis. Furthermore, an enclosure can be embodied in such a way that an enclosure is present in certain regions around an electrotechnical core (the form can be, e.g., round, polygonal, L-shaped, M-shaped, E-shaped, X-shaped or else O-shaped) and no enclosure is present in other regions.

An enclosure can also be embodied in such a way that, outside of a region in which a plasma is generated, at least a breakdown strength and hence touch safety is ensured between the at least one electrode structure driven during use by a voltage signal and a reference potential potentially directly on the outer side or a virtual reference potential in the form of the surface to be treated. To ensure this, it is necessary to match the electrical properties of an enclosure material and its thickness to the electric potential present in an electrotechnical core. Advantageously, an additional safety factor is taken into account. By way of example, medical-grade silicone typically has a breakdown strength of approximately 20 kV per mm. If a corresponding enclosure made of medical-grade silicone has a thickness of 1 mm, it is possible, for example, to apply a voltage of 20 kV without material damage or breakdowns occurring. However, a breakdown strength differs from material to material. There are special lacquers that have a significantly higher breakdown strength than medical-grade silicone. Suppose a voltage signal used to drive at least one electrode structure has an amplitude of 5 kV, i.e., 10 kV peak-to-peak. Then, the breakdown strength of a silicone layer with a thickness of 250 μm would be sufficient to prevent breakdown in the material. The safety factor is typically given by a factor of 2. In the case where an enclosure consists of medical-grade silicone and the amplitude of the voltage signal used to drive the electrode structure is 5 kV, an enclosure must accordingly have a thickness of at least 500 μm. In the case of enclosures made of different materials, such as, e.g., lacquers and/or polyurethane, it is advantageous to match the thickness to the material properties of the material used for the enclosure.

An enclosure can also be formed by a textile, for example in the form of a pocket. An electrotechnical core can be pushed or else sewn/embossed into said pocket. Such a pocket with an inserted or sewn/embossed electrotechnical core can be fastened directly to a surface to be treated.

A pocket with an inserted or sewn/embossed electrotechnical core can also be part of another textile. The pocket can be securely sewn or riveted or fastened, e.g., by means of an adhesive, a hook-and-loop fastener or an adhesive tape, to the other textile.

An enclosure of an electrotechnical core can also be embodied in such a way that it has absorbing properties. An enclosure with absorbing properties preferably consists of at least one layer of liquid-absorbing and/or liquid-removing and/or liquid-distributing materials, such as, e.g., textile, gauze, PU foam, distributor layer, wound contact layer, spacer structure. Preferably, such an enclosure with absorbing properties is situated on the body-facing side of a plasma applicator.

An enclosure can also be formed by a combination of the aforementioned materials (e.g., textiles, silicone, lacquers, adhesives, parylene coating, plasma coating, gauze, pad). This combination can be both a mixture of the materials (e.g., textile and silicone as composite matrix) and in stacked form (e.g., different textiles layered on silicone, gauze, PU foam, distributor layer, wound contact layer) or else next to one another or on different sides. By way of example, an enclosure can be formed by a thin film on the side facing away from the patient, while an enclosure on the patient-facing side consists of one or more layers of textile and/or one or more absorbers. Depending on use, an electrotechnical core can also be fastened to a surface to be treated by way of an enclosure in the form of a bandage. In this case, an electrotechnical core is placed on the surface to be treated and affixed there by means of a fixing bandage wrapped a plurality of times around the electrotechnical core situated on the surface to be treated and said surface to be treated.

Aforementioned textiles for an enclosure can consist both of organic and inorganic materials, and of a mix of both materials.

If a plasma applicator comprises a plug-in apparatus, an enclosure of the plug-in apparatus and of an electrotechnical core is preferably interlocking and without air inclusions. If an enclosure is formed by a textile or a material with absorbing properties, an interlocking enclosure without air inclusions is not necessary. An enclosure of a plug-in apparatus is advantageously designed taking account of a corresponding insertion apparatus and the type of coupling therebetween. By way of example, if galvanic coupling is provided between a plug-in apparatus and an insertion apparatus, at least the electrical contact faces of the plug-in apparatus should be freely accessible to the electrical contact faces of the insertion apparatus. However, if inductive coupling by way of electromagnetic induction is provided, a plasma applicator can also be completely enclosed by an enclosure.

Should a plasma applicator have no plug-in apparatus and an energy store be directly integrated in the plasma applicator, the plasma applicator can likewise be completely enclosed by an enclosure.

An enclosure of a plasma applicator can be enriched and/or coated with one or more active ingredients, effective in pharmacological and/or non-pharmacological fashion, in the form of individual molecules, agglomerates or tablets (e.g., morphines, coagulants, cytokines, hydrocolloids). Enrichment with a pharmacologically effective active ingredient can be advantageous, in particular, if a plasma applicator should be integrated in a human or animal body.

A plasma applicator can be enclosed by pure gauze or cellulose or comparable materials.

In a corresponding embodiment, a plasma applicator is not enclosed by a biocompatible material such as silicone; instead, an electrotechnical core of a plasma applicator is woven or sewn/embossed in a gauze bandage or medical pillow or in cellulose. Here, it is particularly advantageous if the electrotechnical core itself has contact protection, for example by way of comprising two grounded electrode structures (a first and a third electrode structure), between which an electrode structure driven during operation (second electrode structure) is arranged.

In one embodiment variant in which a plasma applicator comprises an electrotechnical core with holes or passages which are arranged over a portion of the electrotechnical core or in a manner distributed over the entire area of the electrotechnical core, an enclosure can be designed in such a way that the enclosure allows or itself facilitates media transport through the electrotechnical core from the one side of the plasma applicator facing a surface to be treated to the side of the plasma applicator facing away from a surface to be treated. By way of example, a suitable enclosure can be formed by a media-transporting material or can likewise have holes and passages.

In one embodiment variant, in which a plug-in apparatus can be separated from the electrotechnical core at a perforation, the perforation can be embodied as part of an enclosure. The function of the perforation lies in the reduction of the strength of the enclosure at this point; it should represent a predetermined breaking point. Following the treatment, the plug-in apparatus can be torn off or removed at this perforation. As a result, a plasma applicator can continue to remain on a surface to be treated, for example over a relatively long period of time which may include a few days to weeks, and the no longer required plug-in apparatus can be removed.

In terms of its lateral extent, an enclosure can be significantly greater than an electrode structure of an electrotechnical core. By way of example, an enclosure can have an area of 20 cm×20 cm or else 30 cm×30 cm or even larger, whereas the area of an electrode structure is 10 cm×10 cm.

In one embodiment variant, in which an enclosure of a plasma applicator has a greater area than that of an electrode structure of an electrotechnical core, a user can cut the plasma applicator to size as desired prior to the plasma treatment, said size for example being able to correspond to the area of a wound, with the minimum size being specified by the size of the electrode structure.

Adhesion Layer

It may be advantageous if a plasma applicator has an adhesion layer as the last layer on the side facing the surface to be treated, in order to affix a plasma applicator on or over an area to be treated and in order to create a sealed gas space between plasma applicator and the surface to be treated. An adhesion layer preferably consists of a biocompatible material such as silicone or an acrylate-based adhesive and preferably has a thickness of between a few $\mu m$ and several hundred $\mu m$. The adhesion force of an adhesion layer can be set directly by way of the thickness of the latter. Preferably, the thickness of an adhesion layer is less than 150 $\mu m$, in particular less than 60 $\mu m$, in particular less than 20 $\mu m$.

Preferably, an adhesion layer has an adhesion force that is sufficient to make a plasma applicator adhere to a surface to be treated without additional auxiliary means or fastening material. In particular, it can be advantageous if an adhesion layer establishes an adhesive contact which lasts for a few days or even a number of weeks between a surface to be treated and a plasma applicator.

An adhesion layer can also be formed by a material or comprise a material that is photoactive. In this context, photoactive means that the adhesion force of the material can be influenced by photons. Prior to irradiation, the adhesion material is suitable for establishing an adhesive contact with another surface. Following irradiation with photons of a specific wavelength, the adhesion material loses its adhesion force and is no longer suitable for establishing an adhesive contact. A plasma applicator with a photoactive adhesion layer is suitable, in particular, for use over a relatively long period of time from a few days to weeks.

By way of example, an adhesion layer can be applied using a screen printing method or an injection molding method. It is also conceivable for an adhesion layer to be realized as rolled ware, for example by a transfer adhesive tape or by a double-sided adhesive tape.

A transfer or double-sided adhesive tape can have an elastic and hence flexible design, and so a corresponding plasma applicator can be flexibly adapted and attached to various surfaces.

By way of example, an adhesion layer can cover the edge of an enclosure of a plasma applicator such that adhesive contact between a surface to be treated and a plasma applicator is only established at said edge. An adhesion layer can also cover the entire side of a plasma applicator facing the surface to be treated such that a planar adhesive contact is established over the entire contact face between the plasma applicator and the surface to be treated.

An adhesion layer can also contain holes or else larger cutouts, e.g., in the form of circles or other geometric shapes. Advantageously, a plasma can ignite in the holes or cutouts of an adhesion layer, embodied over the entire surface, with holes or relatively large cutouts. At the same time, holes and cutouts represent possibilities for the diffusion of the active components of a plasma. Moreover, the adhesion force can additionally be set by way of the number and size of the holes or cutouts.

In the case where a plurality of electrode structures are arranged within a layer, an adhesion layer can be formed as a negative image of the distribution of the electrode structures in this layer. Consequently, a gas space, in which a plasma can spread, can be kept as large as possible.

It can be advantageous for an adhesion layer to have a fabric or a textile or for an adhesion layer to be applied to a fabric or textile.

In a further embodiment, an adhesion layer is applied on the side of a plasma applicator facing away from the surface to be treated. This is particularly advantageous if a plasma applicator should be affixed with the side facing away from the surface to be treated to, e.g., blankets, cloths or thermal blankets in first aid, for example to prevent slippage. In this case, a sealed gas space, in which a plasma ignites during operation, arises between the blanket, the cloth or the thermal blanket and the surface to be treated.

In a further preferred embodiment, an actively adhering part of a hook-and-loop closure with barbed hooks is fastened (e.g., adhesively bonded, sewn) to the side of a plasma applicator facing the surface to be treated. Such an actively adhering part of a hook-and-loop closure can particularly advantageously be used to apply a plasma applicator to a surface connected to, or covered with, textile (e.g., clothing, wound dressing, fixing bandage, compression clothing), since the barbed hooks of the hook-and-loop closure then adhere to the textile and consequently facilitate affixing a plasma applicator over a wound.

Spacer Structure

It can be advantageous if a plasma applicator as described here comprises a spacer structure on the side facing the surface to be treated. A spacer structure has the function of creating a defined distance between a plasma applicator and a surface to be treated and of consequently creating a defined gas volume in which a plasma can ignite.

A spacer structure can be connected both permanently and non-permanently to a plasma applicator. By way of example, a permanent connection can be realized by adhesive bonding and/or molding-on. In the case of the non-permanent connection, there is no mechanically and/or chemically permanent connection between a plasma applicator and a spacer structure.

Since the spacer structure is in direct contact with a wound during a plasma treatment, a spacer structure preferably consists of a biocompatible material (e.g., silicone, textile/silicone composite matrix, gauze, absorber, cellulose, wound gauze, PU foam) and/or of a combination of the aforementioned materials.

Preferably, a spacer structure is not embodied over the whole area. Preferably, a lateral extent of a spacer structure is comparable with a lateral extent of an electrode structure of an electrotechnical core.

In an embodiment of a plasma applicator with a spacer structure, the spacer structure can have cutouts in which a plasma can ignite. By way of example, such cutouts can have a honeycomb shape or be formed by holes with different sizes or formed by a mesh structure. In a further preferred embodiment, a spacer structure is formed by an X-shaped, O-shaped, Z-shaped, M-shaped, E-shaped or W-shaped structure.

In one embodiment of a plasma applicator with a spacer structure, the spacer structure can also be formed by thin webs or beads with a width of a few 100 µm up to a few mm and with a height of a few 100 µm up to a few mm.

A spacer structure is preferably embodied in such a way that it only covers a comparatively small part of a side of a plasma applicator facing the surface to be treated such that a plasma ignites in a manner spread out over a comparatively large area.

A spacer structure that can be detachably arranged on a plasma applicator can be embodied as a separate component, independently of a plasma applicator.

A spacer structure which can be detachably arranged on a plasma applicator can be realized by one or more adhesive pads. These adhesive pads typically have a flat or plane side, which is provided with an adhesion material. This adhesive side can be applied to the side of the plasma applicator facing a surface to be treated, as a result of which an adhesive pad adheres to the plasma applicator.

An adhesive pad can have different shapes and sizes. Thus, the shape can represent a hemisphere, a cuboid, a pyramid, an L shape, O shape, M shape, E shape, X shape or a combination of typical 3-dimensional geometric shapes. The diameter of an adhesive pad is preferably between 1 mm and 6 cm. The height of an adhesive pad is preferably between 100 µm and 8 mm.

An adhesive pad can be formed by silicone, felt, gauze, a cured polymer foam, textiles, PE, PP, PET or comparable materials and material combinations.

An adhesive pad is preferably formed by a biocompatible material.

An adhesive pad can also have a frame-shaped embodiment. Here, the inner diameter of the frame can be of the order of the lateral extent of an electrode structure of an electrotechnical core. By way of example, if an electrode structure spans an area of 10 cm×10 cm, the inner diameter of the frame can likewise lie in the cm range. Preferably, however, the inner diameter is greater than a longitudinal side of an electrode structure; i.e., greater than 10 cm in this case. The web width of the frame is preferably between 3 mm and 6 cm. The height of the frame is preferably between 100 µm and 8 mm.

A spacer structure embodied as an adhesive pad in a frame form is preferably embodied in such a way that the electrode structure is not covered by the spacer structure and the plasma formation at the plasma applicator is not impeded by the applied spacer structure.

A spacer structure embodied as an adhesive pad in a frame form is preferably wetted with an adhesion material both on a side of the spacer structure facing the side to be treated and on the side of the spacer structure facing away from the side to be treated. For a plasma treatment, the spacer structure can be applied to a surface to be treated with the side of the spacer structure facing a side to be treated and a plasma applicator can be arranged on the spacer structure on the side of the spacer structure facing away from the side to be treated. The spacer structure can also comprise the adhesion material itself or be formed by the latter. The spacer structure with the adhesion layer or adhesive properties can form a product that is independent of a plasma applicator and can be arranged on various plasma applicators and be used with the latter for a plasma treatment.

In an embodiment of a plasma applicator with a spacer structure, the spacer structure can be equipped and/or enriched with one or more active ingredients, effective in pharmacological and/or non-pharmacological fashion (e.g., morphines, coagulants, cytokines, hydrocolloids). Equipping within this meaning can be implemented, for example, by coating the surface of a spacer structure with the active ingredients and/or by accumulating the active ingredients in the material of a spacer structure. For equipping and/or enriching the material of a spacer structure with one or more pharmacological or non-pharmacological active ingredients, it can be advantageous if additional materials and/or means are admixed in the coating and/or the accumulation. As a result, the longevity and/or the release kinetics of the pharmacological or non-pharmacological active ingredients can be delayed (e.g., retardation) or accelerated.

In one embodiment of a plasma applicator with a spacer structure, a spacer structure can be embodied as a plasma source. Advantageously, at least one electrode structure which is applied with a voltage signal sufficient to ignite a plasma during use is then situated within a spacer structure. In this configuration with an electrode structure as a constituent part of a spacer structure, a surface to be treated represents a counter electrode during operation.

In one embodiment of a plasma applicator with a spacer structure, the spacer structure can be embodied as an electrode structure at the same time. Thus, such an electrode structure additionally fulfills the function of a spacer structure. A suitable electrode structure can be a simple electrical conductor formed by a wire with a round or oval cross section. A simple electrical conductor can also be formed by a ribbon cable. A ribbon cable within this meaning can have a square or rectangular cross section. In this case, the spacer structure is a plasma source at the same time. In the case of this embodiment, too, a counter electrode during operation is preferably realized by the surface to be treated itself.

In one embodiment, a plasma applicator with a spacer structure embodied as a plasma source, which either comprises an electrode structure or itself is an electrode structure and which is impinged by a voltage signal for the purposes of igniting a structure, comprises a further electrode structure. By way of example, the further electrode structure can be arranged as a whole-area electrode between the spacer structure and the remaining plasma applicator. A further electrode structure formed in that way is preferably grounded such that a plasma can ignite between a spacer structure embodied as a plasma source and the further electrode. In one variant of this embodiment, a further electrode structure is not embodied over the whole area but instead has cutouts, e.g., in the form of honeycombs, differently sized holes or polygonal forms.

In one embodiment of a plasma applicator with a spacer structure, the spacer structure can comprise at least two electrode structures. A preferred arrangement of the electrode structures is in the form of layers above one another in relation to the surface to be treated. Preferably, one of the electrode structures is at reference potential and at least a further one of the electrode structures is applied during operation with a voltage signal sufficient to ignite a plasma. Preferably, a grounded electrode structure is arranged closer to a surface to be treated than an electrode structure which is driven during operation. The distance between an electrode structure to be impinged during operation with a voltage signal sufficient to ignite a plasma and a surface to be treated is preferably greater than the distance between a grounded electrode structure and a surface to be treated. Preferably, a plasma ignites during operation substantially at two opposite longitudinal sides of a spacer structure.

In a preferred embodiment of a plasma applicator with a spacer structure embodied as a plasma source and a further electrode structure within and/or between the spacer structure and the remaining plasma applicator, the plasma applicator comprises no electrotechnical core embodied as a multi-layer system since a plasma source is already realized by the spacer structure embodied as a plasma source. In this case, a plasma applicator comprises, e.g., an enclosure and a spacer structure embodied as a plasma source.

In a preferred embodiment, a spacer structure embodied as a plasma source has a plug-in apparatus. The plug-in apparatus can be galvanically connected to an insertion apparatus in order to transmit to an electrode structure of the spacer structure a voltage signal sufficient to ignite a plasma. A spacer structure embodied as a plasma source can comprise a first electrode structure within the spacer structure and a second electrode structure within or outside of the spacer structure or only a single electrode structure within the spacer structure.

In a preferred embodiment, a spacer structure embodied as a plasma source is embodied independently without further constituent parts of a plasma applicator. Then, for a plasma treatment, a sealed gas space, in which a plasma should be ignited, can be realized, e.g., by placing or adhesively bonding a film above the spacer structure. As a result, the spacer structure can be fastened above the surface to be treated. A spacer structure embodied as a plasma source can comprise a first electrode structure within the spacer structure and a second electrode structure within or outside of the spacer structure or only a single electrode structure within the spacer structure. At least one of the electrode structures can be galvanically connected to a plug-in apparatus.

Access Port

A plasma applicator described here can additionally have an access port, for example for a suctioning apparatus. The access port then is preferably integrated in this plasma applicator. An access port can be used for a plurality of functions:

rinsing a wound while a plasma applicator is applied to a surface to be treated, sucking away exudate possibly excreted by a wound while a plasma applicator is applied to a surface to be treated, performing a VAC therapy while a plasma applicator is applied to a surface to be treated, and a combination of the aforementioned functions before, after and/or during a plasma treatment.

The access port is preferably embodied as a spout or nipple such that a tube can be connected to such a spout or such a nipple, which tube is connected to, e.g., a vacuum pump, to be precise in such a way that negative pressure generated by the vacuum pump can be guided via the tube to a nipple or a spout at a plasma applicator, as a result of which the aforementioned functions (rinsing, sucking, VAC therapy and the combination of individual functions among themselves, before, after and/or during a plasma treatment) can be satisfied in the sealed gas space between a plasma applicator and a surface to be treated.

A spout or a nipple preferably is tube-shaped and has a hollow interior. Preferably, the one end of this tube-shaped apparatus is in the sealed gas space between a plasma applicator and a surface to be treated and the other end is outside of the plasma applicator such that, when a plasma applicator is arranged on a surface to be treated, one or more media can be added to the sealed gas space or transported out of the sealed gas space through the tube-shaped spout.

A spout or nipple can have a round, oval, rectangular or else polygonal cross section.

In a preferred embodiment, an inner and an outer diameter of a spout or a nipple is chosen in such a way that a tube can be pushed thereon and can be fastened to the spout.

In one embodiment, a tube-shaped spout comprises a male thread or a female socket in order to fasten a tube with a complementary thread for the purposes of adding and/or removing media to or from a sealed gas space by way of a screw connection at the tube-shaped spout. In a variant of this embodiment, this tube-shaped spout is guided through an electrotechnical core. A hole or cutout can be especially provided to this end in an electrotechnical core, which hole or cutout corresponds in terms of diameter to the external diameter of the tube-shaped spout. In one variant, this tube-shaped spout is guided through an enclosure. A hole or cutout can be especially provided to this end in an enclosure, which hole or cutout corresponds in terms of diameter to the external diameter of the tube-shaped spout.

In a preferred embodiment, a spout or a nipple is integrated in a plug-in apparatus. Then, a counterpart to the spout is preferably situated in a complementary insertion apparatus such that, in the plugged together state of plug-in apparatus and insertion apparatus, the counterpart in the insertion apparatus establishes a watertight and airtight connection with the spout in the plug-in apparatus.

In a preferred embodiment, a tube-shaped spout or a tube-shaped nipple comprises an integrated valve such that a flow of the medium or media through the tube-shaped spout can be regulated and stopped by means of said valve. Such a valve can be manually controllable, machine-controllable or electronically controllable.

Plasma Applicator with a Sensor System

A sensor as described below and, optionally, a corresponding sensor system can be provided in all plasma applicators, whether they are as described here or conventional. Purely in exemplary fashion, a few preferred embodiments of a plasma applicator are described below with one sensor or else a plurality of in particular different sensors.

In one embodiment, a plasma applicator comprises an electrotechnical core, which is embodied as a plasma source, an enclosure, by means of which it is possible to establish a sealed gas space between a body segment to be treated and the plasma applicator, and at least one sensor which is embodied to capture and output measurement variables relevant to a plasma treatment and/or wound healing, in particular physiological measurement variables of a body segment covered during use by the plasma applicator.

A plasma applicator with a sensor can be used particularly advantageously, especially if a plasma applicator is intended to remain on a body segment to be treated for a relatively long period of time, for example a few days up to several weeks, in order to seal the latter against external influences. By way of example, if a plasma treatment is performed at the start of a treatment of a wound, it may be advantageous for wound healing if a plasma applicator is permanently attached to a corresponding body segment and seals the wound over a relatively long period of time of typically a plurality of days up to a plurality of weeks, for example until a corresponding wound is healed, as a result of which, advantageously, recontamination of the wound can be prevented. Following a plasma treatment, in particular, characteristic measurement variables can be captured and read, by means of at least one sensor, for a sealed gas space and/or for a wound to be treated. Capturing contains measuring a measurement variable and converting the latter into a data signal representing the measurement variable. As a result, a treatment profile of a wound can be tracked on the basis of read measurement variables, without a plasma applicator having to be removed to this end from a body segment to be treated during a healing process. Thus, a wound can remain permanently sealed during a healing process.

The at least one sensor is preferably embodied to capture a measurement variable, for example a gas pressure, a temperature, a blood oxygen saturation (SpO2 value), conductances of a wound secretion, a bacteria colonization, a pH value, a wound size, etc. Captured measurement variables can then be stored, for example as data representing the measurement variables, in a memory chip of a sensor system with at least one sensor. The data can then be read at a subsequent time by an external reader. By way of example, a sensor system comprising the at least one sensor can comprise an RFID (radio-frequency identification) transponder, which is able to access data stored in a memory chip and transmit the data to a reader when a corresponding request is put from a reader to the transponder.

A data signal representing the measurement variables can also be transmitted, preferably wirelessly, from a transmitter unit of the sensor system directly to a complementary receiver unit of a portable or stationary data processing device.

By reading measurement variables captured by a sensor, it is particularly advantageously possible to assess a treatment success of a plasma treatment and/or a progress of wound healing, without, to this end, a plasma applicator arranged on a body segment to be treated having to be removed from said body segment to be treated. This is particularly advantageous if a plasma applicator should remain applied to a body segment to be treated for a relatively long period of time. A relatively long period of time is preferably a period of time of a plurality of days or a plurality of weeks. Summed up, a period of a plurality of days can also correspond to a period of a plurality of weeks. Preferably, a relatively long period of time comprises a period of time during which a wound has at least largely healed. During this period of time, a wound to be treated is largely insulated from the surrounding atmosphere. Thus, the wound is permanently sealed during this period of time.

Advantageously, captured measurement variables can be read and interpreted directly by a physician or hospital staff, for example. Proceeding from the read measurement variables, it is possible, for example, to assess the need for a renewed plasma treatment or determine a suitable time for removing a plasma applicator.

It can also be advantageous if captured measurement variables are read by a patient themselves. By way of example, a patient can read the data representing the measurement variables at home and make these available to a physician via a network such that the latter can assess the success of the treatment without consulting a patient in person. Thus, a plasma applicator with at least one sensor particularly advantageously facilitates telemonitoring, sometimes also referred to as home-monitoring, of a patient by a physician.

It is also conceivable for an amplitude of a voltage signal sufficient to ignite a plasma to be regulated on the basis of measurement variables captured by one sensor or a plurality of sensors, in particular different sensors. To this end, for example, data representing the measurement variables or a data signal representing the measurement variables can be transmitted, preferably in wireless fashion or else by a cable, to a corresponding interface of a power supply unit such that an amplitude of a voltage signal to be provided can be modulated accordingly. In one embodiment, a plasma applicator comprises an electrical circuit which modulates a voltage signal provided to ignite a plasma, in particular an amplitude of the voltage signal, on the basis of at least one captured measurement variable.

An electrical circuit embodied to modulate a voltage signal provided to ignite a plasma, in particular an amplitude of the voltage signal, on the basis of at least one captured measurement variable can also be integrated in a power supply unit. Then, a power supply unit can be embodied, for example, to receive and process a data signal representing the captured measurement variables via a cable or in wireless fashion, either directly from one or more sensors of a plasma applicator or from a data processing device, on which data representing the captured measurement variables are stored, and to transmit a corresponding output signal to the electrical circuit.

Accordingly, a power supply unit is provided, which is embodied to provide a voltage signal sufficient to ignite a plasma and which comprises an interface for receiving a data signal representing the captured measurement variables and an electrical circuit, wherein the electrical circuit is embodied to modulate a voltage signal provided to ignite a plasma, in particular an amplitude of the voltage signal, on the basis of the received data signal.

By way of example, a sensor can be a gas pressure sensor which is embodied and arranged to measure a gas pressure in a sealed gas space or a pressure sensor which is embodied and arranged to measure the pressure of a compression bandage or a temperature sensor which is embodied and arranged to measure a temperature, in particular in a sealed gas space, or a pH value sensor which is embodied and arranged to measure a pH value, in particular of a wound, a moisture sensor which is embodied and arranged to measure a moisture in a wound environment or a metabolic product sensor which is embodied and arranged to capture metabolic products, in particular, which are characteristic for wound healing. By way of example, such metabolic products could be proteins such as fibrin or lactates. Metabolic products characteristic for wound healing can also be metabolic products that are emitted by bacteria over a bacterial film of a wound.

A sensor system can also comprise a plurality of sensors, in particular different sensors, and be embodied as a microelectromechanical system (MEMS), for example. Such microelectromechanical systems represent a compact unit which can be particularly advantageously integrated in a plasma applicator.

In one embodiment, a plasma applicator comprises a sensor system which comprises a plurality of sensors, in particular different sensors. The sensors are preferably embodied to capture and output respectively different physiological measurement variables of a body segment covered by the plasma applicator during use. The plurality of sensors of a sensor system are preferably arranged at different points on a plasma applicator. Preferably, one sensor of the plurality of sensors is arranged at a point that is particularly suitable for capturing a corresponding measurement variable. A sensor provided to measure a gas pressure is preferably arranged at a distance from the wound at the plasma applicator where it is accessible to a gas space. A temperature sensor that is provided to measure conductance of a wound secretion is preferably arranged in such a way that it is in contact with a wound to be treated during use.

A sensor system comprising a plurality of sensors, in particular different sensors, can also be embodied as a microfluidic system, which is also referred to as a lab on a chip system, which may be embodied, for example, to capture a bacterial film of the wound or a type and concentration of pathogens in the blood or in a wound secretion. In one embodiment, a plasma applicator comprises a sensor system embodied as a microfluidic system, wherein the sensor system is arranged at the plasma applicator in such a way that it is in contact with a wound to be treated during use, for example in order to be able to take up and analyze wound secretion or blood.

A sensor is preferably arranged at the plasma implicated in such a way that measurement variables, in particular physiological measurement variables, relevant to a plasma treatment and/or wound healing can be captured by the sensor. In one embodiment, a sensor is arranged in such a way that the latter is situated in a sealed gas space at a distance from a body segment to be treated during a plasma treatment. A sensor arranged in this way can particularly advantageously measure measurement variables specific to the sealed gas space, such as temperature or gas pressure. In one embodiment, a sensor is arranged in such a way that the latter is in direct contact with a body segment to be treated during a plasma treatment. A sensor arranged in this way can particularly advantageously measure measurement variables specific to the body segment to be treated, such as a bacterial film or an oxygen saturation of the wound. It can also be advantageous to arrange a sensor in such a way that it is possible to capture measurement variables characteristic for an electrotechnical core.

In one embodiment, a plasma applicator comprises an electrotechnical core, an enclosure with a pocket, wherein the electrotechnical core can be inserted into the pocket and removed from the latter, and at least one sensor which is embodied to capture and output measurement variables, in particular physiological measurement variables, relevant to a plasma treatment and/or wound healing. Preferably, the enclosure is at least partly see-through or optically transparent to such an extent that a person can assess a state of a wound visually when the plasma applicator is applied to a body segment to be treated, i.e., over the wound to be treated. Then, a plasma treatment can be carried out first. Following the plasma treatment, the electrotechnical core can be removed from the pocket such that a view through the enclosure to the wound is facilitated. If a plasma treatment should be carried out again, an electrotechnical core, as a module, can be inserted back into the pocket of the enclosure again. As a result, a progress of a wound healing can also be assessed visually in addition to an interpretation of measurement variables captured by a sensor system. In one embodiment, a plasma applicator comprises an enclosure with a pocket, in which the electrotechnical core is arranged in removable fashion. The enclosure is embodied in such a way that a body segment is recognizable through the enclosure when the electrotechnical core has been removed and the plasma applicator is arranged on said body segment to be treated.

A visual assessment of a wound situated under an applied plasma applicator can also be facilitated by virtue of an enclosure of a plasma applicator comprising a viewing window which is arranged in that region of the enclosure which allows a person to assess a state of a wound to be treated through the viewing window without a plasma applicator having to be removed to this end. Therefore, an enclosure has a viewing window in one embodiment of a plasma applicator, said viewing window being arranged in such a way that a body segment is recognizable through the viewing window when the plasma applicator is arranged on said body segment.

In one embodiment, a plasma applicator comprises an electrotechnical core, an enclosure with a viewing window, wherein the viewing window is arranged in such a way that a body segment, to which the plasma applicator is applied, can be visually assessed through the viewing window, and at least one sensor which is embodied to capture and output measurement variables, in particular physiological measurement variables, relevant to a plasma treatment and/or wound healing. A viewing window is preferably arranged in an enclosure in such a way that a view of a wound is not blocked by an electrotechnical core. To this end, it can be advantageous if an electrotechnical core comprises a passage centrally, above which the viewing window is arranged.

In one embodiment, a plasma applicator comprises an electrotechnical core, an enclosure, at least one sensor and a gel layer, wherein the gel layer is arranged on the side of the plasma applicator facing a body segment to be treated. When a plasma applicator is arranged on a body segment to be treated, the gel layer preferably causes the contact pressure exerted by the plasma applicator on the body segment to be treated to be distributed uniformly over an area of the body segment to be treated. This is particularly advantageous if a plasma applicator should remain on a body segment for a relatively long period of time.

In one embodiment, a plasma applicator comprises an electrotechnical core, an enclosure, at least one sensor and an air cushion, wherein the air cushion is arranged on the side of the plasma applicator facing a body segment to be treated. An air cushion preferably has a ring-shaped embodiment and is filled with air. Here, the ring-shaped air cushion has an inner diameter, which corresponds to the diameter of the opening in the ring-shaped air cushion, and an outer diameter, which corresponds to the diameter of the overall scope of the air cushion. The inner diameter preferably corresponds to at least one lateral extent of an electrode structure of the electrotechnical core. The outer diameter preferably corresponds to the outer dimensions of the plasma applicator. When a plasma applicator is arranged on a body segment to be treated, the air cushion preferably causes the contact pressure exerted by the plasma applicator on the body segment to be treated to be distributed uniformly. This is particularly advantageous if a plasma applicator should remain on a body segment for a relatively long period of time.

In one embodiment, a plasma applicator comprises an electrotechnical core, an enclosure, at least one sensor, and a layer which is enriched or coated with pharmacologically and/or non-pharmacologically effective active ingredients and which is situated directly on the body segment to be treated during a plasma treatment. Such a layer can be realized particularly advantageously by a spacer structure. Particularly if a wound is sealed for a relatively long period of time, preferably until a wound is healed, active ingredients can be released to the wound to be treated during this period of time in order to assist wound healing and in order to treat specific and/or additional indications.

In one embodiment, a plasma applicator comprises an electrotechnical core, an enclosure, at least one sensor, and an adhesion layer, wherein the adhesion layer is embodied to ensure adhesive contact between the remaining plasma applicator and a surface to be treated over a period of time of a plurality of days, in particular until the wound has successfully healed. Such a period of time may also comprise a plurality of weeks under certain circumstances. Preferably, the adhesion layer has a self-adhesive embodiment. By way of example, a self-adhesive adhesion layer can be formed by a suitable adhesive, e.g., silicone. Preferably, an adhesion layer ensures a secure adhesive contact between a plasma applicator and a body segment to be treated. Preferably, an adhesion layer is embodied in such a way that it degrades over a certain period of time, preferably of a plurality of days, or that it dissolves as a result of the addition of solvents, e.g., alcohol.

In one embodiment, a plasma applicator comprises an electrotechnical core, an enclosure, at least one sensor, and an access port, which is arranged in such a way that, when the plasma applicator is arranged on a body segment to be treated, a fluid medium can be supplied to or removed from a sealed gas space. If a plasma applicator remains over a body segment to be treated for a relatively long period of time, this allows a fluid medium to be either supplied or removed in a targeted fashion in various stages of wound healing in order thus to assist wound healing. Advantageously, an access port allows a VAC therapy to be carried out. By way of example, a VAC therapy can be controlled by liquid sensors. If a plasma applicator comprises an access port, exudate can advantageously be transported out of the gas space despite a body segment to be treated being sealed. An access port advantageously renders it possible to establish an aerobic or anaerobic atmospheric environment in the gas space.

In one embodiment, a plasma applicator comprises an electrotechnical core, an enclosure, and at least one sensor, wherein the enclosure is formed by a hydrophobic material or coated with a hydrophobic coating. This advantageously prevents an ingress of liquids into the gas space while a plasma applicator is arranged over a plurality of days on a body segment to be treated.

A method for permanent wound-sealing of a wound with a plasma applicator, wherein the plasma applicator comprises an enclosure, an electrotechnical core, and at least one sensor, includes at least the following steps:
applying a plasma applicator on a body segment to be treated such that a closed gas space is formed between the plasma applicator and the body segment to be treated,
performing a plasma treatment, wherein this includes the application of a voltage suitable for igniting a plasma to an electrode structure of the electrotechnical core,
leaving the plasma applicator on the body segment to be treated such that the sealed gas space remains beyond the plasma treatment, and
capturing and outputting a physiological measurement variable of a body segment, covered by the plasma applicator, by means of the at least one sensor while the plasma applicator is left on the body segment to be treated.

The leaving step preferably extends over a period of time that corresponds to a period of time that a wound to be treated takes to heal. Thus, the time duration of this step may extend over a plurality of weeks. Physiological measurement variables relevant to the wound healing are then captured and output by means of a sensor during this period of time. Preferably, individual steps of the method are carried out multiple times during the leaving step. Thus, it may be advantageous if, for example, a plasma treatment is performed multiple times during the leaving step.

A plasma applicator comprising neither sensor nor sensor system can also be used to seal a body segment, in particular a wound. Such a method includes the steps of:
applying a plasma applicator, which comprises an electrotechnical core and an enclosure, on a body segment to be treated such that a closed gas space is formed between the plasma applicator and the body segment to be treated,
performing a plasma treatment, wherein this includes the application of a voltage suitable for igniting a plasma to an electrode structure of the electrotechnical core,
leaving the plasma applicator on the body segment to be treated such that the sealed gas space remains beyond the plasma treatment over a plurality of days.

Such a method can be carried out using the plasma applicators described within the scope of this description and using other conventional plasma applicators. By leaving the plasma applicator on the body segment to be treated, a body segment to be treated is sealed and consequently insulated against external influences. The leaving step over a period of time of a plurality of days extends, in particular, over a period of time during which a wound has largely healed. Preferably, a plasma applicator is arranged on a body segment to be treated, a plasma treatment is carried out, and the plasma applicator is left on the body segment to be treated until a wound has healed. Such a period of time typically comprises a plurality of days which, when summed, may also yield a period of time of a plurality of weeks.

Igniting a Plasma

To ignite the plasma, a voltage signal sufficient to ignite a plasma is provided at at least one electrode structure of an electrotechnical core by means of a power supply unit.

Preferably, a power supply unit is embodied to provide a voltage signal sufficient to ignite a plasma as a rectangular voltage, a sawtooth voltage or a sinusoidal voltage. Preferably, a power supply unit is embodied to provide individual repetitive pulses; by way of example, an AC voltage can be provided in pulsed fashion.

For plasma treatment, it may be advantageous if a sinusoidal voltage with 9 kV peak-to-peak, pulsed with 20 μs on, 180 μs off, 5× per second (5 Hz) is provided. Advantageously, this allows the temperature of an ignited plasma to be kept low. Advantageously, a plasma is ignited during an overall time of approximately 10% of the treatment time.

In alternative variants, provision can be made for a voltage signal of a few 100 V to 5 kV peak-to-peak to be used. In further variants, the provision of another pulse pattern can be provided. By way of example, it may be advantageous to use a number of short pulses in order to achieve a corresponding concentration of an active species and to no longer ignite a plasma for a few seconds following the sequence of short pulses. Such a plasma treatment can lead to an improved treatment result in the case of specific clinical pictures. At the same time, the power consumption can be set in a targeted fashion by way of the duration of the pulses and by way of the pauses between the pulses. In the case of operation with a mobile power supply unit, in particular, a brief ignition of a plasma with a comparatively long pause is advantageous since the energy needs significantly reduce as a result thereof and a longer treatment duration with a comparatively small energy store is facilitated.

Should a first electrode structure be provided in an electrotechnical core, the latter is then preferably at reference or ground potential and therefore forms an electrical counter pole for the second electrode structure, which is driven by the voltage signal. Then, an electric field is applied between the two electrode structures or at least the second electrode structure and the surface to be treated, with a short circuit between the electrode structures being prevented or suppressed by the insulation layer arranged between the electrode structures. Instead, a large-area, dielectric barrier discharge plasma forms. Since the plasma properties depend strongly on the gas space thickness, in particular on the gas volume between a grounded electrode structure and a surface to be treated, in particular a human or animal surface, provision can be made of a spacer structure which allows a reliable and reproducible provision of a sufficient amount of gas in the sealed gas space between the plasma applicator and the surface to be treated for the purposes of generating a plasma with always the same effects. Here, a gas or gas mixture to be ionized is a supplied working gas and/or the ambient or external air.

BRIEF DESCRIPTION OF THE DRAWINGS

Exemplary embodiments of the invention will be described below on the basis of the figures. The intention is that these represent the exemplary embodiments not necessarily true to scale; rather, the figures are embodied in schematic and/or slightly distorted form. The features disclosed in the description, in the figures, and in the claims may be essential for the realization of the invention, both individually and in any combination. Here, identical and/or similar features with an identical or similar function have been provided with the same reference sign wherever this is expedient. Further advantages, features and details of the invention emerge from the description of the preferred exemplary embodiments below and on the basis of the figures.

FIG. 7: shows an exploded view of a known apparatus for generating a cold atmospheric pressure plasma for the treatment of surfaces, FIG. 8A shows a plasma applicator which is brought together with a mobile power supply unit with an insertion apparatus, FIG. 8B shows a plasma applicator with an integrated mobile power supply unit and a plug-in apparatus, FIG. 8D shows a plasma applicator with an insertion slot for a mobile power supply unit, FIG. 8F shows a plasma applicator with an integrated power supply unit with an accumulator, which can be inductively charged by means of a likewise integrated charging apparatus, FIG. 10A shows a spacer structure, which is simultaneously embodied as a plasma source for generating a dielectric barrier discharge (DBD), FIG. 10B shows a cross section through the spacer structure shown in FIG. 10A, FIG. 11 shows a closed electric circuit consisting of a two-core cable, FIG. 29 shows a plasma applicator with a sensor system.

DETAILED DESCRIPTION

Figure 1:
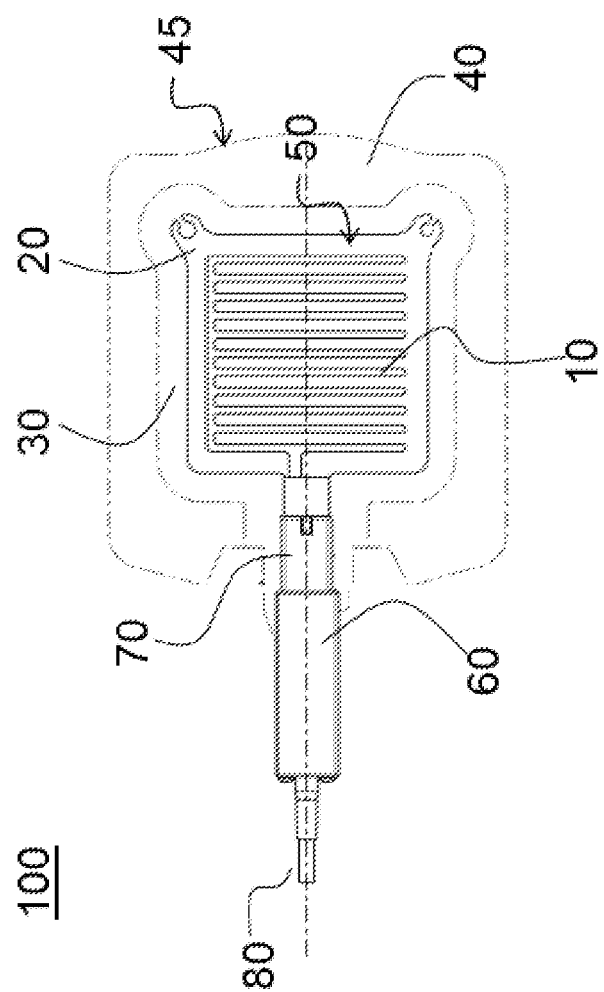
FIG. 1: shows a plasma applicator with a plug-in apparatus, which is brought together with an insertion apparatus.

FIG. 1 shows a preferred embodiment of a plasma applicator 100 with an electrotechnical core 50 and with a plug-in apparatus 70, which is embodied as a chip card-like plug. The plug-in apparatus 70 is brought together with an insertion apparatus 60 that is embodied as a complementary receiving socket. The insertion apparatus 60 and the plug-in apparatus 70 have electrically conductive conductor tracks, which are galvanically coupled at corresponding contact faces in the combined state. In particular, the conductor track of the plug-in apparatus 70 has a conductor that leads from a contact face in the plug-in apparatus to at least one electrode structure 10.

The electrode structure 10 is part of the electrotechnical core 50, which furthermore comprises an insulation layer 20 in the shown embodiment. The edge of the insulation layer 20 projects beyond the electrode structure 10 in the lateral direction by the length of the creepage distances at a voltage typical for the application.

In the shown embodiment, the electrode structure 10 consists of a silver conductive varnish, which has a comb-shaped embodiment. In different variants of the embodiment shown, an electrode structure can also be formed in the form of thin metal layers, metal films, metal meshes and/or with conductive polymer layers. A variant in which an electrode structure of a corresponding electrotechnical core is formed by electrically conductive threads which are woven into a textile is also conceivable. In a further variant, an electrode structure of a corresponding electrotechnical core is formed as an electrically conductive structure made of a conductive, flexible material, such as a conductive plastic, a material enriched with conductive particles, a metallic film or graphite.

The electrode structure 10 of the shown embodiment is electrically connected to a conductor truck of the plug-in apparatus 70. The insertion apparatus 60 is connected to a cable 80. At the other end of the cable 80, the cable 80 is typically connected to a power supply unit (not shown) predominantly used in stationary fashion, such as a high-voltage generator. The power supply unit (not shown) provides a voltage signal sufficient to ignite a plasma and can comprise a controller and a reader for digital data. For operation, the plug-in apparatus 70 of the plasma applicator 100 is brought together with the insertion apparatus 60. A voltage signal provided by the power supply unit (not shown) is transferred via the cable 80 and the plug-in apparatus 70, brought together with the insertion apparatus 60, to the electrode structure 10 for the purposes of igniting a plasma during the operation of the plasma applicator 100.

The electrode structure 10 of the electrotechnical core shown has the function of an electrode structure driven by the voltage signal and preferably has a flexible embodiment. Typically, a further electrode structure having the function of a ground electrode is required. In the embodiment shown, the electrotechnical core 50 only comprises one electrode structure 10 and, when the plasma applicator is applied at or on a human or animal or technical surface, the counter electrode is realized by the human or animal body or the technical surface itself. In one variant of the shown exemplary embodiment, the counter electrode, as a further electrode structure, is a constituent part of the flexible, planar electrotechnical core and situated on the side facing the surface to be treated. In this variant, the driven electrode structure and the grounded electrode structure consist of the same material and have the same specific geometry. However, the electrode sections of the driven electrode structure and the grounded electrode structure are arranged offset from one another with a defined overlap. An electrode section of a corresponding electrode structure preferably has a width of 5 mm and a thickness of 14 μm in the embodiment shown and the variants described.

The cross-sectional form of the electrode sections of an electrode structure was found to be the relevant variable. The conductivity in combination with a cross-sectional form of the electrode sections of an electrode structure is preferably rated in such a way that a conductor track forming a respective electrode section has a resistance in the single-digit ohm range. What emerges herefrom is that the voltage only drops by a few volts between the start of a conductor track of an electrode structure and the end, consequently allowing the provision of a homogeneous discharge over the entire area of an electrode structure. A resistance in the electrode structure, totaling 2 ohms, is currently preferred.

Higher resistance values, for example up to 50 ohms, are also conceivable. However, a greater voltage drop can be observed at higher resistances and the electrode structures heat up significantly.

However, for some applications it could also be advantageous if an electrode section of an electrode structure of an electrotechnical core has a width of 1 mm and a thickness of 70 µm. For yet further applications it could also be advantageous if an electrode section of an electrode structure of an electrotechnical core has a width of 10 mm and a thickness of 7 µm.

To generate a planar plasma, in particular a cold plasma, an isolation layer 20, which is arranged between the driven electrode structure 10 and the surface to be treated, is situated in the electrotechnical core 50.

In the embodiment shown, the insulation layer 20 consists of an electrically non-conductive plastic. However, the insulation layer 20 can also consist of a ceramic or a plastic-ceramic mixture or a natural fiber composite, or else other natural materials. The insulation layer 20 preferably has a thickness which ranges between a few µm and a few 100 µm. The insulation layer 20 is preferably pore-free; i.e., it has no or only very few holes or cavities. Furthermore, the insulation layer 20 has a dielectric strength of at least 5 kV per mm thickness. The lateral extent of the insulation layer 20 corresponds to the dimension of the electrode structure 10 in the electrotechnical core 50, plus an edge protruding therebeyond, the edge being dimensioned such that it covers at least the length of the creepage distances in the case of typical applied voltage values for igniting the plasma.

In one variant, not shown, of the embodiment shown here, the lateral extent of an insulation layer is chosen in such a way that there is no arc discharge between a electrode structure, which is driven during use, and a further electrode structure at reference potential or the surface to be treated. Typically, the creepage distances can be undercut by the use of specific insulation mechanisms (e.g., overmolding) without thus yielding a fault. Depending on an enclosure of an electrotechnical core, a lateral extent of an insulation layer can therefore also be designed to the effect of the edge of the insulation layer projecting beyond an electrode structure being smaller than what is prescribed by the amplitude of the voltage signal, as a creepage distance, required for igniting a plasma.

In a further variant, not shown, of the embodiment shown, in which the electrotechnical core comprises a first and a second electrode structure, the electrotechnical core preferably comprises a further insulation layer, which is arranged between the grounded electrode structure and the surface to be treated. The further insulation layer preferably consists of a biocompatible material such as, e.g., lacquer, silicone, polyurethane or a coating. The coating can be applied using plasma-assisted chemical vapor deposition (PACVD), chemical vapor deposition (CVD), anodizing processes or electroplating.

In the exemplary embodiment shown, the plasma applicator 100 is partly enclosed by a biocompatible material 45, such as, e.g., medical-grade silicone or a lacquer. Here, the lower side of the electrotechnical core 50, i.e., the side facing the surface to be treated, is not enclosed and the upper side of the electrotechnical core 50, i.e., the side facing away from the surface to be treated, is completely enclosed. The enclosure is embodied in such a way that at least the dielectric strength is ensured between the driven electrode structure 10 and a reference potential directly applied to the outer side.

The plug-in apparatus 70 is likewise partly enclosed. In particular, the enclosure of the plug-in apparatus 70 and of the electrotechnical core 50 is interlocking and without air inclusions. To facilitate galvanic coupling between the plug-in apparatus 70 and the insertion apparatus 60, the electrical contact faces of the plug-in apparatus 70 are freely accessible to the electrical contact faces of the insertion apparatus 60; i.e., they are not enclosed.

In the embodiment shown, an adhesion layer 40 has been applied along the edge of the enclosure 45 on the side facing the surface to be treated. The adhesion layer 40 allows the plasma applicator 100 to be affixed to a human or animal or technical surface to be treated. The adhesion layer 40 preferably consists of a biocompatible material such as, e.g., silicone or an acrylate-based adhesive and preferably has a thickness of between a few µm and several hundred µm. Once the plasma applicator has been attached by means of an adhesion layer to a surface to be treated, the adhesion layer generates an adhesion force that is sufficient to allow the plasma applicator to adhere without additional aids to the surface to be treated. By way of example, the adhesion layer can be applied using a screen printing method or an injection molding method. It is also conceivable for the adhesion layer to be realized by a transfer adhesive tape or by a double-sided adhesive tape. The transfer or double-sided adhesive tape can have an elastic and hence flexible design, and so a corresponding plasma applicator can be flexibly adapted and attached to various surfaces.

A voltage signal is applied to the driven electrode structure of the electrotechnical core for the purposes of igniting the plasma. Should a further electrode structure be provided in the electrotechnical core, the latter is at ground or ground potential and therefore forms a counter electrode for the electrode structure driven during operation by a voltage signal. Then, an electric field is applied between the two electrode structures or the electrode structure, which is driven during operation, and the surface to be treated, with a short circuit between the electrode structures being prevented or suppressed by the insulation layer between the two electrode structures. Instead, a large-area, dielectric barrier discharge plasma forms.

In an embodiment not shown here, an electrotechnical core comprises an electrode structure, which is driven during operation, and a counter electrode, wherein the counter electrode is embodied during operation to generate a voltage offset by means of a DC voltage applied to the counter electrode and to accelerate charged particles from a plasma toward a wound. In an embodiment not shown here, a counter electrode is embodied to generate a voltage offset by means of a DC voltage. In this case, the counter electrode is embodied to be connected to a corresponding voltage source.

The plasma applicator 100—when applied to a surface during use—defines a sealed space, the treatment region 30, in which a plasma is generated. The treatment region 30 is preferably sealed in air-tight fashion. Preferably, the treatment region 30 is situated at a distance of a few millimeters from the surface to be treated such that a cold plasma distributes over the area above the human or animal or technical surface to be treated. Here, a plasma treatment has a typical time duration of a few minutes.

Figure 2:
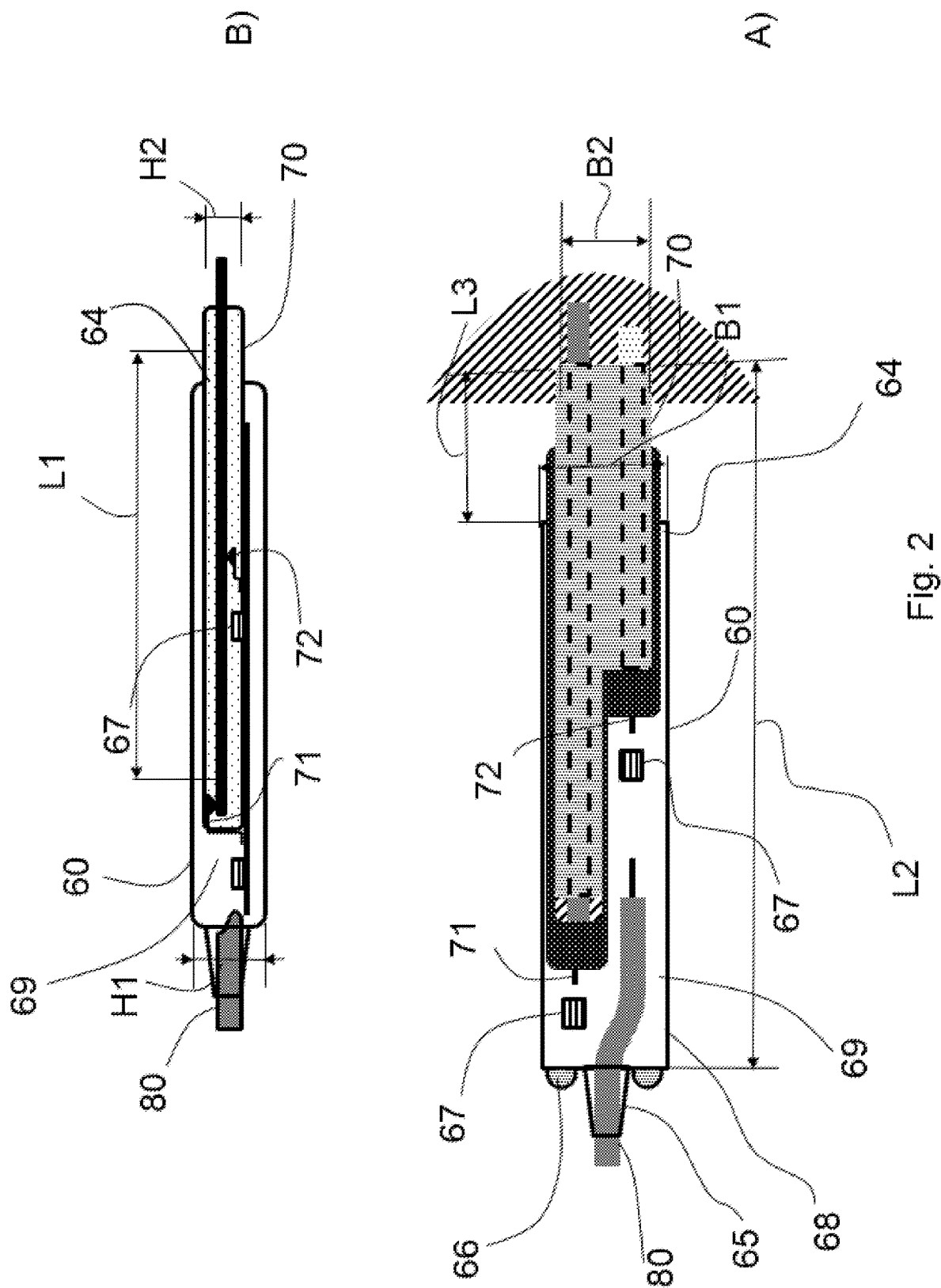
FIG. 2A: shows a side view of a section along the width through a plug-in apparatus brought together with an insertion apparatus.
FIG. 2B: shows a side view of a section along the height through a plug-in apparatus brought together with an insertion apparatus.

FIG. 2A shows a preferred embodiment of a plug-in apparatus 70, which is embodied as a plug, and which is brought together with an insertion apparatus 60, which is embodied as a receiving socket. The shown illustration illustrates a side view of a section along the width through a plug-in apparatus brought together with an insertion apparatus.

The insertion apparatus 60 has a with B1 of 30 mm. A cable 80 is connected to the insertion apparatus 60 via a connector. A power supply unit (not shown) can be connected to the other end of the cable 80, said power supply unit providing the voltage signal for igniting a plasma during operation. The connector 65 has an insulating structure made of polyethylene, which is provided with an electromagnetic shield (EMC shield) on the outside. The shield can suppress increased emission of interference waves, which could potentially interfere with other electrical devices, e.g., in a hospital. Furthermore, this shield can minimize the sensitivity to external interference from other beam sources.

However, in different variants, the insulating structure can also consist of other flexible and pore-free insulators (e.g., plastics or ceramics). The cable 80 is clad with a silicone spout. The insertion apparatus 60 furthermore comprises sealing plugs 66, which are provided to completely fill the housing with an insulator (e.g., epoxy or silicone). Here, a first sealing plug 66 is provided as an inlet for the epoxy or the silicone and a second sealing plug 66 is provided as an air outlet so that air can escape from the housing during the filling.

Furthermore, inductors 67 are provided; these serve as filters for specific interference frequencies. The housing 68 of the insertion apparatus 60 is metallized for a comparatively good EMC shield. The entire housing 68 preferably consists of an electrically conductive material. Alternatively, the housing 68 can also be, for example, metallized on the inside or shielded by a mesh. In both variants, the shield of the housing 68 is placed on PE and the housing 68 is consequently electrically shielded (Faraday cage).

The interior 69 of the insertion apparatus 60 is encapsulated with silicone or another material with a high breakdown strength (e.g., epoxy resin) in order to ensure a dielectric strength and avoid partial discharges. A further advantage is that the mechanical and electrical components in the insertion apparatus can have a small and compact structure. Moreover, an ingress of moisture, e.g., during steam sterilization, is prevented.

The insertion apparatus 60 shown comprises a high-voltage connector (HV connector) 71 and a ground connector (GND connector) 72. In the variant shown here, the width B2 of the plug-in apparatus is 24 mm. If the plug-in apparatus 70 is completely received within the insertion apparatus 60, the length L2 of the system of the two brought together apparatuses is 124 mm in the variant shown here. Here, the plug-in apparatus 70 protrudes in the variant shown here from the insertion apparatus 60 with a length L3 of 36 mm. The part of the plug-in apparatus 70 which protrudes from the insertion apparatus can preferably be enclosed by the enclosure, e.g., made of silicone, and then serves for fastening the plug-in apparatus 70 to an electrotechnical core (not shown).

In an embodiment not shown here, a plug-in apparatus has a round shape. Other plug shapes are also conceivable, wherein an avoidance of partial discharges and, as a rule, the shield should be taken into account.

It should be noted that the size and shape of a suitable system consisting of plug-in apparatus and insertion apparatus typically depend on the amplitude of the voltage signal provided for operation. In the case where a voltage signal of 1 kV is provided by a power supply unit for igniting a plasma during operation, the size specifications described in relation to FIG. 2A can be significantly smaller, and so a corresponding plug-in apparatus has a smaller and more compact design.

The plug-in apparatus has a latching apparatus 64, which, in the brought together state, is received by an insertion apparatus with a complementary embodiment. As a result, plug-in apparatus and insertion apparatus are mechanically interconnected.

FIG. 2B shows a side view of a section along the height through the plug-in apparatus, shown in FIG. 2A, brought together with the insertion apparatus. The insertion apparatus 60 is connected to the cable 80 on the one side and has a height H1 of 14 mm. On the opposite side, the insertion apparatus 60 has an opening for receiving the plug-in apparatus 70. The plug-in apparatus 70 has a maximum height H2 of 6.8 mm. When the plug-in apparatus 70 is completely received within the insertion apparatus 60, the minimum creepage distance on the patient-side has a length L1 of 85 mm. In the brought-together state, plug-in apparatus 70 and insertion apparatus 60 are mechanically connected by means of the latching apparatus 64.

Figure 3:
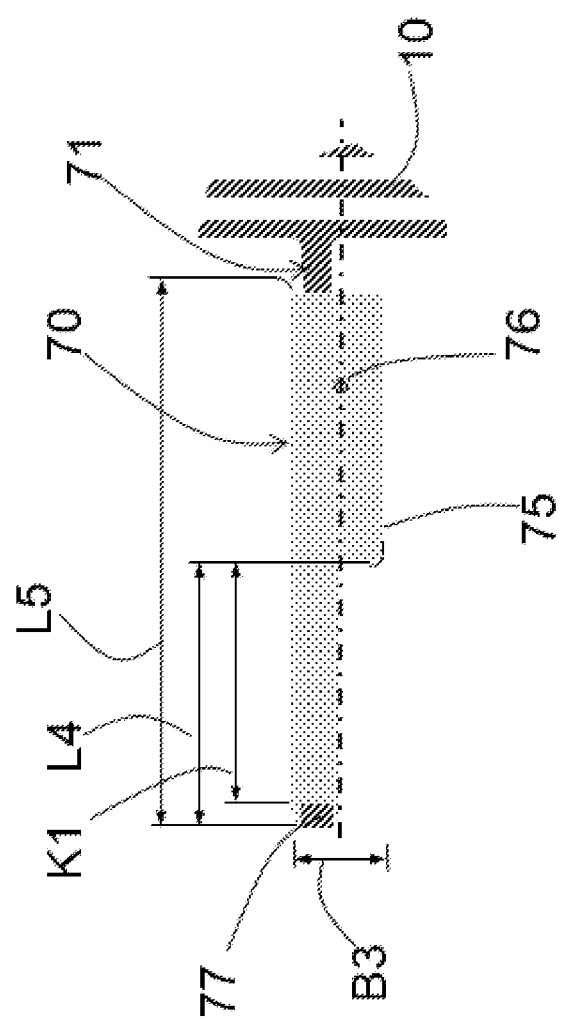
FIG. 3: shows a side view of a section along the width of a plug-in apparatus in the form of a plug, which is electrically connected to an electrode structure.

FIG. 3 shows a preferred embodiment of a plug-in apparatus 70. The illustration shown here shows a plan view of a section along the width of the plug-in apparatus 70. The plug apparatus 70 is electrically conductively connected to an electrode structure 10 by way of at least one conductor track 71, wherein the conductor track 71 leads from the contact face of the voltage connector (HV connector) 77 to the electrode structure 10. In the embodiment shown, the maximum width B3 of the plug-in apparatus 70 is 21 mm. In the embodiment shown, the plug-in apparatus 70 has an optional reinforcement 75, which may consist of, e.g., a polyethylene (PE) film and which may have a height of 0.2 mm to 1 mm, for example. In the exemplary embodiment shown, the reinforcement has the function of increasing the modulus of elasticity. This reduces bending or a change in shape as a result of an action of external mechanical forces and the plug apparatus can be easily pushed into the insertion apparatus without complications.

Furthermore, the plug-in apparatus 70 has a bore 76 with a latching function, which is embodied to mechanically lock the plug-in apparatus with an insertion apparatus which is not shown here. On the side facing away from the electrode structure 10, the plug-in apparatus 70 has a narrower width than the maximum width B3 of the plug-in apparatus 70 over a length L4 of 58 mm. The described shape is chosen, in particular on account of the creepage distances and the avoidance of partial discharges, in such a way that there is no arc discharge in the coupling that is connected via a cable to a power supply unit and to which a voltage is applied when no plug-in apparatus is inserted. On the side facing away from the electrode structure 10, the plug-in apparatus 70 has a contact face 77 in order to connect the plug-in apparatus 70 to an HV connector, not shown here. In the illustration of the plug-in apparatus 70 shown, the minimum creepage distance K1 between the HV connector (not shown) and the GND connector (not shown) is 53 mm and the overall length L5 of the plug-in apparatus 70 is 119 mm.

As a result of the chip card-like form of the plug-in apparatus, i.e., a small height and a comparatively long length, it is possible to maintain creepage distances, in particular, in such a way that no partial discharges arise within the plugged together plug-in apparatus and insertion apparatus. The specified dimensions for the length, the width and the height can also advantageously be realized independently of one another so that the creepage distances for the voltage amplitude required to generate the plasma can continue to be maintained. Accordingly, length, width, and height can deviate from the values specified in variants of the described embodiment.

Figure 4:
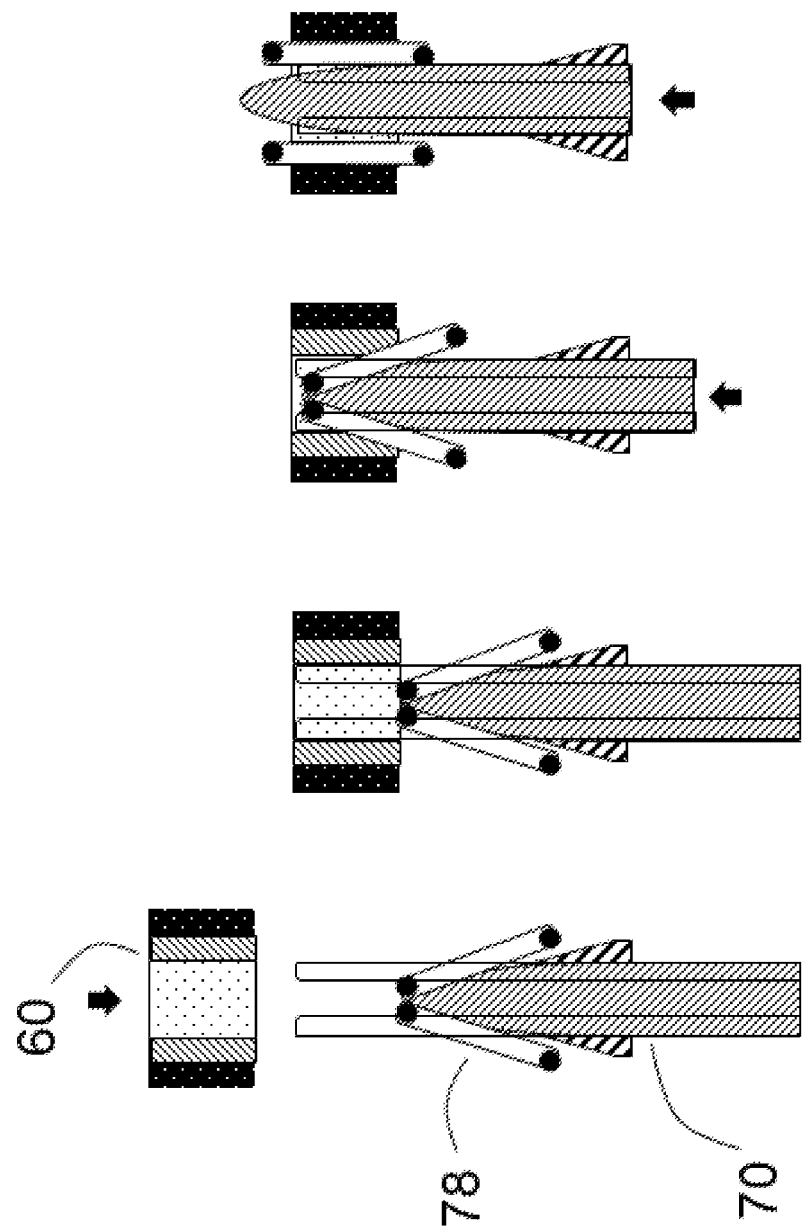
FIG. 4: shows a mechanism for a secure connection between a plug-in apparatus and an insertion apparatus.

FIG. 4 shows a mechanism for a secure connection between a plug-in apparatus 70 and an insertion apparatus 60 by means of a clamping contact 78, which is situated on the plug-in apparatus 70. By plugging together plug-in apparatus 70 and insertion apparatus 60, a secure plug-in connection is established by the latching of clamps, serving as locking elements, in the insertion apparatus 70. In an exemplary embodiment not shown here, a secure connection between a plug-in apparatus and an insertion apparatus can be ensured by expansion tongues on the plug-in apparatus that serve as locking elements.

To ensure single use, a plug-in apparatus is preferably designed in such a way that it is modified during the mechanical separation from the insertion apparatus as a result of first-time use such that a renewed electrical connection to the insertion device is no longer possible since a sufficiently secure mechanical connection is no longer possible. In different variants, single use of a plug-in apparatus can be realized by virtue of clamps breaking off, latching elements breaking off, locking elements becoming unusable or the conductor tracks of the plug-in apparatus being scratched or cut apart during the mechanical separation from the insertion apparatus.

In a further exemplary embodiment not shown here, a connection with sufficient tensile strength between a plug-in apparatus and an insertion apparatus can be ensured by magnetic contacts. In this case, there is at least 1 magnet in each of the plug-in apparatus and the insertion apparatus. Advantageously, the magnets in the plug-in apparatus have an opposite polarity to the magnets in the insertion apparatus.

Preferably, the plug-in connection between the plug-in apparatus and the insertion apparatus is embodied in such a way that the insertion apparatus connected to a cable is usable multiple times. In an embodiment not shown here, kink protection is provided between the insertion apparatus and a cable.

Figure 5:
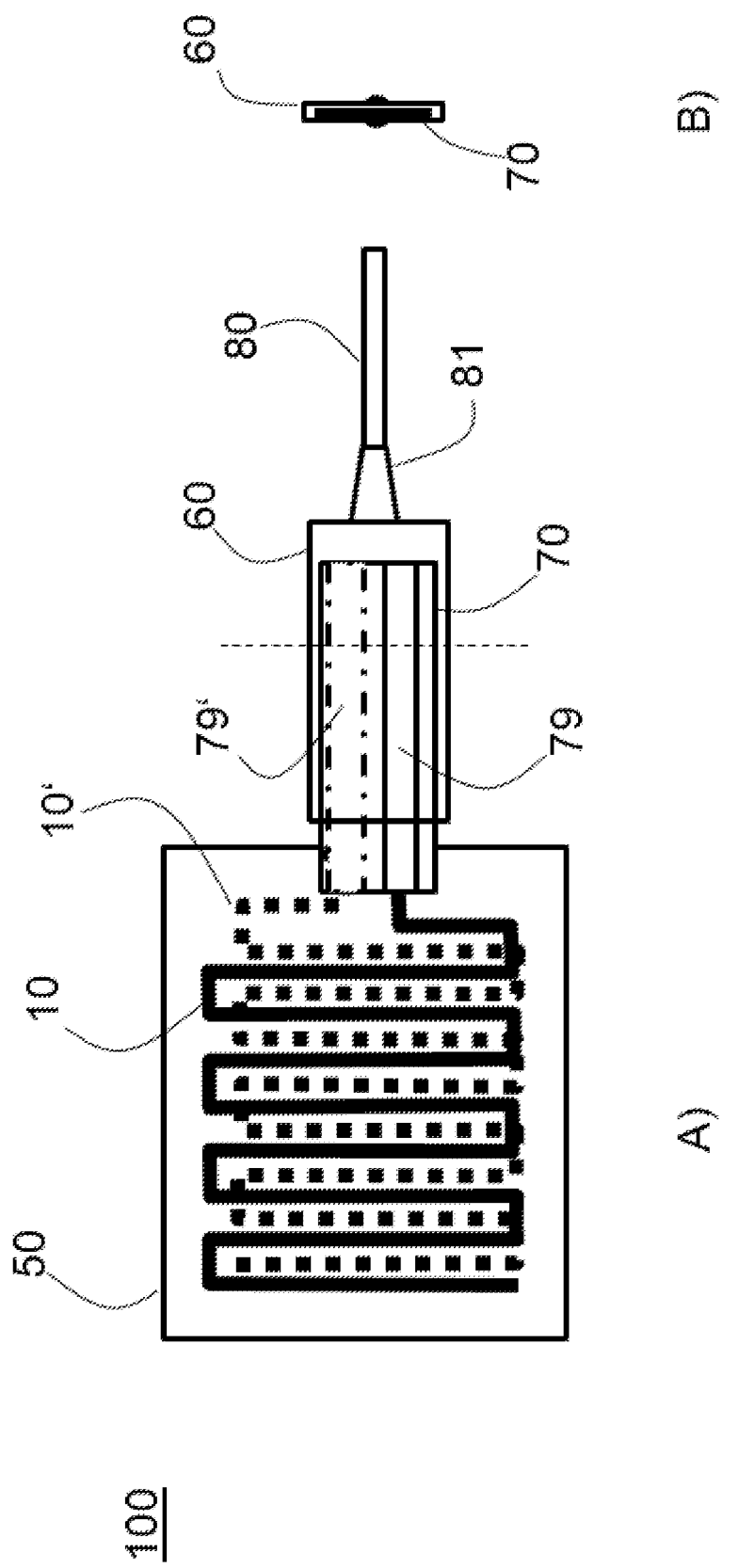
FIG. 5A: shows a plasma applicator with an electrotechnical core and with a plug-in apparatus, which is brought together with an insertion apparatus.
FIG. 5B: shows a side view of a section along the width through the plug-in apparatus brought together with the insertion apparatus.

FIG. 5A shows a plasma applicator 100 with an electrotechnical core 50 and a plug-in apparatus 70. The electrotechnical core 50 comprises a second electrode structure 10 and a first electrode structure 10'. The second electrode structure 10 is preferably driven during operation by an applied voltage signal and the first electrode structure 10' is preferably grounded. The electrode sections of the second electrode structure 10 and of the first electrode structure 10' are arranged above one another with a defined overlap. Advantageously, the electrode sections of the grounded electrode structure and the electrode structure driven during operation are arranged with such an offset from one another that an electric field advantageous for the plasma ignition forms. Preferably, the electrode sections of corresponding electrode structures respectively overlap in a comparatively small region. That is to say, the respective remaining region of the electrode sections, which is not in overlap with an electrode section of a further electrode structure, is significantly larger in comparison with the overlapped region. A substantially homogeneously distributed plasma is generated by way of a comparatively small overlap between the electrode structures.

The plug-in apparatus 70 is securely connected to the electrotechnical core 50 and comprises a first conductor track 79' and a second conductor track 79. The first conductor track 79' is connected in electrically conductive fashion to the first electrode structure 10' and the second conductor track 79 is connected in electrically conductive fashion to the second electrode structure 10. By way of example, the first and second conductor tracks can be embodied as simple conductors. The first and second conductor tracks preferably consist of the same material as the electrode structures. The plug-in apparatus 70 preferably has a width of 3 cm, height of 1 mm and a length of 10 cm. In the illustration shown, the plug-in apparatus 70 has been brought together with an insertion apparatus 60. The insertion apparatus 60 is connected via a cable 80 to a power supply unit, such as a high-voltage generator, used in predominantly stationary fashion and not shown here. The cable 80 comprises kink protection 81 on the side facing the insertion apparatus 60. FIG. 5B shows a side view of a section along the height through the insertion apparatus.

Figure 6:
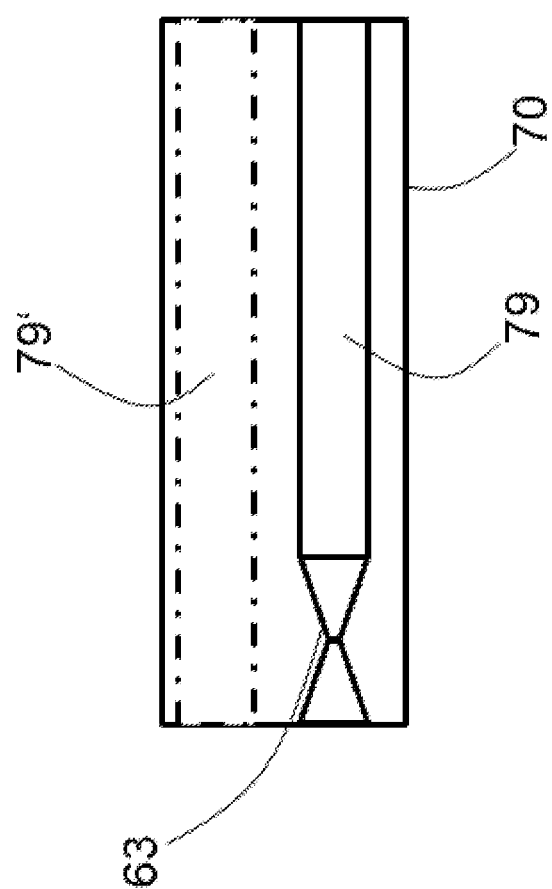
FIG. 6: shows a plug-in apparatus in the chip card format with a taper in a conductor track.

FIG. 6 shows a plug-in apparatus 70 with a second conductor track 79, which is electrically connected to an electrode structure driven during operation (not shown), and a first conductor track 79', which is electrically connected to a grounded electrode structure (not shown). The second conductor track 79 has a taper 63 at one point. The smaller diameter of the conductor track at the taper 63 yields a higher electrical resistance than in the remainder of the conductor track 79. As a matter of principle, the taper 63 shown can be integrated both in the plug-in apparatus 70 and in the electrotechnical core 50. To ensure single use of a plasma applicator 100, a current pulse can be applied to the conductor track 79 at the end of a treatment, the current intensity of which is rated such that the conductor track 79 heats up so far at this taper 63 that the latter melts. By way of example, a power supply unit brought together with the plasma applicator can automatically emit an excessive current pulse with a corresponding current intensity for significantly less than 1 second at the end of the plasma treatment.

FIG. 7 shows an exploded view of an already known apparatus 1 for generating a cold atmospheric pressure plasma for the treatment of surfaces with a multilayer system 2. The multilayer system 2 forms a plasma applicator and comprises the following layered structures, specifically (starting from the bottom):
 a first insulating structure 11,
 a first electrode structure 12,
 a dielectric layer 13,
 a second electrode structure 14,
 a second insulating structure 15,
 a spacer structure 16, and
 an adhesion layer 17.

The first insulating structure 11, the first electrode structure 12, the dielectric layer 13, the second electrode structure 14, and the second insulating structure 15 each form a layer of the electrotechnical core of the plasma applicator. Here, the first insulating structure 11 is arranged on the side 4 of the multilayer system 2 facing away from the surface to be treated and it has a height of between 0.5 mm and 2.5 mm, preferably 2 mm. The first insulating structure 11 substantially serves to insulate the first electrode structure 12, which is preferably embodied as a high-voltage layer, i.e., an electrode structure to which a high voltage is applied.

The dielectric layer 13 is arranged between the first electrode structure 12 and the second electrode structure 14, with the second electrode structure 14 preferably being embodied as a ground electrode layer. Here, the dielectric layer 13 substantially prevents a short circuit, in particular in the form of an arc, between the first and the second electrode structure.

Furthermore, a second insulating structure 15 with a thickness of between 50 µm and 300 µm is arranged on the second electrode structure 14 in a preferred configuration.

Then, the spacer structure 16, which ensures provision of a sufficient gas volume that allows a plasma to ignite, is arranged above the second electrode structure 14 or the second insulating structure 15, i.e., on the side 3 of the multilayer system 2 facing the surfaces to be treated.

Finally, an adhesion layer 17 with a thickness of between 100 µm and 300 µm, preferably 200 µm, which is in direct contact with the surface to be treated is arranged on the side 3 of the multilayer system 2 facing the surface to be treated and above the spacer structure 16. Preferably, the adhesion layer 17 then is formed with a skin- and/or wound-compatible material, preferably with antiseptic and/or atraumatic properties.

In the present case, as illustrated in FIG. 7, the second electrode structure 14 is formed with a multiplicity of cutouts, in particular in a mesh-like manner. In further embodiments, the cutouts could, however, also be embodied in the form of holes, stripes, meanders, honeycombs, circles and/or squares.

Furthermore, the spacer structure 16 can also have a honeycomb shape, wherein the spacer structure 16 can also be realized by projections or webs. Possible materials for the spacer structure 16 include polymers, elastomers and/or silicones or the like. In principle, a multiplicity of possible materials can be used, such as inorganic or organic materials, in particular natural and/or synthetic materials, such as thermoplastics, thermosetting plastics and/or elastomers. In respect of further possible materials, reference is also made in exemplary fashion to the book "Kunststoff-Taschenbuch" (28th edition) by Karl Oberbach and Hansjürgen Saechtling. In a preferred configuration of the apparatus shown in FIG. 7, the spacer structure is formed with projections and/or webs, which have a height of between 0.5 mm and 5 mm.

Overall, the multilayer system illustrated in FIG. 7 has a thickness of 2 mm to 4 mm. Here, provision is made for the layers which are in direct contact with the surface to be treated to be formed by a heat-resistant, biocompatible and chemically resistant plastic.

Figure 8C:
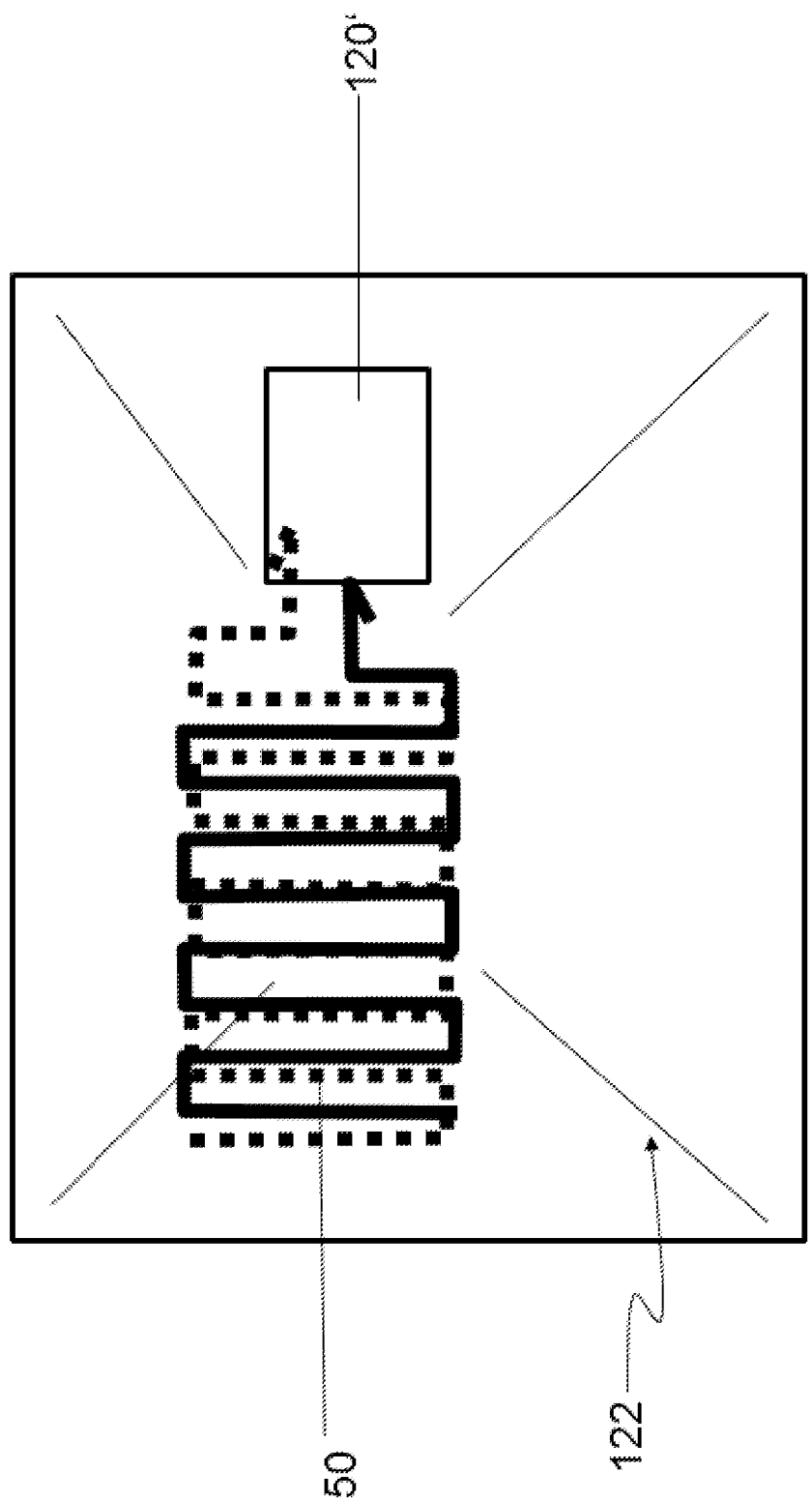
FIG. 8C shows a plasma applicator with an integrated mobile power supply unit without a plug-in apparatus.

FIGS. 8A, 8B and 8C show a plasma applicator with a mobile power supply, which is ensured by a power supply unit that is comparatively small in relation to the plasma applicator. On account of the mobile power supply unit, it is not necessary to connect a power supply unit predominantly used in stationary fashion, such as a high-voltage generator, to the plasma applicator via a cable in order to transmit a voltage signal sufficient to ignite a plasma to the electrode structure and to ignite a plasma. The power required to ignite a plasma is provided by an energy store comprised in the mobile power supply unit. By way of example, such an energy store can be a battery, an accumulator or a capacitor.

The plasma applicator shown in FIGS. 8A to 8F comprises at least a first electrode structure and a second electrode structure. At least one insulation layer is arranged between the electrode structures in each case. By way of example, the insulation layer can be a polymer with dielectric properties. The distance between the electrode structures is preferably less than 1 mm. Advantageously, a lower amplitude of the voltage signal is required to ignite the plasma on account of the small distance. In place of the shown meandering shape of the first electrode structure and of the second electrode structure, the electrode structures could also have a spiral shape, could be continuous or could have holes. The electrode structures consist of a metal in the embodiment shown. In different variants of the embodiment shown, electrode structures made from a conductive plastic or from a textile with conductive wires are provided. On the side facing the surface to be treated, the shown plasma applicator has an insulation layer made of a polymer, which is preferably formed from a biocompatible material, as a protective layer.

Optionally, the plasma applicator shown can also comprise a spacer structure. A corresponding spacer structure can be made of, e.g., a polymer, textile, hydrogel, on the basis of starch, for example as corn puffs, standard wound fleece or gauze and an absorber and can be electrically insulating and, in particular, biocompatible. A spacer structure can also be formed by a combination of the aforementioned materials. A spacer structure can also be embodied in the form of a ribbon cable for igniting a plasma. In particular, the spacer structure can be embodied as a ribbon cable which is a plasma source at the same time.

Optionally, the plasma applicator shown has at least one insulation layer as a protective layer on the side facing away from the surface to be treated.

On the side facing the surface to be treated, the plasma applicator shown can have an adhesion layer or a sticker for fixing the plasma applicator over or on the surface to be treated.

In addition to the shown rectangular form, the electrotechnical core of the plasma applicator could also have alternative geometries. In different variants, the electrotechnical core of the plasma applicator has a circular shape, a shape specifically adapted to a certain body part (e.g., a foot) or the shape of a cylinder. In one variant, the plasma applicator is provided to be attached in conical form around a tube or a cable. In this case, the plasma applicator is placed around a tube or a cable such that a sealed gas space is created under a plasma applicator with the shape of a cone. Advantageously, an access laid thus need not be removed in order to facilitate treatment with a plasma applicator. If it is known before an access is laid that a treatment with a plasma applicator should be carried out, it may be advantageous if a plasma applicator has a hole or a slot through which a cable or a tube can be guided. As a result, an access can be laid first and a plasma treatment can occur at a later time without the access having to be removed.

The variants of a mobile power supply for a plasma applicator described below with reference to FIGS. 8A to 8F or the variants of those features that should ensure single use of a plasma applicator can be combined in combination with electrotechnical cores of any of the aforementioned geometries or other geometries to form different variants of the plasma applicator. In particular, an electrotechnical core can comprise a first insulation layer, followed by a first, grounded electrode structure, followed by a second insulation layer, followed by a second electrode structure driven during operation, followed by a third insulation layer, followed by a third, grounded electrode structure and can consequently already ensure contact protection per se.

FIG. 8A shows a plasma applicator with a plug-in apparatus 70, which has been brought together with an insertion apparatus 60 of a mobile power supply unit 110. The comparatively small mobile power supply unit 110 comprises an energy store and an insertion apparatus. In contrast to the variants of an insertion apparatus described with respect to FIGS. 1, 2, 3 and 5, the insertion apparatus of a mobile power supply need not be arranged at the end of a relatively long cable provided for connection to a power supply unit, such as a voltage generator, which is predominantly used in stationary fashion. The mobile power supply unit 110 can be mechanically and electrically connected to the plug-in apparatus 70 of a plasma applicator by means of the insertion apparatus 60. The plug-in apparatus 70 shown and/or the electrotechnical core 50 can have variants of those features that ensure single use, as are described in relation to FIGS. 4 and 6, for example. In the connected state, the plasma applicator and the mobile power supply unit form a compact unit, which can be easily carried by a patient, even during operation.

The energy store of the mobile power supply unit 110 typically does not supply a voltage signal in the kV range, but a voltage signal of a few volts, for example between 5 and 20 volts. The provided voltage signal can be of the order of a voltage provided by a commercially available battery, e.g., 9 V of a 9 V block. However, since, as a rule, a voltage signal with an amplitude of several hundred volt up to 10 kV is required to ignite a plasma, the voltage signal supplied by the energy store of the mobile power supply unit must be transformed into a voltage signal of several hundred volt up to 10 kV.

To this end, the plasma applicator in the embodiment described here furthermore comprises an electrical circuit (not shown), which transforms a voltage signal provided by the mobile power supply unit 110 into a (pulsed) AC voltage in a voltage range between preferably a few 100 V and 10 kV. An electrical circuit embodied to this end comprises, e.g., an inverter or a VDC-VAC inverter in combination with a voltage transformer and a pulser with, e.g., a pulsed duty cycle of 1 s "on" and 9 s "off". Depending on use, a plasma applicator not shown here can have a deviating pulsed duty cycle. The electrical circuit is electrically connected to at least one electrode structure of the plasma applicator and is suitable to supply an amplitude of the voltage signal sufficiently high to ignite a plasma to the electrode structure.

Alternatively, the electrical circuit for transforming a voltage signal with 5-20 V into a voltage signal with an amplitude of several 100 V to 10 kV can also be integrated in the mobile power supply unit, together with the energy store and the insertion apparatus. The energy store of the mobile power supply unit supplies a voltage signal which is transformed by the corresponding electrical circuit, integrated in the power supply unit, into a voltage signal with a corresponding amplitude that is sufficient to ignite a plasma. If the insertion apparatus of the mobile power supply unit is connected to the plug-in apparatus of a plasma applicator, the voltage signal can be transmitted via conductor tracks of the plug-in apparatus to at least one electrode structure for igniting a plasma. Then, the plasma applicator itself requires no electrical circuit for transforming a voltage signal into a voltage signal with an amplitude in the kV range.

In an embodiment not shown here, an electrical circuit is integrated into each of a mobile power supply unit and a plasma applicator. If a plug-in apparatus of the plasma applicator is plugged together with an insertion apparatus of the mobile power supply unit and an electrical and mechanical connection has been established, the two electrical circuits form a circuit system. Then, the circuit system transforms a DC voltage of the energy store of the mobile power supply unit into a voltage signal sufficient to ignite a plasma and guides the voltage signal to at least one electrode structure in the electrotechnical core.

If the energy store in the mobile power supply unit 110 is an accumulator, it is preferable for the accumulator to have an embodiment that is as flat as possible and, e.g., have a length of 9 cm, a width of 9 cm, and a height of 0.2 cm. A corresponding accumulator preferably has a high capacity, preferably more than 4000 mAh, and a high current output of more than 500 mA, in particular between 1 and 2 A. Alternatively, a number of smaller accumulators can also be connected in parallel in order to be able to generate a sufficiently high current.

When transforming a DC voltage into a voltage signal sufficient to ignite a plasma, a voltage is typically increased by a factor of 100 or more. In turn, this means a reduction in a current delivered to a secondary coil of a transformer by a factor of 100. Using an energy store formed by a plurality of accumulators connected in parallel, it may be possible to output a comparatively high current over a short period of time, without the energy store becoming too hot in the process. Using such an energy store, which can output high current within a short period of time without becoming hot in the process, may be advantageous because currents in the milliampere range up to the ampere range may briefly arise during a plasma discharge.

The energy store of the mobile power supply unit 110 can also be a capacitor. Here, in particular, the size or the weight and the capacitance of the capacitor used are decisive. Preferably, the capacitor used has a weight of a few grams, a compact size in the range of a few centimeters, a capacitance in the range of $\mu F$ to mF, and a half life of the discharge of effectively a few seconds. The capacitor can be charged via the insertion apparatus of the mobile power supply unit by way of a connection with a power supply, for example a charging device. When the insertion apparatus is connected to a plug-in apparatus, the energy stored in the capacitor can be delivered in the form of a voltage signal sufficient to ignite a plasma to an electrode structure of the plasma applicator via conductor tracks in the plug-in apparatus by means of an electrical circuit integrated into the insertion apparatus or into the plug-in apparatus. Advantageously, at least one electrical component, preferably an electrical resistor, is connected in series or else in parallel between the capacitor and the conductor track in the plug-in apparatus in order to restrict the discharge current from the capacitor.

By connecting the mobile power supply unit to a plasma applicator and a resultant voltage transfer to at least one electrode structure of the plasma applicator, a patient is able to ignite a plasma any time and anywhere after the plasma applicator has been applied above the wound. Thus, the patient is independent of a power supply that is predominantly used in stationary fashion and is dependent on a local current supply and can use the plasma applicator for a plasma treatment anywhere with the aid of the mobile power supply unit.

Advantageously, a mobile power supply unit 110 as shown in FIG. 8A is reusable. In particular, this even holds true if the plasma applicator itself can only be used once.

FIG. 8B shows a plasma applicator with an integrated power supply unit 110' and a plug-in apparatus 70. Thus, the mobile power supply unit 110' is integrated in the plasma applicator in the embodiment shown. The electrotechnical core 50 of the plasma applicator is electrically connected to the integrated power supply unit 110' by means of a contact 112. Furthermore, the plasma applicator comprises a plug-in apparatus 70. Should the mobile power supply unit comprise an accumulator or capacitor, the latter can be connected to and charged by a mobile or stationary power supply by way of the plug-in apparatus. Once the accumulator or capacitor has been sufficiently charged, it is possible to sever the connection to the power supply. Then, a patient can move independently of a stationary power supply and can ignite a plasma independently of a stationary power supply anywhere and at a later time.

A single use of the plasma applicator shown can be ensured by virtue of the plug-apparatus or the electrotechnical core having variants of those features ensuring single use, for example as described in relation to FIGS. 4 and 6. An electrotechnical core can comprise, in particular, a first insulation layer, followed by a first, grounded electrode structure, followed by a second insulation layer, followed by a second electrode structure driven during operation, followed by a third insulation layer, followed by a third, grounded electrode structure, and can consequently already ensure contact protection per se.

FIG. 8C shows a plasma applicator with integrated power supply unit 120' and without a plug-in apparatus. The integrated power supply unit 120' is electrically connected to the electrotechnical core 50 of the plasma applicator. The plasma applicator shown comprises a mobile power supply unit 120', integrated into the plasma applicator, with an energy store.

In contrast to the embodiments shown in FIGS. 8A and 8B, the shown plasma applicator has no plug-in apparatus.

By way of example, the energy store can be a battery with a capacity of between 0.5 and 20 Ah, e.g., a commercially available 9 V block. The DC voltage provided by the energy store is transferred to an electrical circuit integrated in the plasma applicator and transformed into a voltage signal there, preferably with an amplitude in the kV range. To ignite a plasma, a voltage signal with an amplitude of several hundred volt may also be sufficient. The transformed voltage signal is then transmitted to the at least one electrode structure for the purposes of igniting a plasma.

Single use of the plasma applicator can likewise be ensured by way of a power supply unit which is integrated in the plasma applicator and has an energy store with a limited charge that cannot be recharged.

Single use of the shown plasma applicator with the integrated power supply unit 120' can be ensured by virtue of a conductor track for transmitting a voltage signal sufficient to ignite a plasma to an electrode structure having a taper, for example as described in relation to FIG. 6. In the region of the taper, the conductor track has a higher electrical resistance than the remainder of the conductor track. At the end of the treatment, the power supply unit can provide a current pulse, the current intensity of which is rated such that the conductor track heats to such an extent at the taper that it melts in the region of the taper.

The energy stored in the energy store, e.g., a battery, of the integrated power supply unit can also be rated precisely to such an extent that it only suffices for single treatment. A single treatment typically has a duration of a few minutes.

The plasma applicator shown also comprises a spacer structure 122.

FIG. 8D shows a plasma applicator with an insertion slot 130 for a mobile power supply unit 110'. In the embodiment shown, the plasma applicator has an insertion slot 130 on the upper side, i.e., the side facing away from a wound, by means of which a mobile power supply unit 110' can be fastened to the plasma applicator. The plasma applicator comprises contacts 112, which connect an electrode structure of the electrotechnical core 50 to the upper side of the plasma applicator. In particular, the contacts 112 at the surface have exposed contact areas, by means of which it is possible to establish galvanic coupling with the energy store of the mobile power supply unit 110' when the mobile power supply unit 110' is inserted into the insertion slot 130 of the plasma applicator.

In the embodiment shown, the energy store of the mobile power supply unit is an accumulator. Advantageously, charging an empty accumulator allows the mobile power supply unit to be used multiple times for supplying power to a plasma applicator. Furthermore, the mobile power supply unit comprises an electrical circuit which is embodied to transform a DC voltage provided by the accumulator into a voltage signal sufficient to ignite a plasma.

In the embodiment shown, the mobile power supply unit comprises no insertion apparatus. Therefore, a charging apparatus integrated in the mobile power supply unit is provided for charging the accumulator. In the exemplary embodiment shown, the charging apparatus comprises a receiver coil arrangement for inductively charging the accumulator.

It is also conceivable that an energy store of a power supply unit can be charged by way of contacts. By way of example, a mobile power supply unit can be inserted into an insertion slot, provided therefor, of a stationary power supply unit and the energy store of the power supply unit can be charged by way of contacts. It is also conceivable for a charging device to have insertion slots, into which a power supply unit can be inserted in order to establish electrical contact between the energy store and a power supply of the charging device.

Figure 8E:
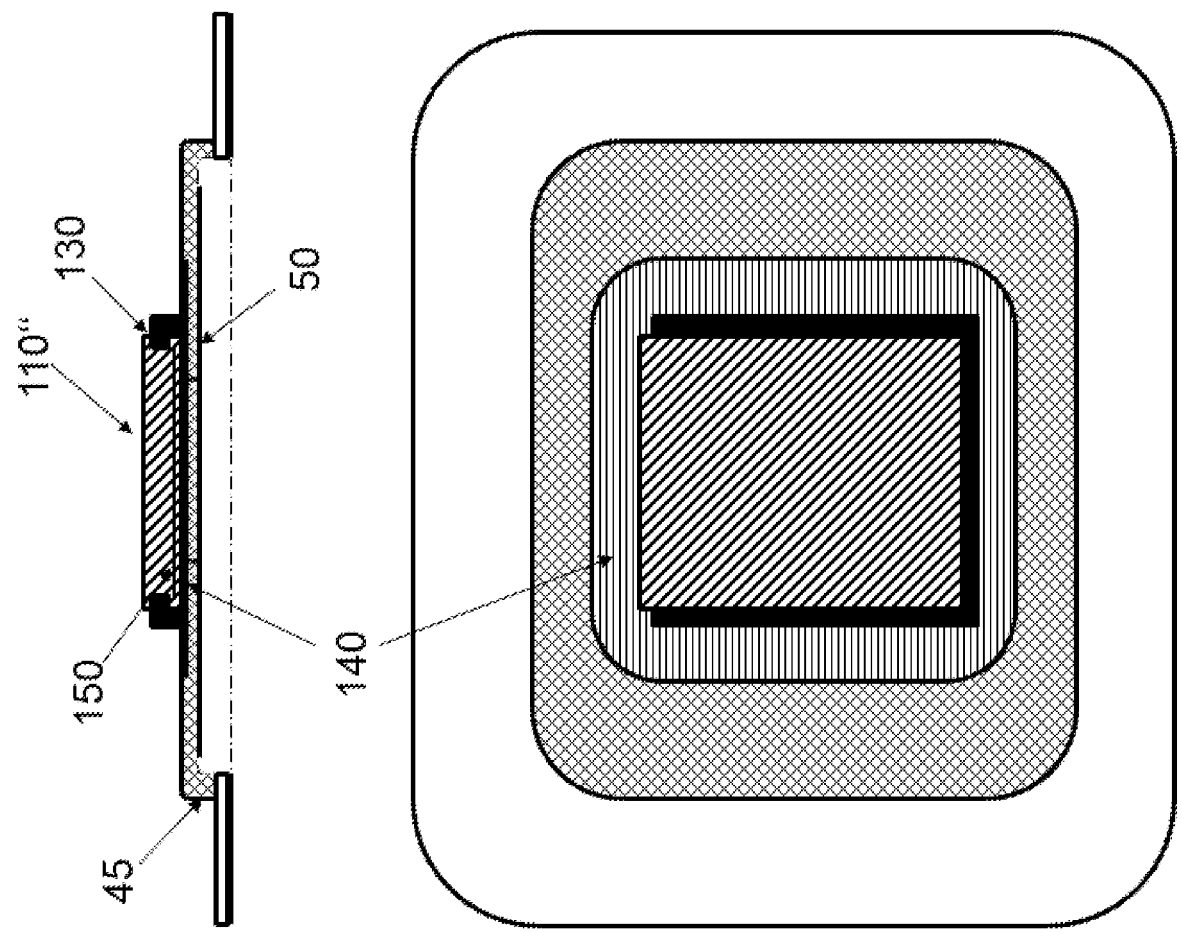
FIG. 8E shows a plasma applicator with an integrated receiver coil arrangement and with an insertion slot into which a mobile power supply unit with a transmitter coil arrangement can be inserted.

FIG. 8E shows a plasma applicator with an integrated receiver coil arrangement 140 and with an insertion slot 130, into which a mobile power supply unit 110" has been inserted. The insertion slots 130, into which a mobile power supply unit 110" has been inserted, are situated on the side of the plasma applicator facing away from the surface to be treated. On the side of the mobile power supply unit facing the side of the plasma applicator facing away from the surface to be treated, the mobile power supply unit comprises a transmitter coil arrangement 150, which transfers electrical energy provided by an energy store (not shown) integrated in the mobile power supply unit 110" to the receiver coil arrangement 140 of the plasma applicator by means of inductive coupling. Thus, the mobile power supply unit 110" has an energy store (not illustrated) which provides the energy which is transferred from the transmitter coil arrangement 150 to the receiver coil arrangement 140 by means of inductive coupling.

It is also conceivable for the power supply unit 110" not to be a mobile power supply unit and not to have an energy store. By way of example, such a power supply unit can be connected to a cable, which is connected to a stationary power supply unit at the other end.

In this case, power is provided by way of a stationary power supply unit, said power being transferred by means of inductive coupling from the transmitter coil arrangement 150 to the receiver coil arrangement 140.

The electrotechnical core 50 is situated on the side of the plasma applicator facing the surface to be treated and electrically connected by means of contacts to a flat receiver coil arrangement 140 situated thereabove. The receiver coil arrangement 140 is situated on the side of the plasma applicator facing away from the surface to be treated and completely covered by an enclosure 45 of the plasma applicator. By way of example, the enclosure 45 of the plasma applicator can be produced using an injection molding method.

Advantageously, the plasma applicator of the embodiment shown can be completely over-molded by an enclosure 45. In particular, there are no exposed electrical contacts. Consequently, it is easy to clean, disinfect and/or sterilize the plasma applicator.

FIG. 8F shows a plasma applicator with an integrated power supply unit 120" with an energy store, which can be charged by means of a likewise integrated, inductive charging apparatus 160.

In the embodiment shown, the electrotechnical core 50 is situated on the side of the plasma applicator facing the surface to be treated and electrically connected by means of contacts 112 to a rechargeable energy store integrated in the plasma applicator. By way of example, the rechargeable energy store can be an accumulator or a capacitor.

On its upper side, the energy store has two separate contacts 114, which electrically connect the energy store to the charging apparatus 160, in particular a receiver coil arrangement. Inductive coupling allows electrical energy to be transmitted from a commercially available charging station to the charging apparatus 160 for the purposes of charging the energy store. An electrical circuit is integrated in the energy store and embodied to transform a DC voltage signal provided by the energy store into a voltage signal sufficient to ignite a plasma. The transformed voltage signal is then transmitted by means of electrical contacts 112 to the at least one electrode structure in the electrotechnical core 50.

Figure 9:
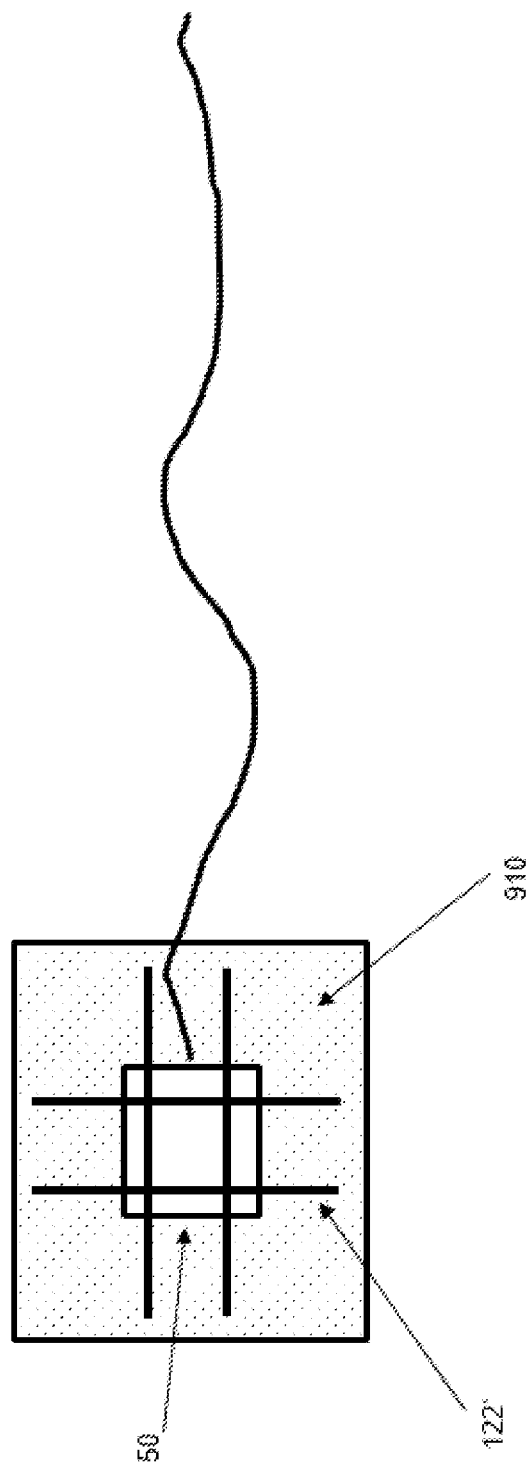
FIG. 9 shows a plasma applicator with a scalable treatment area.

FIG. 9 shows a plasma applicator with an electrotechnical core 50, which can be combined with variants of those features that ensure single use and with the described variants for a mobile power supply. The electrotechnical core 50 can comprise, in particular, a first insulation layer, followed by a first, grounded electrode structure, followed by a second insulation layer, followed by a second electrode structure driven during operation, followed by a third insulation layer, followed by a third, grounded electrode structure and can consequently already ensure contact protection per se.

The plasma applicator shown comprises a scalable spacer structure 122'. The scalable spacer structure 122' can consist of, e.g., silicone, plastic or textile and has a support function for a wound covering 910, in order to establish a defined distance between the surface to be treated and the side of the plasma applicator facing the surface to be treated. As a result of a scalable spacer structure, a plasma applicator can be adapted to different wound sizes, for example by tearing or cutting a spacer structure. In principle, all mechanical separation tools and methods available in the clinic or in outpatient care can be used to adapt the size of a spacer structure to a wound size. The plasma applicator itself remains untouched by the scaling process. In the embodiment shown, the spacer structure is gas-permeable and flexible. The size of the spacer structure can be adapted to a final shape by cutting or an alternative process by a user.

Optionally, a plasma applicator can be fastened to a spacer structure by way of defined connections, by clamps or an adhesive or by adhesive spots provided on the surface of a spacer structure. A spacer structure preferably has a mesh-shaped embodiment and has a region in the center where the electrotechnical core is arranged or can be fastened. Preferably, a greater number of mesh structures are provided in this region such that the plasma applicator has a sufficiently secure hold on the spacer structure. By way of, e.g., a wound plaster, an adhesive film, a shower plaster, a gauze bandage or other dressing material, the spacer structure connected to a plasma applicator and adapted to the wound size can be affixed over or on the wound such that a sealed gas space arises around the plasma applicator and the spacer structure, between the surface to be treated and the wound covering 910.

FIG. 10A shows a spacer structure 200 which is a dielectric barrier discharge (DBD) at the same time. The spacer structure has the shape of a plurality of adjoining honeycombs. As shown in relation to a section 210 of a honeycomb of the spacer structure, an ignited plasma 220 (indicated by the hatched region) propagates at the edges of a honeycomb 210. By way of example, a spacer structure can be made from a 2-core ribbon cable. FIG. 10B shows a cross section of the spacer structure 200. Here, the driven electrode structure 230 and the counter electrode 240, which is typically at reference potential, are visible. Then, a plasma respectively burns to the right and to the left of the cable or within and outside of the honeycomb.

FIG. 11 shows a closed circuit 300, which comprises a two-core cable. The closed circuit 300 has connection points 310, which could be, e.g., an adhesive point, a weld point, a solder point. The sheaths of the two cables are securely connected to one another at the connection points 310. The electric circuit 300 shown in FIG. 7 represents a possibility of how a spacer of a spacer structure can be constructed from ribbon cables. Here, the cable sections are upright, and so the plasma burns to the right and left of the cable as shown in FIG. 10B. The cable sections are wavy; a closed circuit 300 is completely autonomous of other closed circuits, e.g., 300' and 300", which are each formed by a different cable. All cables are in electrical contact with one another at a longitudinal side of the electrode structure formed by the cables. The shape is chosen so as to be able to be produced as easily as possible with little manufacturing outlay.

Figure 12:
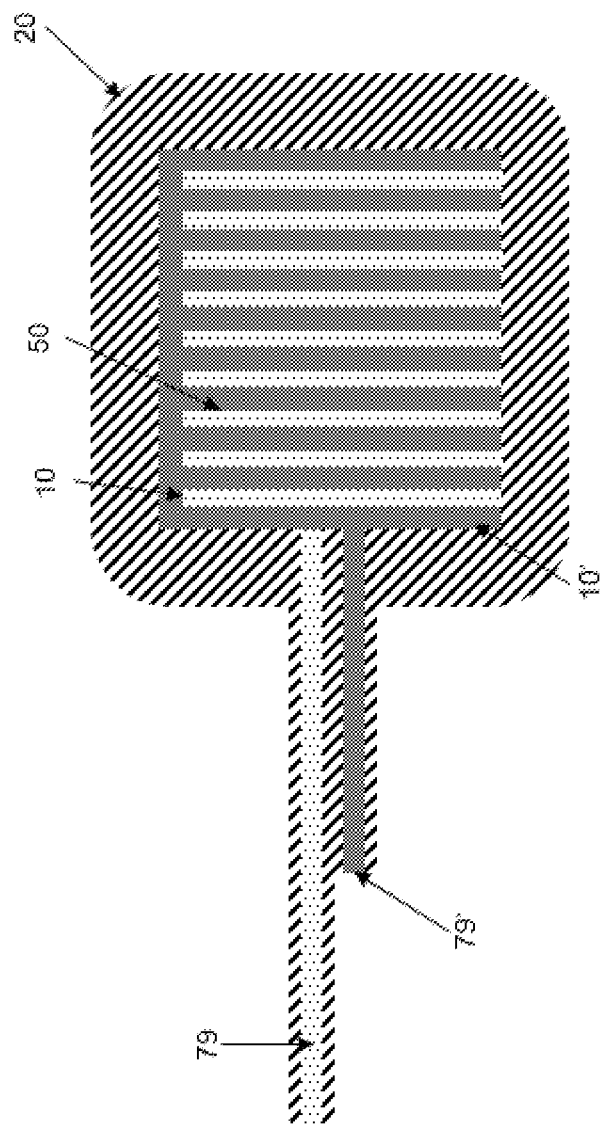
FIG. 12 shows a plan view of the side facing a patient of an electrotechnical core.

FIG. 12 shows a plan view of the side of an electrotechnical core 50 facing a surface to be treated and having an insulation layer 20, which is arranged between a driven electrode structure 10 and a counter electrode 10'. The conductor tracks 79, 79' are electrically connected to the driven electrode structure 10 and the counter electrode 10', respectively, and are conductor tracks of a chip card-shaped plug-in apparatus.

Figure 13:
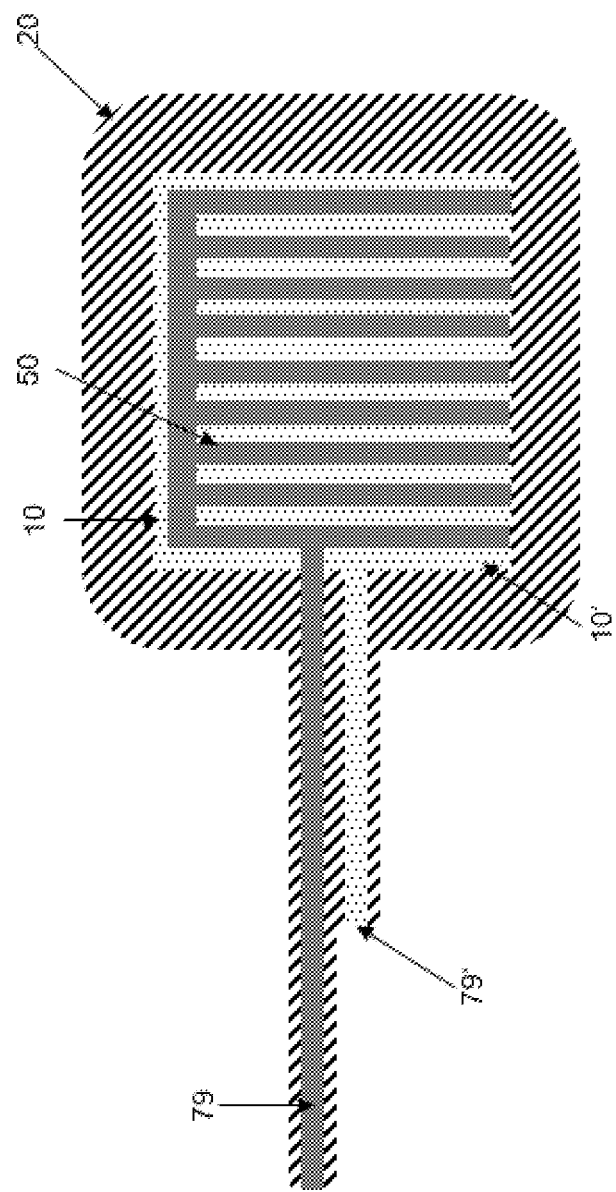
FIG. 13 shows a plan view of the side facing away from a patient of the electrotechnical core as shown in FIG. 12.

FIG. 13 shows a plan view of a side of the electrotechnical core 50, shown in FIG. 12, facing away from the surface to be treated and having an insulation layer 20, which is arranged between an electrode structure 10 that is driven by a voltage signal and a counter electrode 10'. One of the conductor tracks 79, 79' is electrically connected to the driven electrode structure 10 and the counter electrode 10', respectively, and are conductor tracks of a chip card-shaped plug-in apparatus.

Figure 14:
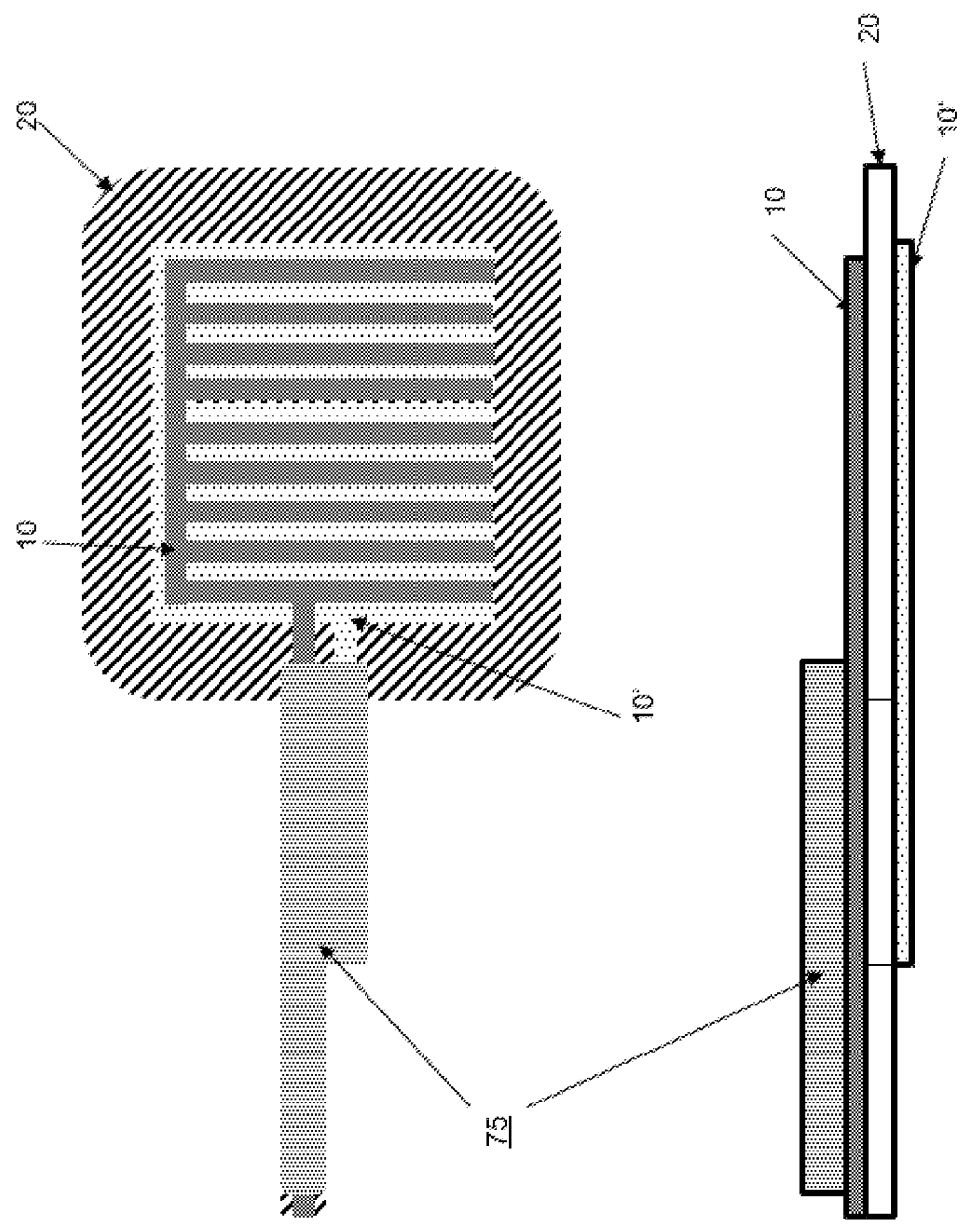
FIG. 14 shows a plan view of the side facing away from a patient of the electrotechnical core as shown in FIG. 13.

FIG. 14 shows a plan view of the side of the electrotechnical core 50, shown in FIG. 13, facing away from the surface to be treated and having an insulation layer 20, which is arranged between a driven electrode structure 10 and a counter electrode 10'. In the shown illustration, a chip card-shaped reinforcement 75 is glued, laminated, adhesively bonded, etc. onto the conductor tracks 79, 79' of the plug-in apparatus. The counter electrode 10' is situated on the side facing the surface to be treated.

Figure 15:
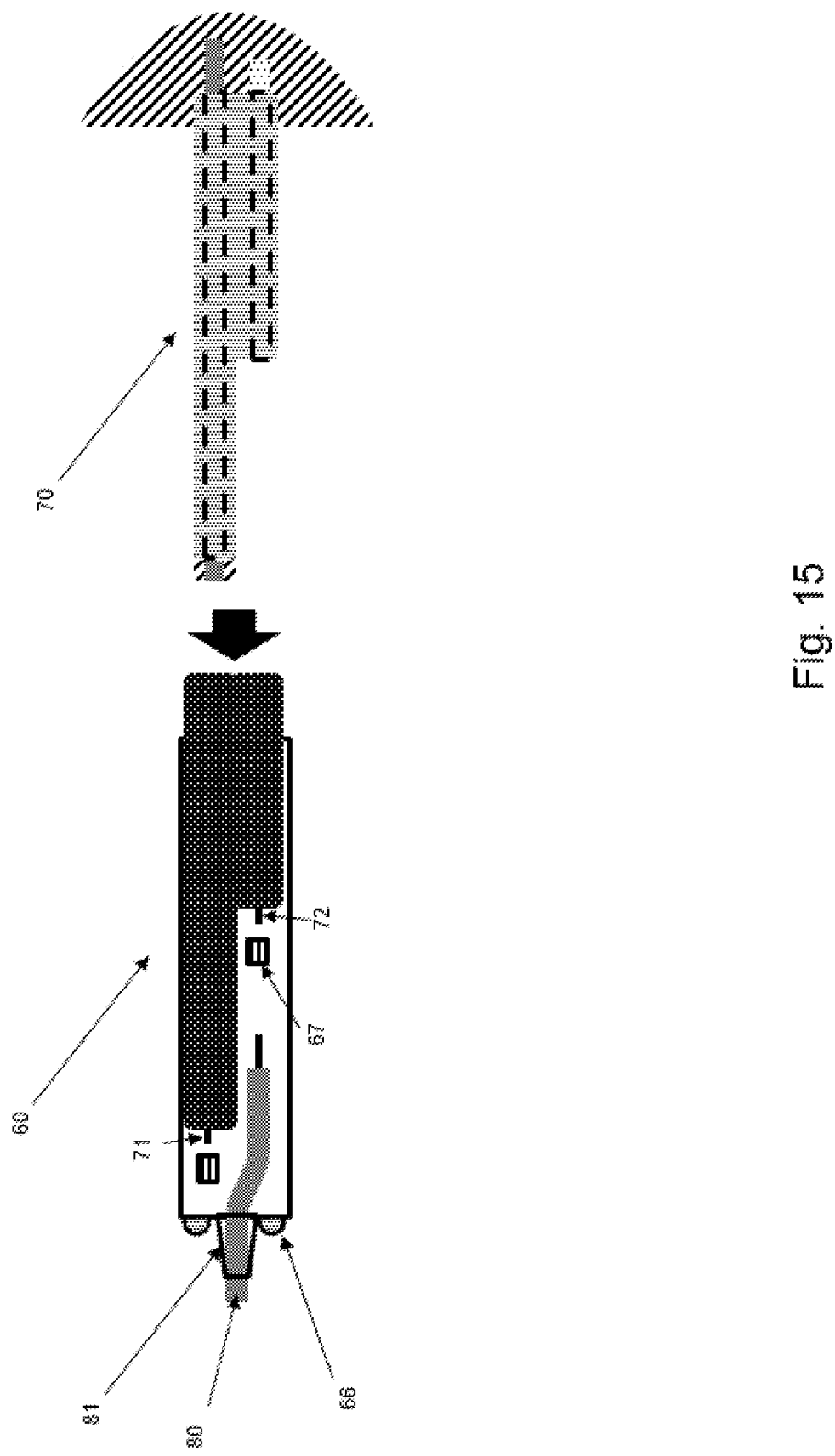
FIG. 15 shows an insertion apparatus with a voltage connector and a ground connector, FIG. 16 indicates how a mechanically secure seat can be established between a plug-in apparatus and an insertion apparatus indicated by snap-in elements.

FIG. 15 shows an insertion apparatus 60 with a voltage connector 71 and a ground connector 72. Furthermore, the insertion apparatus 60 comprises inductors 67 and sealing plugs 66. The insertion apparatus 60 is connected via a multiply shielded cable 80 to a power supply unit, not shown. Kink protection 81 is provided to stabilize the cable 80. FIG. 15 indicates how a plug-in apparatus 70 is inserted into the insertion apparatus 60 in order to transmit a voltage signal provided by a power supply unit to an electrode structure (not shown) that is driven by the voltage signal.

Figure 16:
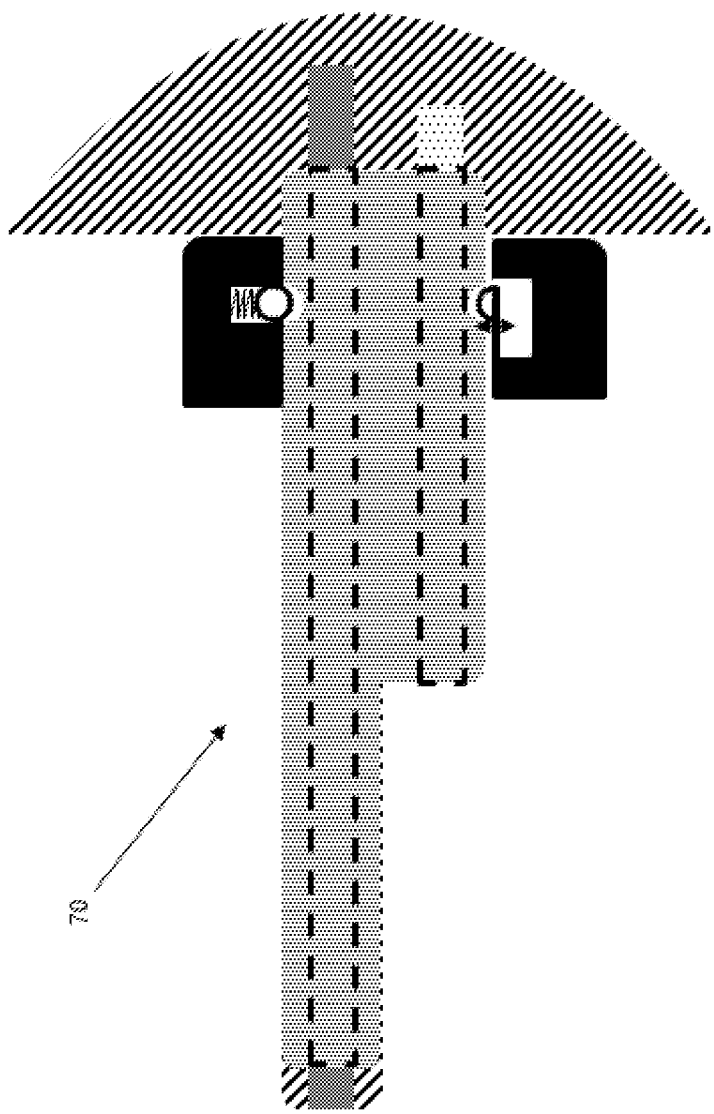

FIG. 16 indicates how a mechanically secure seat can be established between a plug-in apparatus 70 and an insertion apparatus, merely indicated by snap-in elements in this case. In the shown embodiment, a mechanically secure seat is realized by way of a spring with a ball on both sides of an insertion apparatus and a corresponding cutout in the plug-in contact apparatus 70. In an embodiment not shown here, a spring arm with an appropriately fitting bulge could also latch into a cutout provided therefor.

Figure 17:
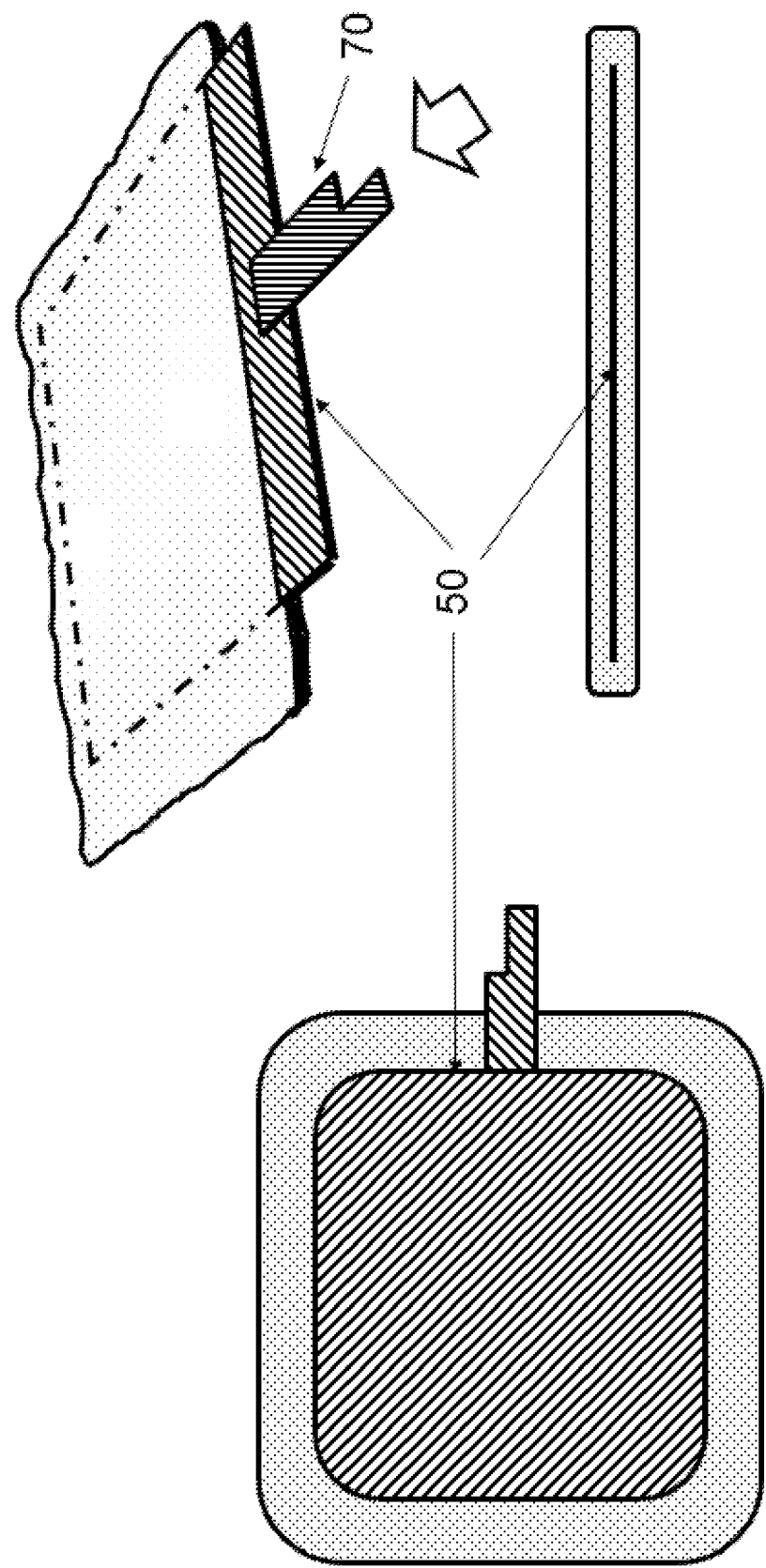
FIG. 17 shows an electrotechnical core which has been inserted into an absorbent pad.

FIG. 17 shows an electrotechnical core 50, which has been integrated into an absorbent pad. In an embodiment not shown here, a pad is pressed or sewn around an electrotechnical core. In this case, the pad represents the enclosure of the electrotechnical core. Preferably, the electrotechnical core 50 is completely enclosed by gauze or a pad and/or a textile. In an embodiment not shown here, the upper side (facing away from the body) is sealed in air-tight fashion by way of a film and an adhesion layer is applied to the side facing the surface to be treated.

Figure 18:
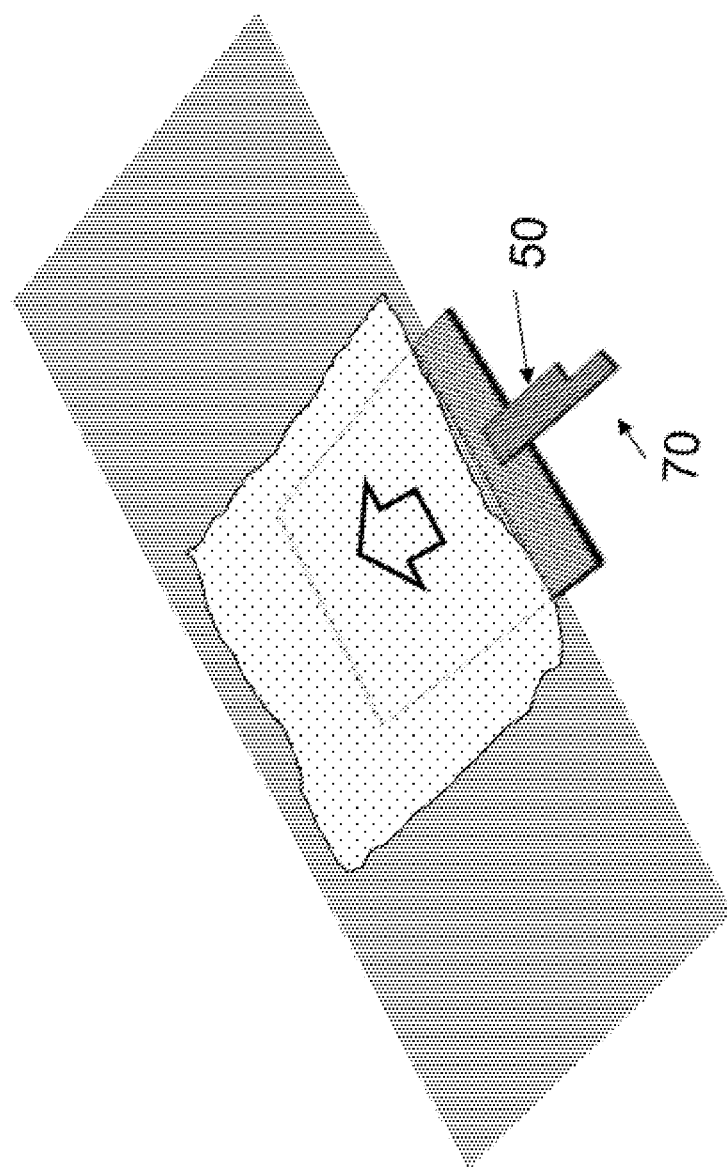
FIG. 18 shows an electrotechnical core which has been inserted into a tab in a bandage already present.

FIG. 18 shows an electrotechnical core 50, which is, e.g., inserted or else sewn into an already present tab of a bandage or a textile. The tab is preferably embodied in such a way that the electrotechnical core 50 completely disappears within the tab in the case of a completely inserted or sewn-in state.

Figure 19:
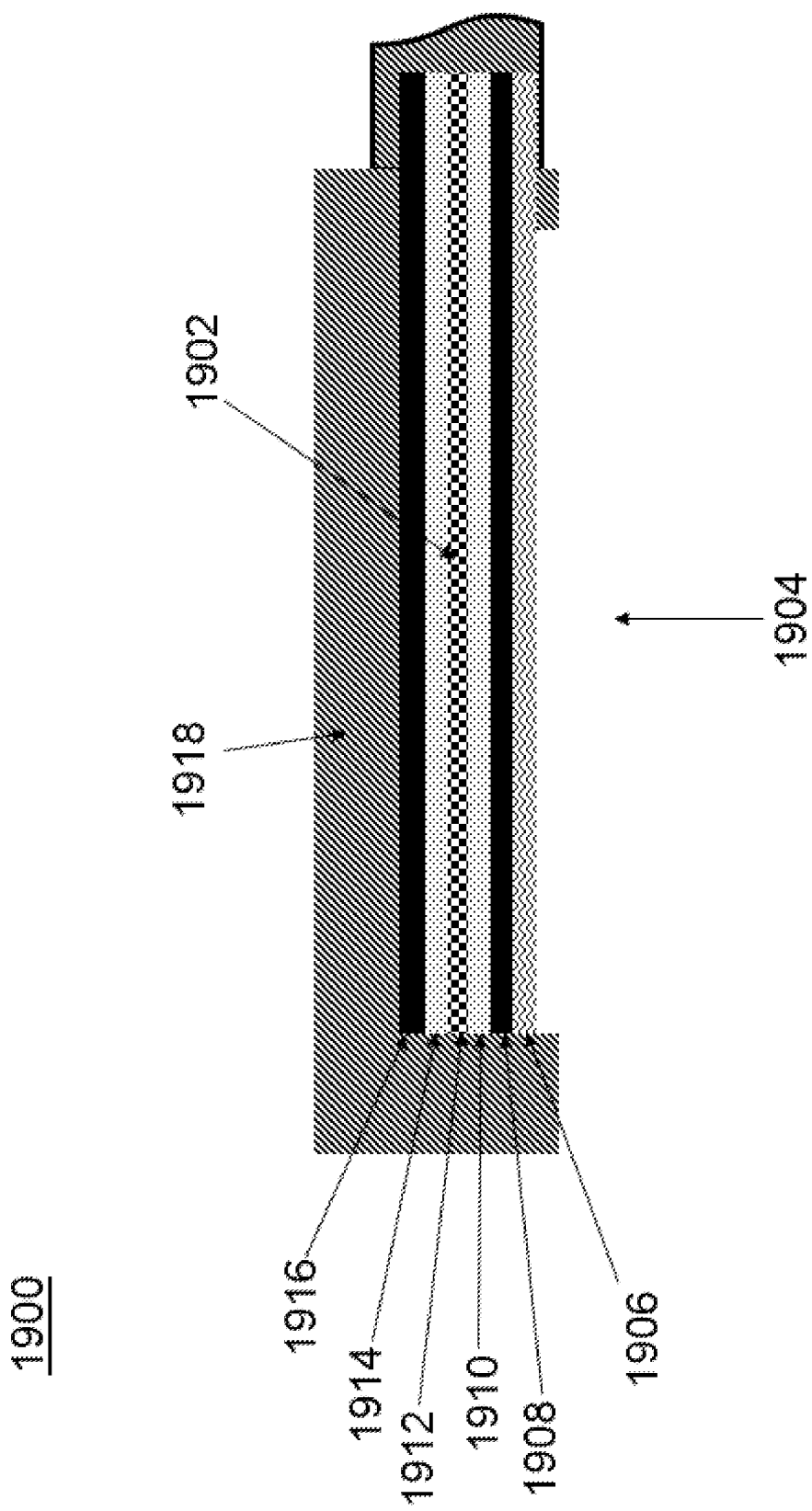
FIG. 19 shows a cross section through a plasma applicator with an electrotechnical core with, in each case, three electrode structures and three insulation layers.

FIG. 19 shows a cross section through a particularly preferred plasma applicator 1900 with an electrotechnical core 1902. The electrotechnical core 1902 comprises six flat, layer-like structures, which have a planar embodiment and are arranged in a layer stack as layers on top of one another. A first insulation layer 1906 with a planar embodiment, made of a biocompatible material, is situated on the side 1904 of the electrotechnical core 1902 that faces the human or animal or technical surface during use. The first insulation layer 1906 can be in direct contact with the human or animal or technical surface when the plasma applicator 1900 is applied to the corresponding surface. In different variants, the first insulation layer comprises an electrically insulating film and/or an electrically insulating lacquer and/or an electrically insulating adhesive layer and/or silicone.

In the direction of the side facing away from the surface to be treated, the first insulation layer 1906 is followed by a first electrode structure 1908, which has the function of a ground electrode. In the embodiment shown, the first electrode structure 1908 has specific geometry, which is meandering, spiral-shaped, formed by an area with holes, square, U-shaped, E-shaped, M-shaped, L-shaped, C-shaped, X-shaped or O-shaped in different variants of the embodiment shown. The first electrode structure 1908 is preferably produced using the screen printing method and has a thickness between 5 μm and 200 μm. In an embodiment not shown here, the first electrode structure 1908 is embodied as a planar electrode with a closed surface.

The first electrode structure in the form of a ground electrode 1908 is followed by a second insulation layer 1910, which is formed over the whole area, i.e., as a closed area. In different variants, the second insulation layer 1910 comprises, e.g., an electrically insulating film and/or an electrically insulating lacquer and/or an electrically insulating adhesive layer and/or silicone and has a thickness between 50 μm and 200 μm, preferably between 75 μm and 100 μm.

Arranged on the second insulation layer 1910 is a second electrode structure 1912, which is driven by a voltage signal for the purposes of generating a plasma during use. This second electrode structure 1912, driven during use by a voltage signal, likewise has a specific geometry. Optionally, the second electrode structure can also be embodied as a planar electrode. The second electrode structure 1912, driven during use, is preferably produced using the screen printing method and has a thickness between 5 μm and 200 μm, preferably between 5 μm and 100 μm, preferably between 5 μm and 20 μm.

The second insulation layer 1910 arranged between the first electrode structure 1908 at ground potential and the second electrode structure 1912 driven during application brings about a galvanic isolation of the two electrode structures.

The second electrode structure 1912, driven during use by a voltage signal, is followed by a third insulation layer 1914, which preferably comprises an electrically insulating film and/or an electrically insulating adhesive layer.

Arranged on the third insulation layer 1914 is a third electrode structure 1916. This third electrode structure 1916, which is embodied as a planar electrode, preferably as an electrically conductive film, is at reference potential during application. The third electrode structure 1916 has a thickness, preferably between 20 μm and 200 μm, preferably between 20 μm and 100 μm. During use, the third electrode structure 1916 fulfills the function of contact protection and EMC shielding. That is to say, during operation, the third electrode structure 1916 guarantees a lack of field between the driven, second electrode structure 1912 and a reference potential applied directly to the outer side of the electrotechnical core.

The third insulation layer 1914 arranged between the second electrode structure 1912, driven during use, and the third electrode structure 1916 has a whole-area embodiment and brings about a whole-area electrical insulation or galvanic isolation of the third electrode structure 1916 from the second electrode structure 1912.

Thus, a second ground electrode 1916 is provided in addition to a first ground electrode 1908 in the electrotechnical core 1902 shown, said second ground electrode being galvanically isolated from the second electrode structure 1912, driven during application, by a third insulation layer 1914. As a result, contact protection during operation is already realized by the electrotechnical core 1902 itself. The third electrode structure 1916 prevents electrical breakdown during operation between the driven, second electrode structure 1912 and a reference potential outside of the electrotechnical core or a virtual reference potential in the form of the surface to be treated or a human or animal. Advantageously, this allows a comparatively simple structure of an enclosure 1918 since an enclosure 1918 no longer necessarily needs to fulfill the function of contact protection. In particular, a complicated enclosure made of a first and second and third injection molded layer can be dispensed with in the electrotechnical core described here. In the case of conventional electrotechnical cores without a third insulation layer and a third electrode structure, an enclosure made of a first and second and third injection molded layer is typically necessary since, starting from the side facing away from the patient, the first injection molded layer consists of biocompatible silicone, the second injection molded layer consists of conductive silicone, which is at ground potential during operation, and the third injection molded layer consists of biocompatible silicone. Thus, the enclosure should ensure compatibility in contact with a surface to be treated and, at the same time, contact protection. Such an enclosure is comparatively complex to manufacture.

In the electrotechnical core described here, the functions of the first and second injection molded layer as structures and layers are integrated in the form of thin films in the electrotechnical core itself. In particular, an electrotechnical core as described here can be over-molded by only one injection molded layer made of silicone.

Advantageously, such an electrotechnical core itself is safe to touch and EMC-safe. Particularly advantageously, such an electrotechnical core can be used as a module and can be integrated into any plasma applicator or enclosure. By way of example, an electrotechnical core as described here can be integrated in a pad, in a superabsorber, in shoe soles, in compression stockings, in apparel.

It is particularly advantageous that such an electrotechnical core can be produced with a thickness of 300 µm or less. Such an electrotechnical core has a comparatively low vertical integration and can be produced, for example, as a film laminate. Advantageously, an electrotechnical core as described here can be produced significantly more easily and more cost-effectively, but preferably still is comparatively flat and flexible, and very flexible in respect of use. Advantageously, an electrotechnical core as described here can be produced in the same manufacturing process with a plug-in apparatus in the form of a tab.

Accordingly, the electrotechnical core 1902 shown here has six layers, wherein, in the layer stack of the six layers, an insulation layer 1906, 1910, 1914 and an electrode structure 1908, 1912, 1916 alternate in each case. An electrotechnical core 1902 as shown in FIG. 19 can be produced with a comparatively low production outlay and with comparatively low production costs.

To produce the electrotechnical core 1902 shown, a third insulation layer 1914, formed by a film, is laminated onto the second electrode structure 1912 that is driven during operation by a voltage signal. The electrically insulating effect of the third insulation layer can be reinforced by an adhesive used for the lamination, in particular. Then, the third electrode structure 1916 is applied to the third insulation layer 1914. It is also conceivable for the third insulation layer to be formed by the adhesive for lamination purposes and not as a separate film. In this case, the third electrode structure can be laminated directly onto the second electrode structure, with the adhesive between the second and the third electrode structure representing the third insulation layer.

In the illustration shown, the thicknesses of the individual layers of the multilayer system are chosen in such a way that the overall thickness along the layer stack of the shown electrotechnical core 902 ranges between approximately 200 µm and 300 µm, within the usual error tolerances. Consequently, this guarantees that the electrotechnical core 1902 is able to be deformed comparatively well and can be adapted comparatively easily to different body and/or surface shapes.

In the exemplary embodiment shown, the described layers of the electrotechnical core 1902 are produced as a laminate. Thus, the electrotechnical core 1902 consists of a film laminate.

The shown embodiment comprises an enclosure 1918 made of a biocompatible material. By way of example, a suitable biocompatible material 1918 is medical-grade silicone, lacquer, gauze, textiles, absorbers or adhesives or a combination of the aforementioned materials.

Since the third electrode structure 1916, grounded during use, fulfills the function of contact protection and EMC compatibility, the enclosure 1918 of the embodiment shown can be realized by a simple silicone overmold, for example. Thus, the enclosure 1918 shown has a comparatively simple structure.

In the embodiment shown, the electrotechnical core 1902 is only partly enclosed by the enclosure 1918. In particular, no enclosure 1918 could be provided on the side 1904 of the electrotechnical core 1902 which faces the surface to be treated during a plasma treatment. The enclosure 1918 can be produced, for example, using an injection molding method, a dipping method or a painting method. In an embodiment not shown here, an electrotechnical core is completely enclosed by an enclosure, e.g., in the form of a textile or gauze or pads.

In an embodiment not shown here, an electrotechnical core and, in particular, the second electrode structure, which is driven during use, are electrically connected to a plug-in apparatus. Such a plug-in apparatus preferably is embodied in chip card form and as described in relation to FIG. 2. In variants, not shown here, of the embodiment shown here, a plug-in apparatus or an electrotechnical core has at least one feature which ensures single use of the plasma applicator. By way of example, such a feature can be realized by a taper of a conductor track of the plug-in apparatus, as shown in FIG. 6, or a taper of an electrode section of an electrode structure in the electrotechnical core or as latching elements as described in relation to FIG. 16.

In an embodiment, not shown here, a plasma applicator comprises an integrated power supply unit and a plug-in apparatus. As described in relation to FIG. 8B, the integrated power supply unit can be connected to and charged by a mobile or a stationary power supply via the plug-in apparatus.

In a further embodiment, not shown here, a plasma applicator comprises an integrated power supply unit with an energy store but no plug-in apparatus. As described in relation to FIG. 8C, the integrated power supply unit is electrically connected to the electrotechnical core to supply power to the latter for the purposes of igniting a physical plasma.

In a further embodiment, not shown here, a plasma applicator comprises an insertion slot which is embodied to receive a mobile power supply unit. As described in relation to FIG. 8D, the plasma applicator can have contacts which, in particular, connect the electrode structure of the electrotechnical core driven during use to the upper side of the plasma applicator. The contacts at the surface have exposed contact areas, by means of which it is possible to establish galvanic coupling with an energy store of a mobile power supply unit when a mobile power supply unit is inserted into the insertion slot of the plasma applicator.

In a further embodiment, not shown here, a plasma applicator comprises an integrated receiver coil arrangement and an insertion slot into which a mobile power supply unit with a transmitter coil arrangement can be inserted. As described in relation to FIG. 8E, the transmitter coil arrangement can be used to transfer electrical energy provided by an energy store integrated in the mobile power supply unit to the receiver coil arrangement of the plasma applicator by means of inductive coupling for the purposes of supplying power to the electrotechnical core and consequently for the purposes of igniting a physical plasma.

In a further embodiment not shown here, a plasma applicator comprises an integrated power supply unit with an accumulator or a capacitor, which can be charged by means of a charging apparatus that is likewise integrated. As described in relation to FIG. 8F, inductive coupling can be used to transmit electrical energy from a commercially available charging station to the charging apparatus in order to charge an energy store of the integrated power supply unit for the purposes of supplying power to the electrotechnical core.

FIGS. 20, 21, 22, and 23 each show selected intermediate products of a production method for producing an electrotechnical core as shown in FIG. 19.

Figure 20:
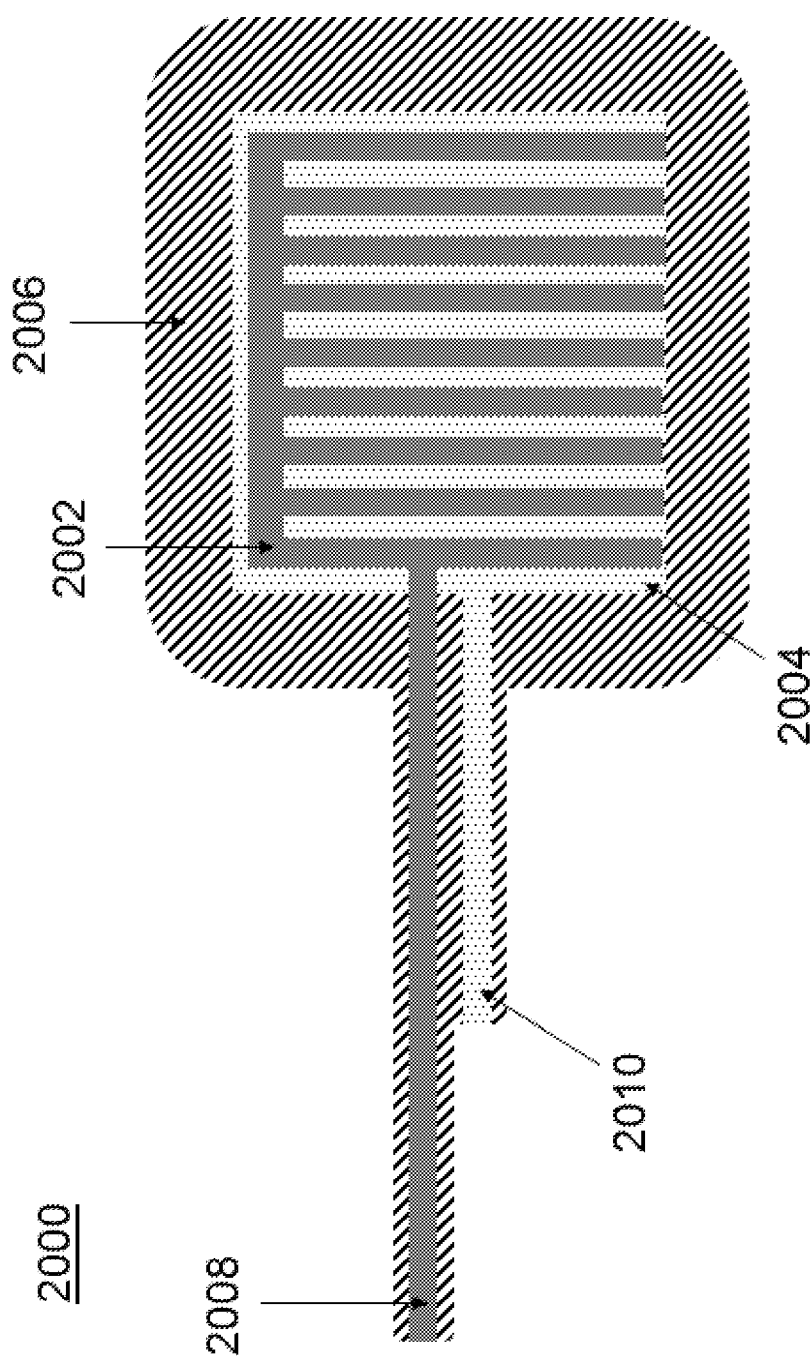
FIG. 20 shows a plan view of the side of an electrotechnical core which faces away from the surface to be treated during a plasma treatment.

FIG. 20 shows a plan view of that side of an electrotechnical core 2000 which faces away from the surface to be treated during a plasma treatment. The electrotechnical court 2000 comprises a second electrode structure 2002 that is driven during operation by a voltage signal. The second electrode structure 2002, driven during use, has a specific geometry with a comb-shaped embodiment. In the direction of the side facing the side to be treated, the second electrode structure 2002, driven during use, is followed by a second insulation layer 2006 and this second insulation layer is followed by a grounded, first electrode structure 2004, which represents that ground electrode that faces the surface to be treated during use. Both the second electrode structure 2002, driven during use, and the first electrode structure 2004 comprise a respective conductor track 2008, 2010, which, from a longitudinal side of the electrotechnical core 2000, leads away from the corresponding electrode structures 2002, 2004 in perpendicular fashion in the same horizontal plane. These conductor tracks 2008, 2010 form the conductor tracks of a plug-in apparatus. Corresponding conductor tracks of the plug-in apparatus are then electrically conductively connected to the electrotechnical core 2000. Optionally, the plug-in apparatus can comprise a reinforcement.

In the direction of the surface side to be treated, the shown first electrode structure 2004 is followed by a first insulation layer (not shown), which can come into direct contact with a surface to be treated during use. The first insulation layer (not shown) is embodied in such a way that it also electrically insulates the conductor tracks 2008, 2010 in the direction of a surface to be treated.

Figure 21:
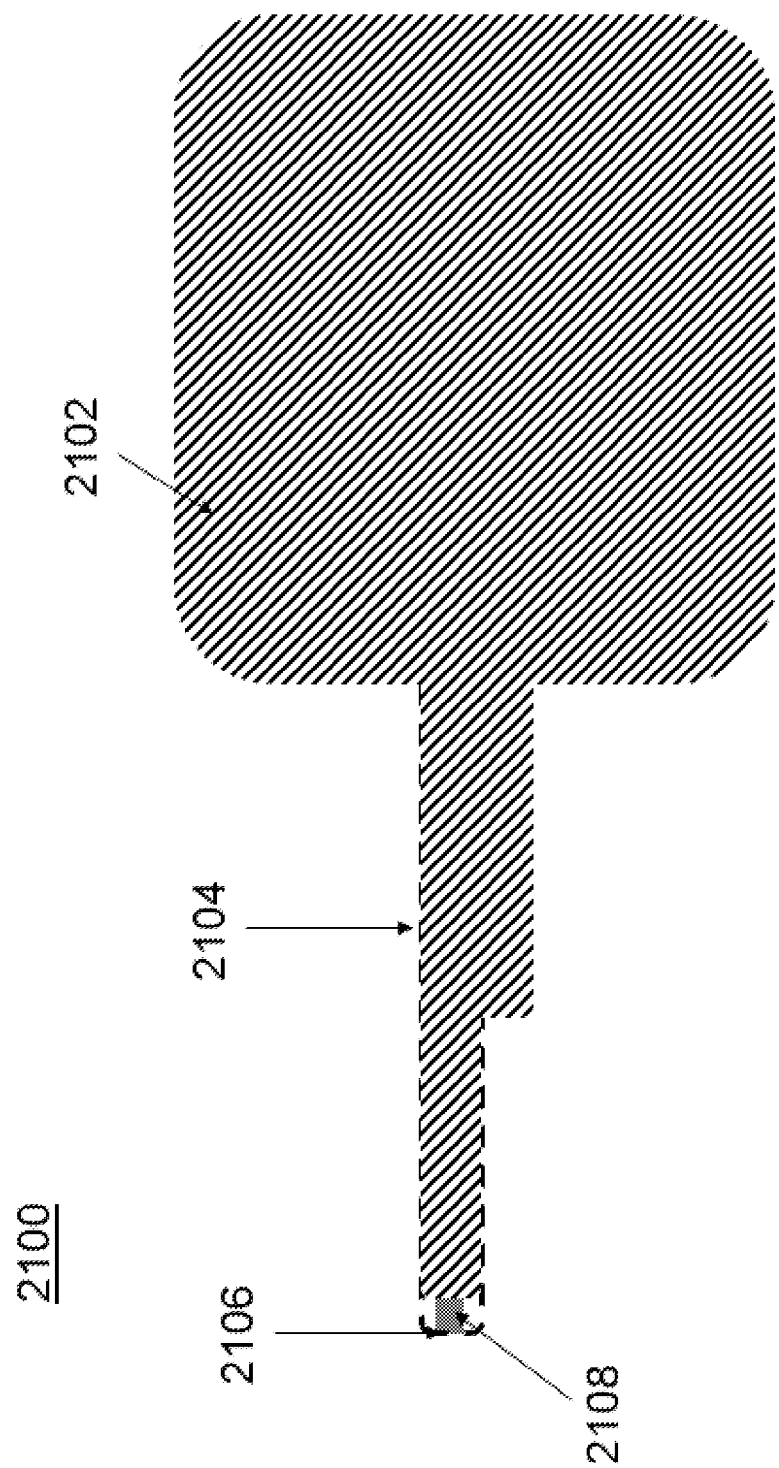
FIG. 21 shows a plan view of the side of an electrotechnical core which faces away from the surface to be treated during a plasma treatment, wherein the third insulation layer, in particular, can be seen.

FIG. 21 shows a plan view of that side of an electrotechnical core 2100 which faces away from the surface to be treated during a plasma treatment. Essentially, the third insulation 2102 of the shown electrotechnical core 2100 is visible, said insulation layer being arranged on the side facing away from the surface to be treated during a plasma treatment and on the second electrode structure (not shown) that is driven during operation. This third insulation layer 2102 fulfills the function of galvanically isolating the second electrode structure, which is driven during operation, and a third electrode structure (not shown), which is arranged on the third insulation layer, from one another. The shown third insulation layer 2102 has a whole-area embodiment and has a tab 2104, which covers both conductor tracks, at the point where the conductor tracks from the second electrode structure, which is driven during use, and from the first electrode structure, arranged on the side of the electrotechnical core 2100 facing the surface to be treated, are led away. However, the tab 2104 does not end flush with the end of 2106 of the conductor track of the electrode structure driven during operation, but ends therebefore. As a result, the contact face 2108 of the conductor track remains exposed, which represents a contacting face for transmitting a voltage signal between the plug-in apparatus and the contacts of the insertion apparatus.

Figure 22:
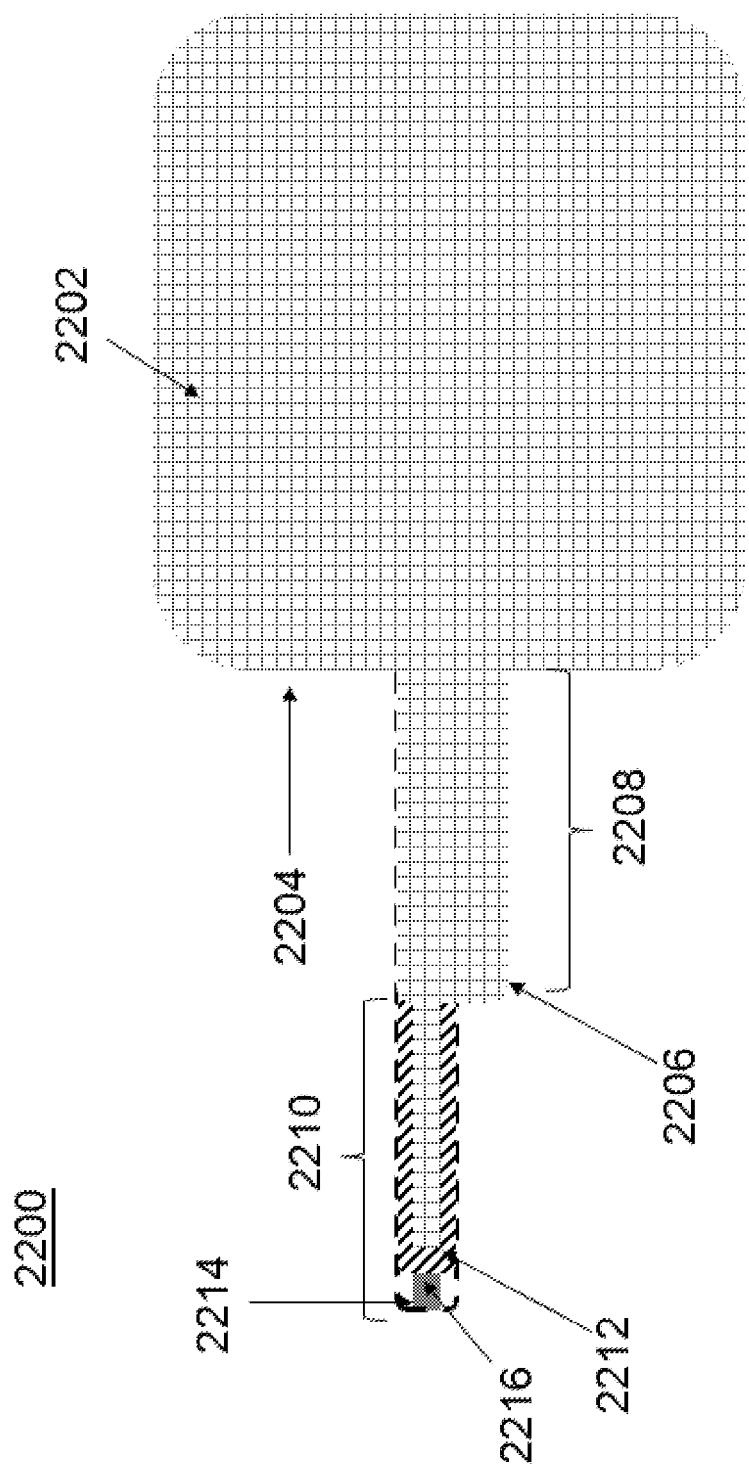
FIG. 22 shows a plan view of the side of an electrotechnical core which faces away from the surface to be treated during a plasma treatment, wherein the third electrode structure, in particular, can be seen.

FIG. 22 shows a plan view of that side of an electrotechnical core 2200 which faces away from the surface to be treated during a plasma treatment. Essentially, the third electrode structure 2202 of the shown electrotechnical core 2200 is visible, said third electrode structure being arranged on the side facing away from the side to be treated and being galvanically isolated by a third insulation layer (reference sign 2102 in FIG. 21) from a second electrode structure, which is driven during use. This third electrode structure 2002 fulfills the function of contact protection and EMC protection such that there is no electrical breakdown between a driven electrode structure of the electrotechnical core 2200 and a reference potential directly applied to the outer side or a virtual reference potential during use, for example as a result of contact with a patient or user. The shown third electrode structure 2202 is preferably embodied as a planar electrode; i.e., it has no specific geometry. On the side 2204 of the electrotechnical core 2200 at which the conductor tracks lead away from the second electrode structure, which is driven during use, and from the first electrode structure, arranged on the side of the electrotechnical core 2200 facing the surface to be treated, the shown third electrode structure 2202 also comprises a tab-shaped conductor track 2206. The tab-shaped conductor track 2206 completely covers the region 2208, in which both the conductor track of the second electrode structure, which is driven during operation, and the conductor track of the first electrode structure (not shown) are situated.

In the region 2210, which goes beyond the region 2208 with both conductor tracks and only still comprises the conductor track of the second electrode structure, which is driven during operation, the tab-shaped conductor track 2206 of the shown third electrode structure 2202 has a sufficient width so that shielding of the second electrode structure is ensured, contact protection is provided and, at the same time, a plasma discharge igniting between the third electrode structure and the second electrode structure is precluded. The third insulation layer 2212 arranged therebetween has a greater width than the conductor track of the second electrode structure, which is driven during operation, in order to ensure galvanic isolation of the two electrode structures. The tab-shaped conductor track 2206 of the shown third electrode structure 2202 already ends before the end 2214 of the tab of the shown third insulation layer 2212 such that, furthermore, a contact face 2216 of the conductor track of the second electrode structure, which is driven during operation, remains exposed in order to establish electrical contact between the formed plug-in apparatus and the contacts of the insertion apparatus for the purposes of transmitting a voltage signal.

Figure 23:
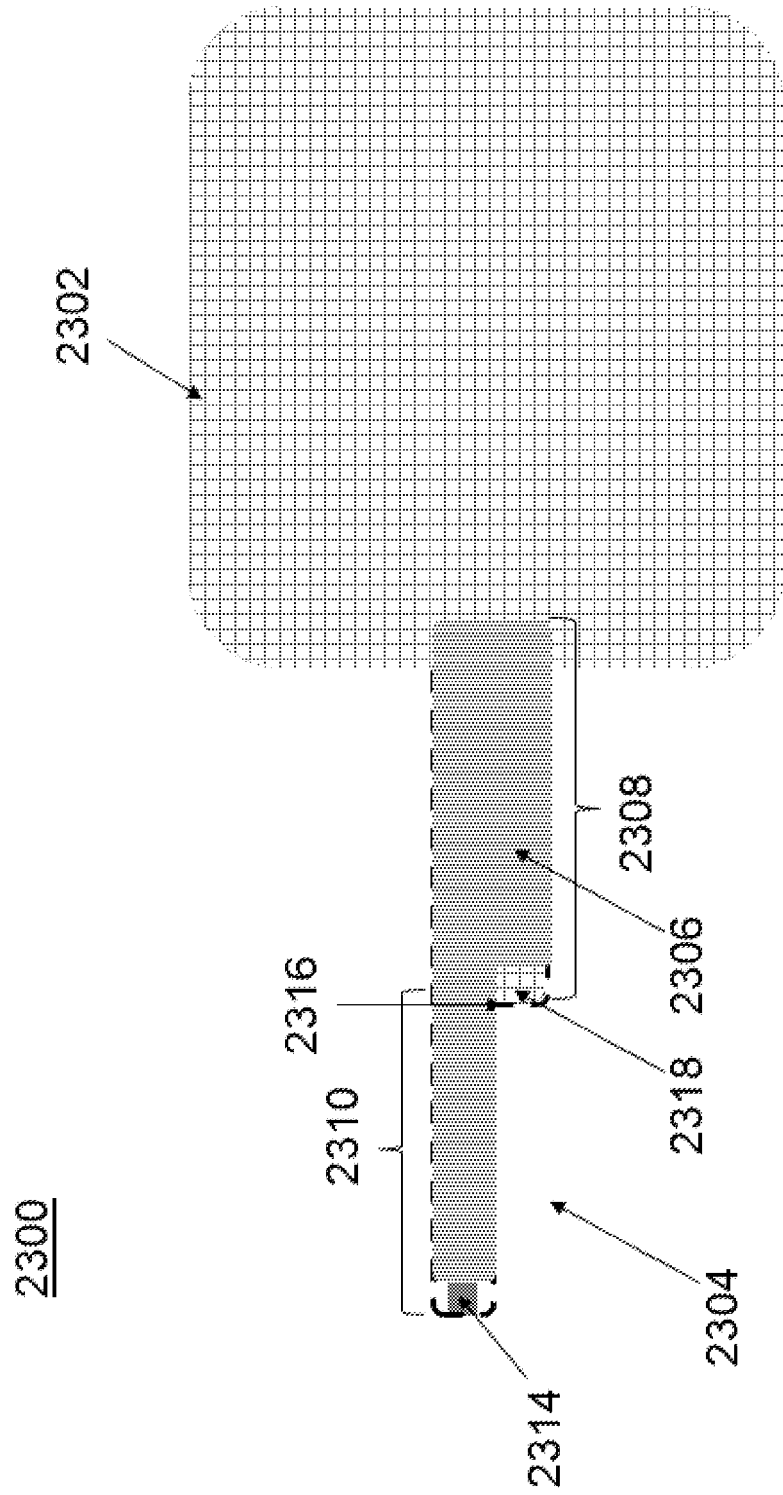
FIG. 23 shows a plan view of the side of an electrotechnical core which faces away from the surface to be treated during a plasma treatment, wherein the electrotechnical core comprises a third electrode structure and a reinforcement.

FIG. 23 shows a plan view of that side of an electrotechnical core 2300 which faces away from the surface to be treated during a plasma treatment. Essentially, the third electrode structure 2302 with a tab-shaped conductor track 2304, as described with respect to FIG. 22, of the electrotechnical core 2300 shown is visible. In addition to the electrotechnical core 2200 shown in FIG. 22, the electrotechnical core 2300 shown here comprises a chip card-shaped reinforcement 2306, which encloses the tab-shaped conductor track of the electrode structures and isolation layers described in relation to FIGS. 20, 21, and 22 and tab-shaped conductor tracks of the electrode structures, not described but additionally present in the electrotechnical core 2300 and tabs of the insulation layers. In particular, the chip card-shaped reinforcement 2306 has the same basic shape as the tab-shaped conductor tracks, enclosed thereby or arranged at one side, and tabs; i.e., in the region 2308 containing both the conductor structure of the second electrode structure, which is driven during operation, and the conductor track of the third electrode structure at ground potential, the chip card-shaped structure 2306 also has a greater width than in the region 2310, in which there only is the conductor track of the second electrode structure, which is driven during operation. In the region 2310 containing only the conductor track of the second electrode structure, which is driven during operation, the chip card-shaped reinforcement 2306 ends flush with the end of the insulation layer shown in FIG. 21 so that the contact face 2314 of the conductor track of the second electrode structure, which is driven during operation, continues to remain exposed.

In the region 2308, containing both the conductor track of the second electrode structure, which is driven during operation, and the conductor track of the third electrode structure, the chip card-shaped structure 2306 is embodied in such a way that it terminates before the end 2316 of the tab-shaped conductor track 2304 of the third electrode structure 2306 on the side on which the conductor track of the third electrode structure 2302 is situated, and so a contact face 2318 of the conductor track, in the form of a tab-shaped conductor track 2316 of the third electrode structure 2302, also remains exposed in this case.

Figure 24:
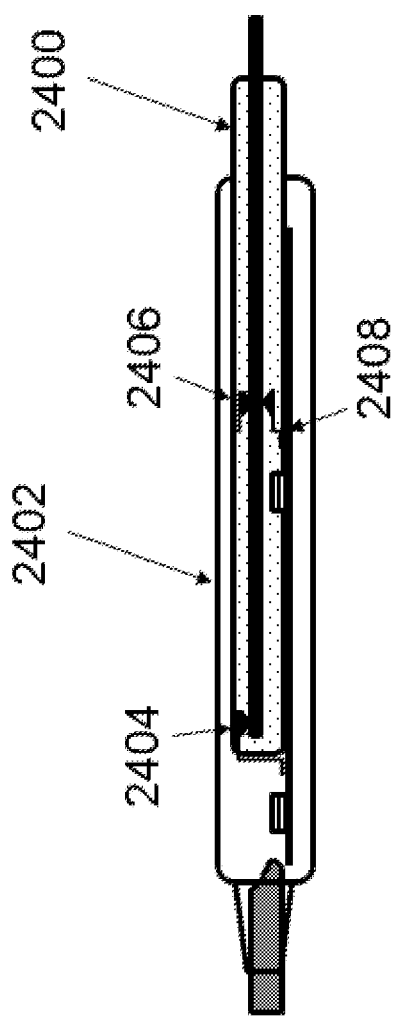
FIG. 24 shows a plug-in apparatus which is brought together with an insertion apparatus.

FIG. 24 shows a plug-in apparatus 2400, which is plugged together with an insertion apparatus 2402 with a complementary embodiment. The plug-in apparatus 2400 comprises three conductor tracks, wherein one conductor track is the conductor track of a first electrode structure, a second conductor track is the conductor track of a second electrode structure, which is driven during operation, and a third contractor track is the conductor track of a third electrode structure, wherein the third electrode structure during operation fulfills the function of contact protection for a reference potential at the side facing away from the side to be treated and represents EMC protection.

Since three conductor tracks are present in the plug-in apparatus 2400 shown, the insertion apparatus 2402 embodied as a coupling comprises a connector 2404 for transmitting a voltage signal to the second electrode structure, which is driven during operation, and two further connectors 2406, 2408 for contacting the two conductor tracks of the first and third electrode structure, which are preferably at ground potential. Thus, in comparison with the insertion apparatus shown in FIG. 2, an additional connector 2406 is provided for contacting the second ground electrode.

Figure 25:
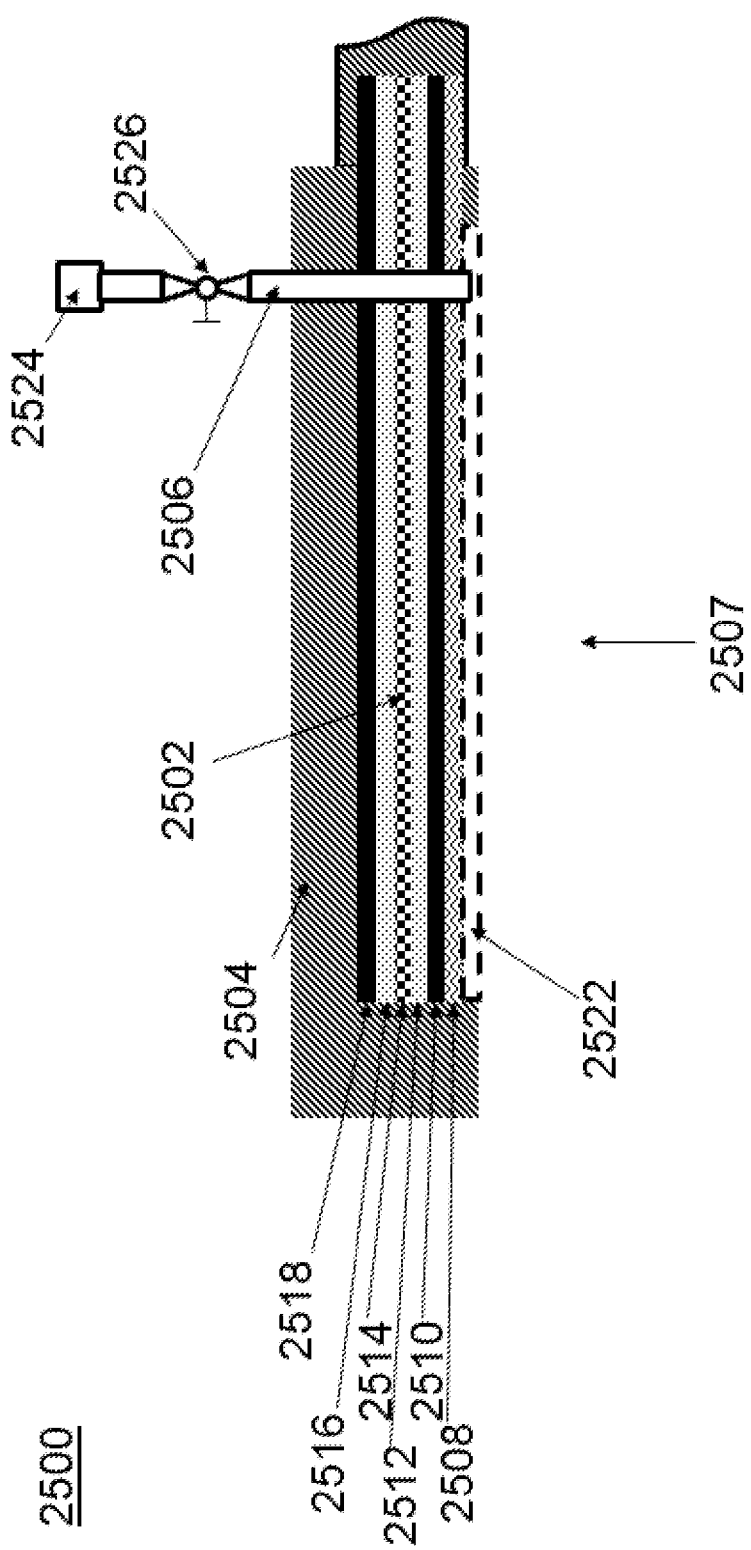
FIG. 25 shows a plasma applicator with an electrotechnical core, an enclosure, and an access port.

FIG. 25 shows a plasma applicator 2500 with an electrotechnical core 2502, an enclosure 2504, and an access port 2506. The electrotechnical core 2502 is embodied as described with respect to FIG. 19 and comprises, in the layer thickness direction starting from the side 2507 facing a surface to be treated, a first insulation layer 2508, a first electrode structure 2510, a second insulation layer 2512, a second electrode structure 2514, a third insulation layer 2516, and a third electrode structure 2518. During operation, the first and the third electrode structure 2510, 2518 are grounded. Thus, the electrotechnical core 2502 shown here already has an embodiment safe to touch per se. A voltage signal sufficient to ignite a plasma is applied to the second electrode structure 2514 during operation. In embodiments not shown here, the plasma applicator has a differently embodied electrotechnical core in each case, which, for example, merely comprises a second electrode structure and a second insulation layer in one embodiment.

In the embodiment shown, the access port 2506 is embodied as a tubular spout and guided in perpendicular fashion with respect to a surface to be treated through the enclosure 2504 and the electrotechnical core 2502. To this end, the electrotechnical core 2502 and the enclosure 2504 each have a passage, which has a diameter that corresponds to the external diameter of the tubular spout. The spout 2506 is hollow in the interior such that a fluid medium can be guided through the spout. During use, an end of the spout 2506 is situated in a sealed gas space 2522 that is formed between the plasma applicator 2500 and a surface to be treated. The other end of the spout 2506 is situated outside of the plasma applicator 2500 on the side facing away from a surface to be treated such that, when a plasma applicator is arranged on a surface to be treated, a medium or else a plurality of fluid media can be added to the sealed gas space 2522 or can be removed from the sealed gas space 2522 through the tubular spout 2506.

In the embodiment shown, the sprout 2506 has a female socket 2524 for fastening a tube (not shown) with a complementary thread to the tubular spout 2506. By way of a tube (not shown) connected to the female socket 2524, a fluid medium can be added to and/or removed from the sealed gas space 2522. By way of example, a tube (not shown) can be connected to a vacuum pump (not shown) and the vacuum pump can generate negative pressure in the sealed gas space 2522.

In the embodiment shown, the tubular spout 2506 comprises an integrated valve 2526, which allows a flow of a fluid medium through the tubular spout 2506 to be controlled and stopped. Such a valve 2526 can be manually controllable, machine-controllable or electronically controllable.

In an embodiment not shown here, a plasma applicator comprises an enclosure and an access port, as described with respect to FIG. 25, and an electrotechnical core, as described with respect to FIG. 7. In a further embodiment, not shown here, a plasma applicator comprises an enclosure and an access port, as described with respect to FIG. 25, and an electrotechnical core with only one electrode structure, a voltage signal being applied thereto during operation. In this embodiment, a surface to be treated fulfills the function of a counter electrode during operation.

Figure 26:
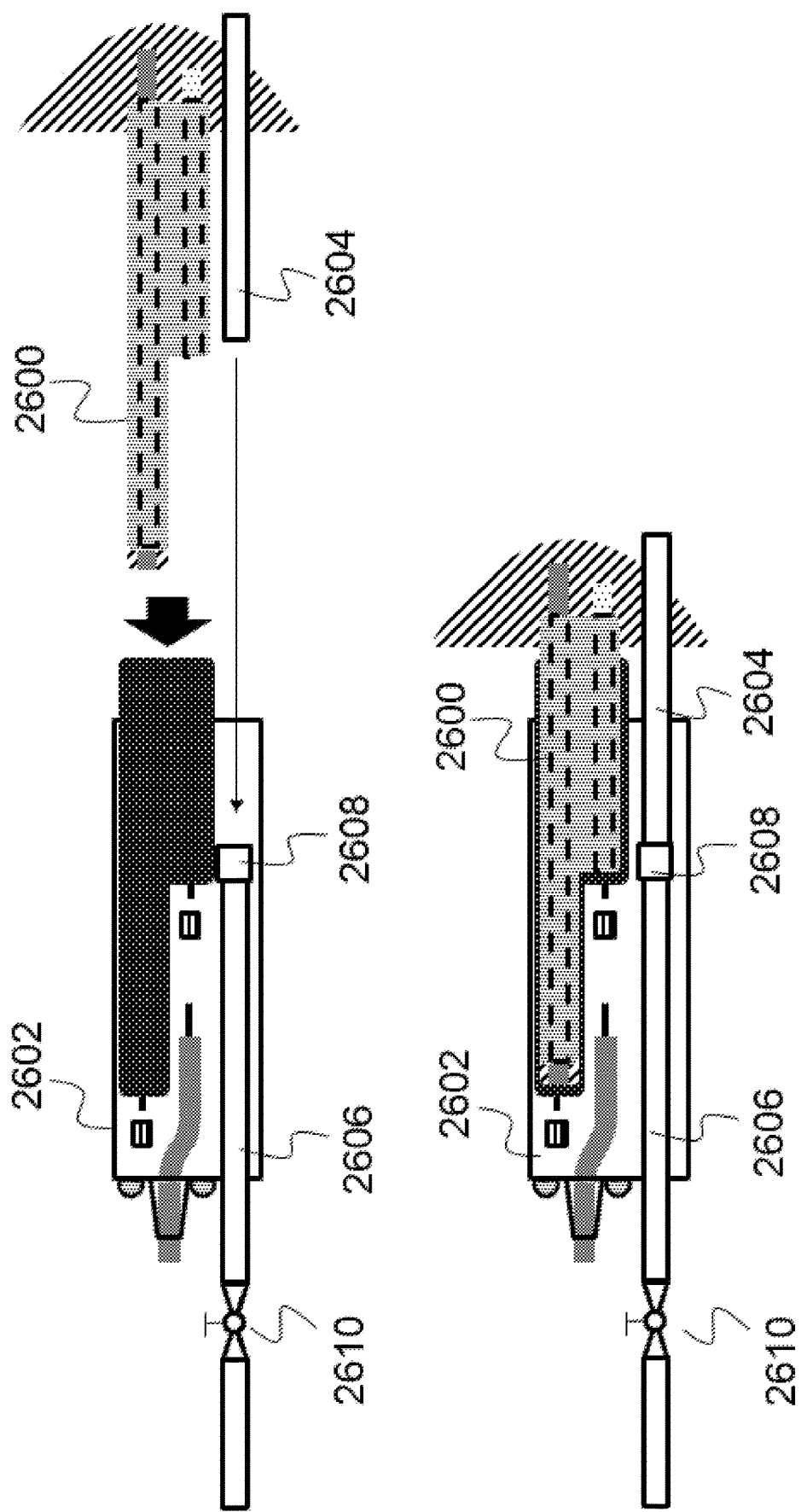
FIG. 26 shows a plug-in apparatus with an access port and an insertion apparatus with an embodiment complementary to that of the plug-in apparatus.

FIG. 26 shows a plug-in apparatus 2600 and an insertion apparatus 2602 with a complementary embodiment to the plug-in apparatus 2600. The plug-in apparatus 2600 is arranged at an electrotechnical core of a plasma applicator, which is merely indicated in the illustration shown. The plug-in apparatus 2600 is embodied as described with respect to FIGS. 2A and 2B, although it additionally comprises an access port 2604. In the illustration shown, the access port 2604 is guided at a distance next to the tabs of the plug-in apparatus 2600 but forms a component of the plug-in apparatus.

The insertion apparatus 2602 is likewise embodied as described with respect to FIGS. 2A and 2B, although it additionally comprises a tube 2606 with a socket 2608 and a valve 2610. In an embodiment not shown here, a plug-in apparatus embodied as described with respect to FIG. 24 comprises an access port and an insertion apparatus embodied as described with respect to FIG. 24 comprises a tube with a socket and a valve.

Thus, in the embodiment shown, an access port 2604 in the form of a spout is part of the plug-in apparatus 2600. The counterpart to the spout 2604 is situated in the complementary insertion apparatus 2602. Thus, the spout 2604 can be connected to the tube 2602 via the socket 2608 such that a fluid medium can be guided via the tube 2602 in the insertion apparatus 2602 to the spout 2604 of the plug-in apparatus 2600. In the brought-together state of plug-in apparatus 2600 and insertion apparatus 2602, illustrated at the bottom, the plug-in apparatus 2600 and the insertion apparatus 2602 have a water-tight and air-tight connection.

Figure 27:
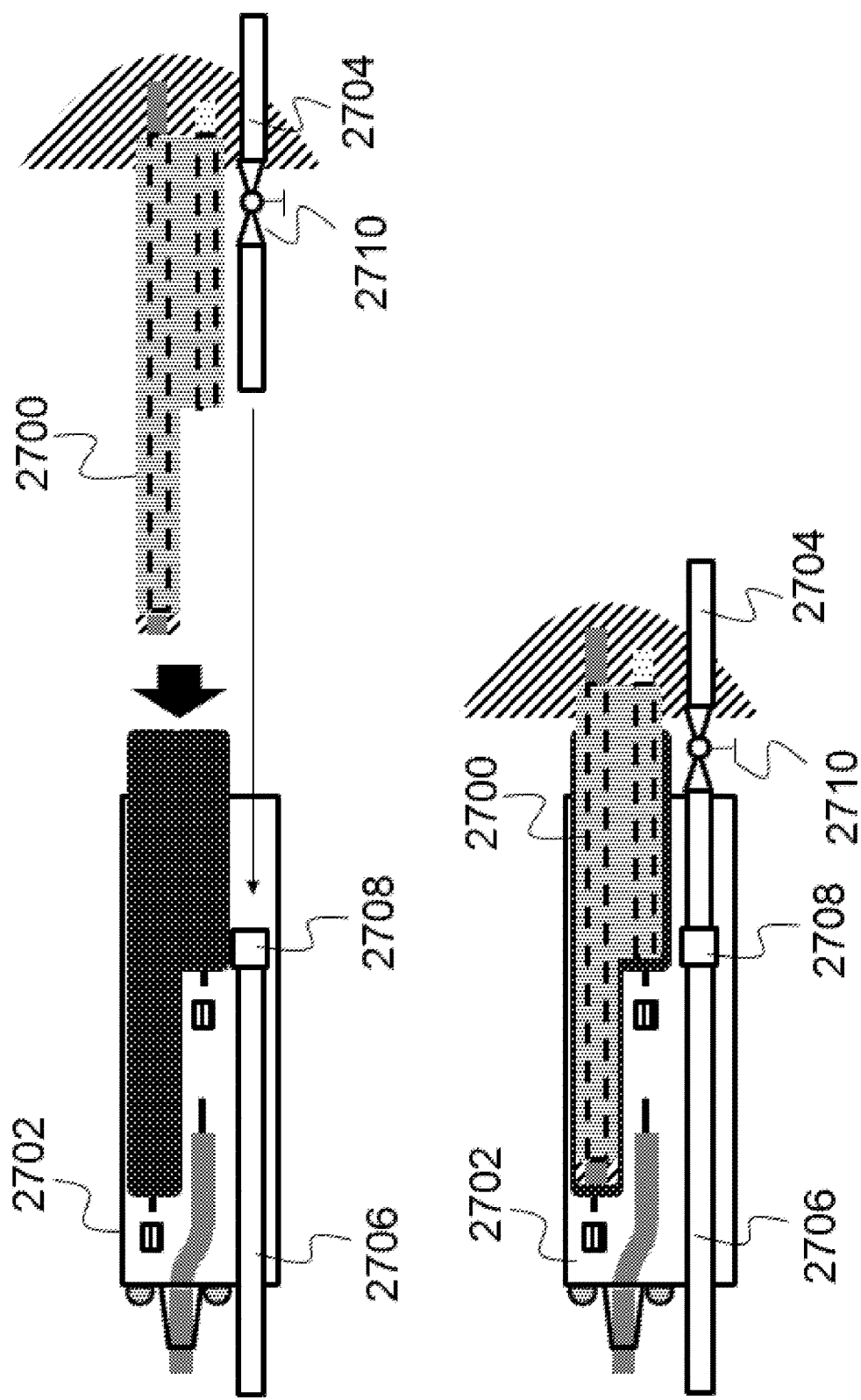
FIG. 27 shows a plug-in apparatus with an access port and an insertion apparatus with an embodiment complementary to that of the plug-in apparatus.

FIG. 27 shows a plug-in apparatus 2700 and an insertion apparatus 2702 with a complementary embodiment to the plug-in apparatus 2700. The plug-in apparatus 2700 is arranged at an electrotechnical core of a plasma applicator, which is merely indicated in the illustration shown. The plug-in apparatus 2700 is embodied as described with respect to FIGS. 2A and 2B, although it additionally comprises an access port 2704 with a valve 2710. In the illustration shown, the access port 2704 is guided at a distance next to the tabs of the plug-in apparatus 2700 but forms a component of the plug-in apparatus 2700.

The insertion apparatus 2702 is likewise embodied as described with respect to FIGS. 2A and 2B, although it additionally comprises a tube 2706 with a socket 2708. In an embodiment not shown here, a plug-in apparatus embodied as described with respect to FIG. 24 comprises an access port with a valve and an insertion apparatus embodied as described with respect to FIG. 24 comprises a tube with a socket.

Thus, in the embodiment shown, an access port 2704 in the form of a spout is part of the plug-in apparatus 2700. The counterpart to the spout 2704 is situated in the complementary insertion apparatus 2702. Thus, the spout 2704 can be connected to the tube 2706 via the socket 2708 attached to a corresponding end of the tube such that a fluid medium can be guided via the tube 2706 in the insertion apparatus 2702 to the spout 2704 of the plug-in apparatus 2700. In the brought-together state of plug-in apparatus 2700 and insertion apparatus 2702, shown at the bottom, the plug-in apparatus 2700 and the insertion apparatus 2702 have a water-tight and air-tight connection. The through-flow of a fluid medium can be controlled or stopped by setting the valve of the access port 2704.

Figure 28:
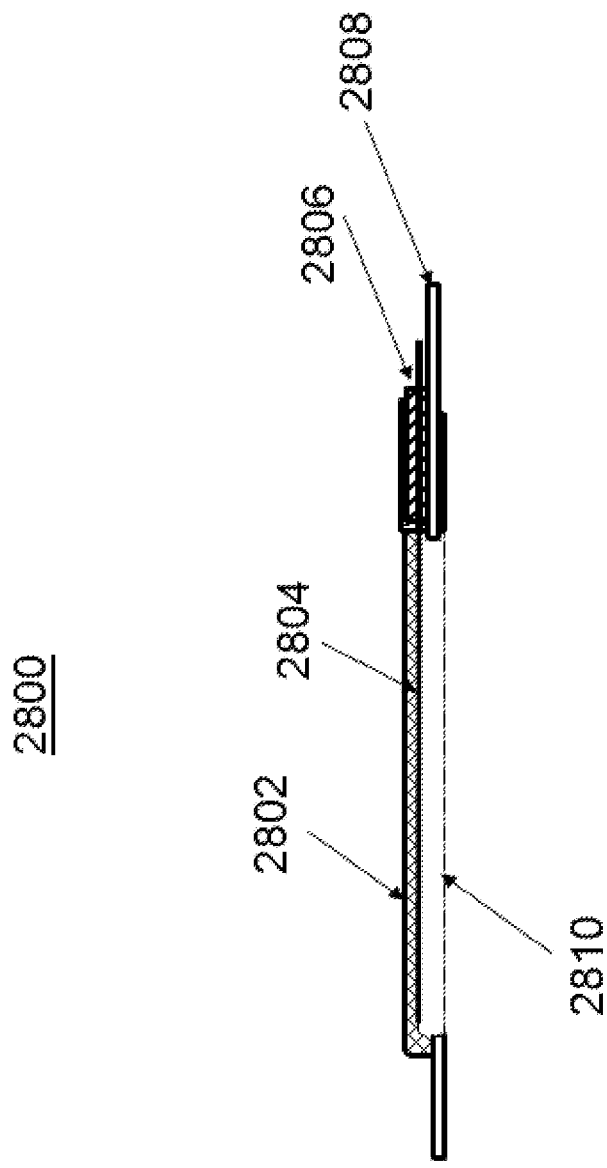
FIG. 28 shows a plasma applicator comprising an enclosure, an electrotechnical core, and a plug-in apparatus with an access port.

FIG. 28 shows a plasma applicator 2800 which comprises an enclosure 2802, an electrotechnical core 2804, and a plug-in apparatus 2806 with an access port 2808. During use, a sealed gas space 2810 is formed between the plasma applicator 2800 and a surface to be treated. The access port 2808 ends in the gas space 2810 with the one end and the access port 2808 ends outside of the plasma applicator 2800 with the other end such that a fluid medium can be guided through the access port into the sealed gas space 2810 from outside of the plasma applicator or said fluid medium can be removed from the connected gas space 2810. In particular, the plug-in apparatus 2806 can be plugged together with a complementary insertion apparatus (not shown), the latter comprising a tube which can be connected to the access port, for example by way of a socket or by plugging together.

FIG. 29 shows a plasma applicator 2900 with a sensor system. The plasma applicator 2900 furthermore comprises an enclosure 2902 and an electrotechnical core 2904. The plasma applicator comprises an adhesion layer 2908 in at least one region along a perimeter of the plasma applicator 2900. During use, the enclosure 2902 establishes a sealed gas space 2910 between the plasma applicator 2900 and a body segment to be treated.

The sensor system comprises a first sensor 2912 and a second sensor 2914. The first sensor 2912 is attached to the plasma applicator at a distance from a body segment to be treated and is embodied to capture measurement variables that are characteristic for the gas space 2910 and transmit a data signal 2919 representing the captured measurement variable to a data processing device 2916. During use, the second sensor 2914 is attached to the plasma applicator in direct contact with a body segment to be treated and embodied, during use, to capture a physiological measurement variable of a body segment covered by the plasma applicator 2900 and to transmit a data signal 2920 representing the captured measurement variable to a data processing device 2916.

Figures 30A, 30B:
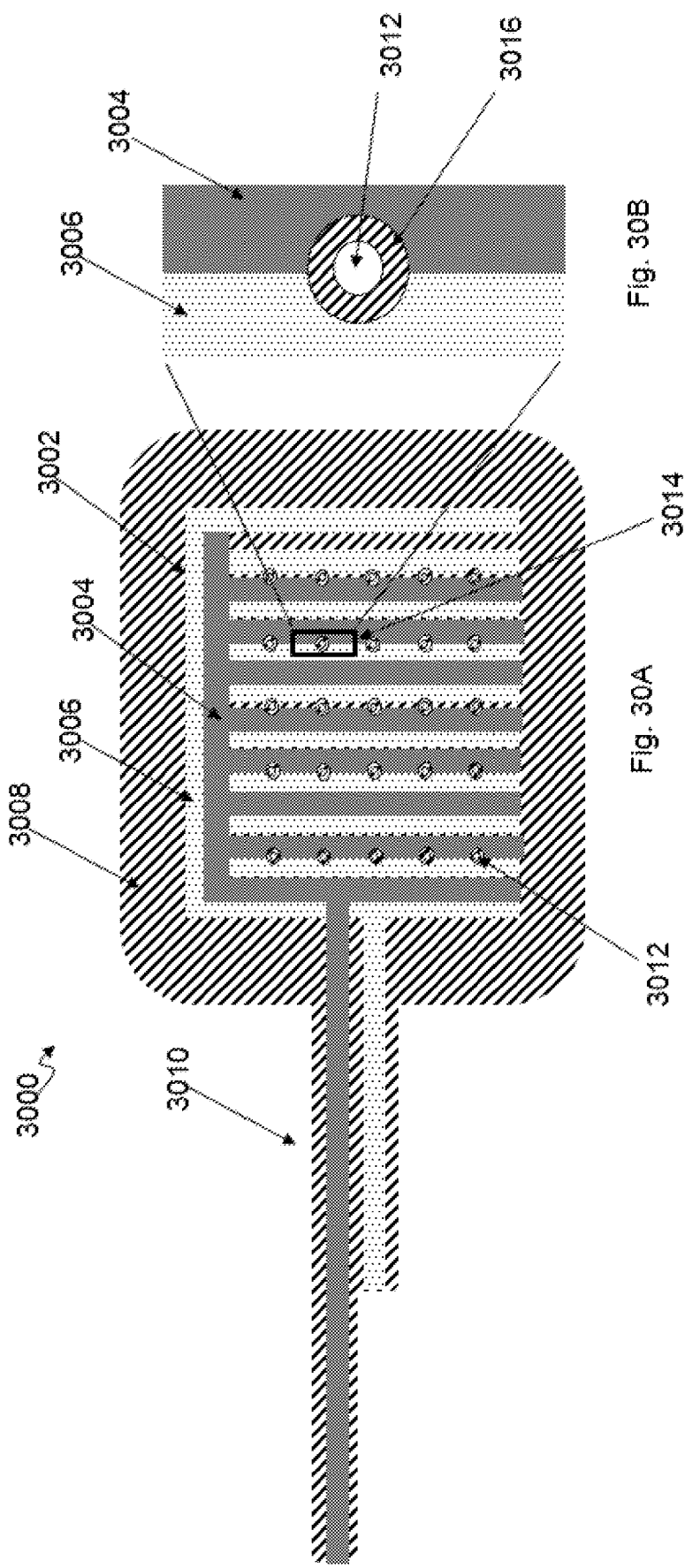
FIG. 30A shows a plasma applicator with an electrotechnical core, which has a number of passages distributed over its area.
FIG. 30B shows a portion, illustrated in magnified fashion, of the plasma applicator shown in FIG. 30A.

FIG. 30A shows a plasma applicator 3000 with an electrotechnical core 3002, which comprises a first electrode structure 3004 and a second electrode structure 3006. The plasma applicator furthermore comprises an enclosure 3008 and a plug-in apparatus 3010.

The electrotechnical core 3002 has holes or passages 3012, which are arranged distributed over the entire area of the electrotechnical core 3002. The holes or passages 3012 can facilitate a media transport through the electrotechnical core 3002, from the side facing a surface to be treated to the side of the plasma applicator 3000 facing away from a surface to be treated or, in the reverse direction, from the side facing away from a surface to be treated to the side of the plasma applicator 3000 facing a surface to be treated. The electrode structures 3004, 3006 have a distance from the respective holes 3012; i.e., they are not part of the surface of the electrotechnical core 3002 enclosing a passage 3012. The enclosure 3008 is formed by a media-transporting material.

FIG. 30B shows the portion of the plasma applicator 3000 framed by the box 3014 in a magnified illustration. A part of an electrode section of the first electrode structure 3004 and a part of an electrode section of the second electrode structure 3006 can be seen in this portion. Furthermore, one of the passages 3012 is visible. It is clear from this illustration that the electrode sections do not reach up to the passage but terminate at a distance therefrom. The surface surrounding the passage 3012 is only formed by insulation layers 3016 of the electrotechnical core 3002.

Figure 31:
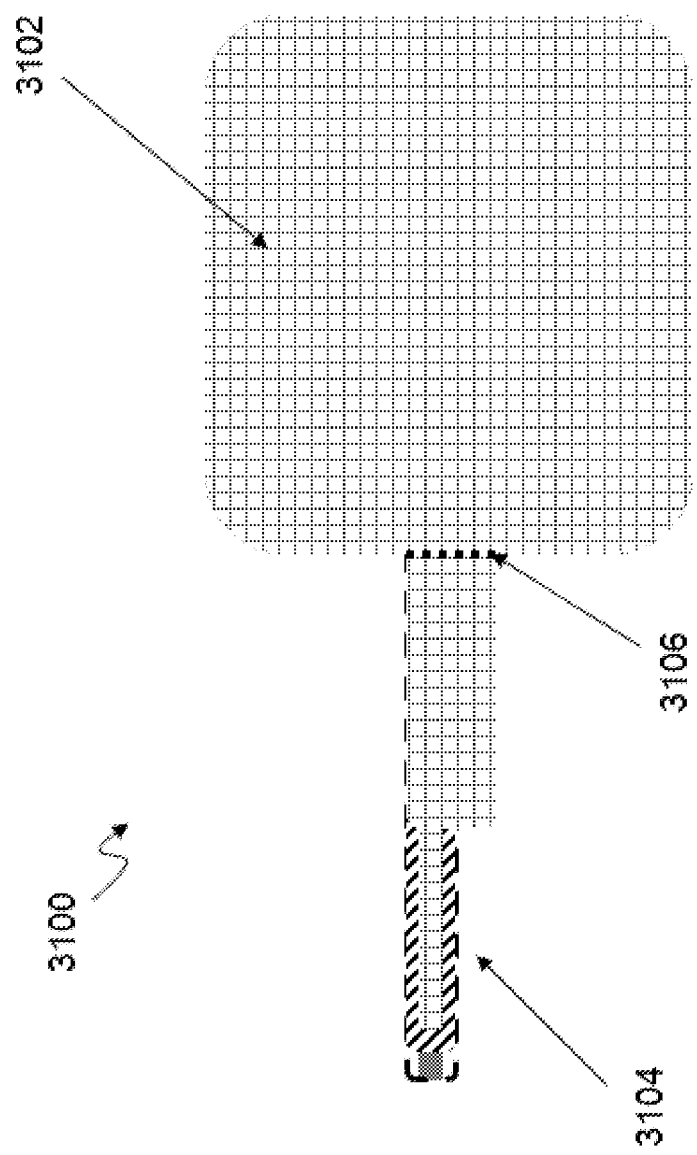
FIG. 31 shows a plasma applicator with an electrotechnical core and a plug-in apparatus, wherein a perforation is formed at the transition from electrotechnical core to plug-in apparatus.

FIG. 31 shows a plasma applicator 3100 with an electrotechnical core 3102 and a plug-in apparatus 3104. At the transition from electrotechnical core 3102 to plug-in apparatus 3104, the plasma applicator 3100 has a perforation 3106. The function of the perforation 3106 lies in the reduction of the strength between plug-in apparatus 3104 and electrotechnical core 3102. The perforation 3106 represents an intended breaking point. Following a plasma treatment, the plug-in apparatus 3104 can be torn off or removed from the electrotechnical core 3102 at this perforation 3106. As a result, a plasma applicator 3100 can remain on a surface to be treated for a relatively long period of time, from days to weeks, independently of a power supply unit since the plug-in apparatus 3104, no longer needed, is removed.

Figure 32:
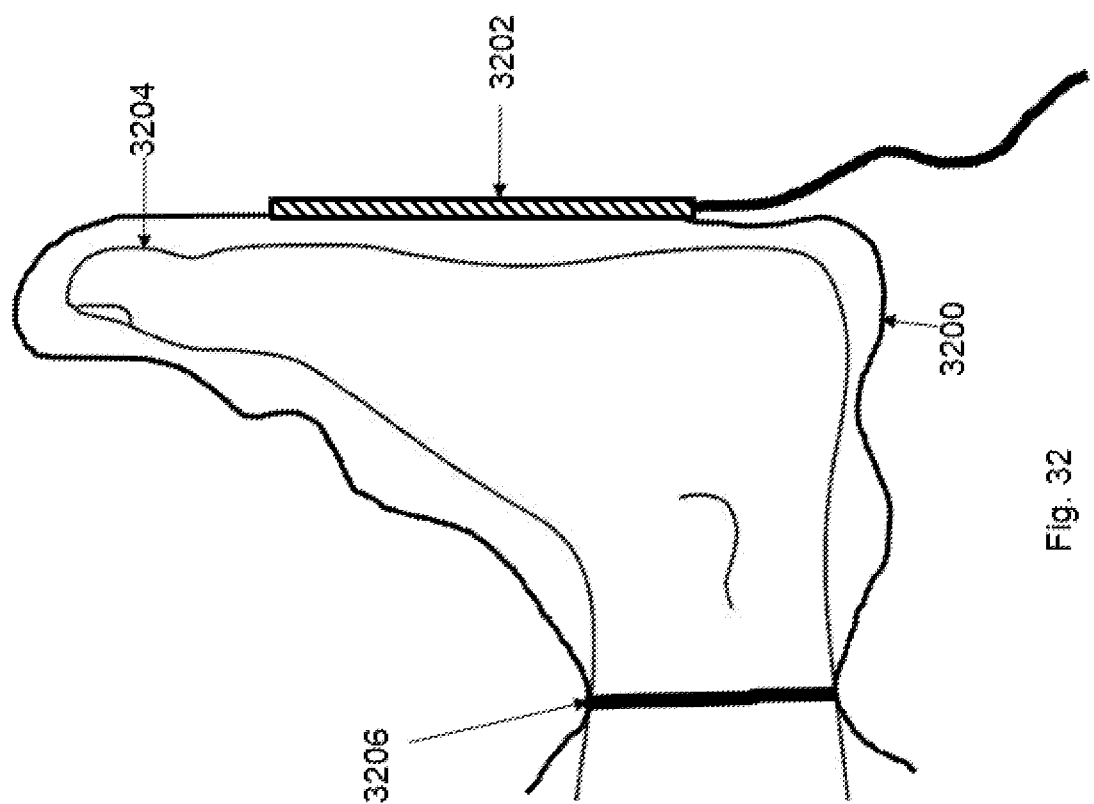
FIG. 32 shows a plasma applicator fastened to a bag.

FIG. 32 shows a plasma applicator 3202 fastened to a bag 3200. The plasma applicator is affixed to the bag 3200 and the bag 3200 surrounds a foot to be treated and thus forms a connected gas space 3204. The bag 3200 is made of a thin film and affixed above the ankle by means of a rubber band or strap 3206.

Figure 33:
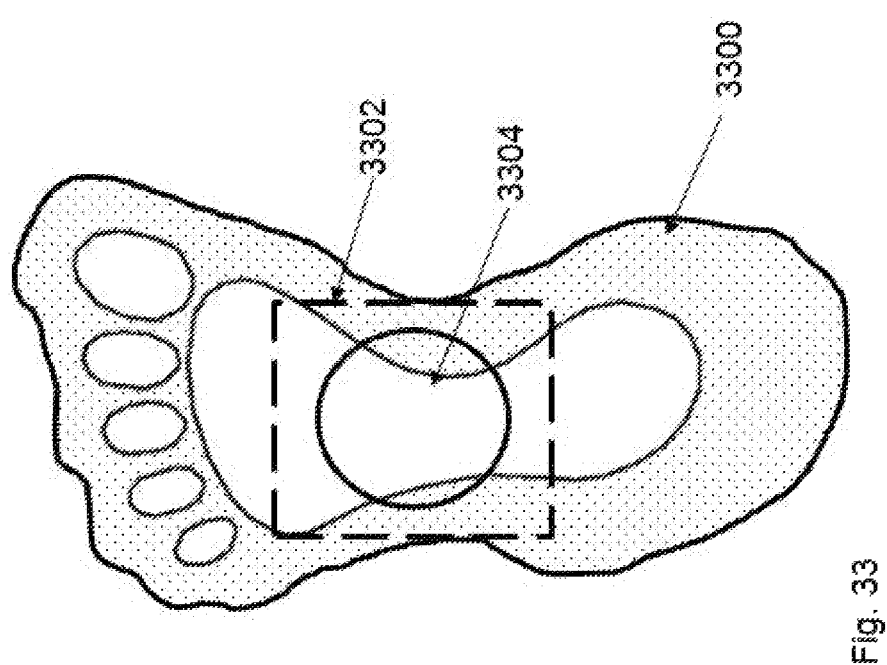
FIG. 33 shows a plasma applicator fastened to a bag, wherein the plasma applicator is arranged above a hole in the bag.

FIG. 33 shows a plasma applicator 3302 fastened to a bag 3300. The plasma applicator 3302 is only illustrated as a contour so that the bag 3300 visibly has a hole 3304, above which the plasma applicator 3302 is fastened. During use, an ignited plasma can enter the bag 3300 through the hole 3304 and can interact with the surface to be treated, the foot in this case. Consequently, this facilitates a large-area treatment of, e.g., a foot or at least a foot lower side.

LIST OF REFERENCE SIGNS

1 Apparatus for generating a cold atmospheric pressure plasma
2 Multilayer system
3 The side facing the surfaces to be treated
4 The side facing away from the surface to be treated
10 First electrode structure
10' Second electrode structure
11 First insulating structure
12 First electrode structure
13 Dielectric layer
14 Second electrode structure 15 Second insulating structure
16 Spacer structure
17 Third insulating structure
20 Insulating structure
30 Treatment region
40 Adhesion layer
45 Enclosure
50 Electrotechnical core
60 Insertion apparatus
61 Silicone spout
63 Taper
64 Latching apparatus
65 Connector with an electromagnetically compatible shield
66 Sealing plug
67 Inductors
68 Housing of the insertion apparatus
69 Interior of the insertion apparatus
70 Plug-in apparatus
71 High-voltage connector (HV connector)
72 Ground connector (GND connector)
75 Reinforcement
76 Bore with latching function
77 Contact at the plug-in apparatus
78 Clamping contact
79 Conductor track
79' Second conductor track
80 Cable
81 Kink protection
100 Plasma applicator
110 Power supply unit
110' Integrated power supply unit
110" Mobile power supply unit
112 Contact
114 Two separate contacts
120' Integrated power supply unit
120" Integrated power supply unit
122 Spacer structure
122' Spacer structure
130 Insertion slot
140 Receiver coil arrangement
150 Transmitter coil arrangement
160 Inductive charging apparatus
200 Spacer structure
210 Honeycomb
220 Plasma
230 Electrode structure
240 Counter electrode
300 Closed circuit
300', 300" Other closed circuits
310 Connection points
910 Wound cover
1900 Plasma applicator
1902 Electrotechnical core
1904 Side of an electrotechnical core
1906 First insulation layer
1908 First electrode structure
1910 Second insulation layer
1912 Second electrode structure
1914 Third insulation layer
1916 Third electrode structure
1918 Enclosure
2000 Electrotechnical core
2002 Second electrode structure
2004 First electrode structure
2006 Second insulation layer
2008, 2010 Conductor track
2100 Electrotechnical core
2102 Third insulation layer
2104 Tab
2106 End of a conductor track
2108 Contact face
2200 Electrotechnical core
2202 Third electrode structure
2204 Side of an electrotechnical core
2206 Tab-shaped conductor track
2208 Region
2210 Region
2212 Third insulation layer
2214 End of a tab
2216 Contact area of a conductor track
2300 Electrotechnical core
2302 Third electrode structure
2304 Tab-shaped conductor track
2306 Chip card-shaped reinforcement
2308 Region
2310 Region
2314 Contact face
2316 End of a tab-shaped conductor track
2318 Contact area of a conductor track
2400 Plug-in apparatus
2402 Insertion apparatus
2404 Connector for transmitting a voltage signal
2406, 2408 Further connectors
2500 Plasma applicator
2502 Electrotechnical core
2504 Enclosure
2506 Access port
2507 Side facing a surface to be treated
2508 A first insulation layer
2510 First electrode structure
2512 Second insulation layer
2514 Second electrode structure
2516 Third insulation layer
2518 Third electrode structure
2522 Gas space
2524 Female socket
2526 Integrated valve
2600 Plug-in apparatus
2602 Insertion apparatus
2604 Access port
2606 Tube
2608 Socket
2610 Valve
2700 Plug-in apparatus
2702 Insertion apparatus
2704 Access port
2706 Tube
2708 Socket
2710 Valve
2800 Plasma applicator
2802 Enclosure
2804 Electrotechnical core
2806 Plug-in apparatus
2808 Access port
2810 Gas space
2900 Plasma applicator
2902 Enclosure
2904 Electrotechnical core
2908 Adhesion layer
2912 First sensor
2914 Second sensor
2916 Data processing device
2918 Data signal
2920 Data signal B1 Width of the insertion apparatus
B2 Width of the plug-in apparatus
B3 Width of the plug-in apparatus
H1 Height of the insertion apparatus
H2 Height of the plug-in apparatus
K1 Minimum creepage distance
L1 Minimum length of the creepage distance on the patient side
L2 Length of the plugged together system
L3 Length of the plug-in apparatus outside of the insertion apparatus
L4 Length of the plug-in apparatus
L5 Overall length of the plug-in apparatus

The invention claimed is:

1. A power supply unit and a plasma applicator comprising an electrotechnical core for generating a cold atmospheric pressure or low-pressure plasma for the treatment of human and/or animal and/or technical surfaces, wherein the electrotechnical core has a side facing the surface to be treated and a side facing away from the surface to be treated and comprises the following layers, arranged above one another, starting from the side facing the surface to be treated:— a first insulation layer,— a first electrode structure which is provided with a first contact for establishing electrical contact between the first electrode structure and a power supply unit and which is grounded during operation,— a second insulation layer, which is embodied to galvanically isolate the first electrode structure and a second electrode structure from one another,— wherein the second electrode structure which is provided with a second contact for establishing electrical contact between the second electrode structure and a power supply unit and which is driven during operation by a voltage signal that is supplied by a power supply unit and that is sufficient to ignite a plasma,— a third insulation layer, which is embodied to galvanically isolate the second electrode structure and a third electrode structure from one another,— wherein the third electrode structure which is provided with a third contact in order to ground the third electrode structure during operation; the plasma applicator comprising means for ensuring single use of the plasma applicator, wherein the plasma applicator comprises a memory that is configured to store a special code or hash value, and wherein the power supply unit is configured to check whether a plasma applicator has already been used or whether it the plasma applicator is suitable for a certain plasma treatment.

2. The power supply unit and the plasma applicator as claimed in claim 1, comprising a plug-in apparatus, wherein the first and second contact accordingly form a first and second conductor track of the plug-in apparatus, which each protrude at the same longitudinal side of the electrotechnical core from the longitudinal side of the respective corresponding electrode structure, and wherein the plug-in apparatus further comprises an insulating tab, which is accordingly connected to the second insulation layer, wherein the first and the second conductor track are galvanically isolated from one another by the insulating tab.

3. The power supply unit and the plasma applicator as claimed in claim 2, wherein the means for ensuring single use comprises an RFID transponder that is integrated in the plasma applicator and configured to provide an information which prevents the release of a high voltage by a power supply unit.

4. The power supply unit and the plasma applicator comprising an electrotechnical core as claimed in claim 1, wherein the plasma applicator furthermore comprises an enclosure with a pocket which is embodied such that an electrotechnical core can be inserted into the pocket and then be at least partly enclosed by the enclosure.

5. The power supply unit and the plasma applicator as claimed in claim 4, wherein the enclosure is formed by a biocompatible material, including medical silicone, a lacquer, an adhesive, a film, a textile, a compression textile or organic material such as gauze, cellulose or cotton.

6. The power supply unit and the plasma applicator as claimed in claim 4, wherein the enclosure comprises at least one layer with liquid-absorbing and/or liquid-removing and/or liquid-distributing materials.

7. The power supply unit and the plasma applicator as claimed in claim 4, wherein the enclosure comprises insertion slots which are arranged on the side of the plasma applicator facing away from the surface to be treated and which are embodied such that a power supply unit or an insertion apparatus, complementary to the insertion slots, can be inserted into the insertion slots in order then to be electrically connected to the contacts of the electrotechnical core.

8. The power supply unit and the plasma applicator as claimed in claim 1, wherein the plasma applicator comprises an access port, which is arranged and embodied in such a way that, during a plasma treatment, a fluid medium can be supplied to or removed from a sealed gas space formed by the enclosure between the electrotechnical core and a surface to be treated.

9. The power supply unit and the plasma applicator as claimed in claim 1, wherein the plasma applicator comprises a barbed hook-occupied part of a hook-and-loop closure on a side of the plasma applicator facing a surface to be treated.

10. The power supply unit and the plasma applicator as claimed in claim 4, wherein the plasma applicator comprises an integrated power supply unit comprising a power store electrically connected to the contacts of the electrotechnical core in order to transmit a voltage signal sufficient to ignite a plasma to at least one of the electrode structures during operation.

11. The power supply unit and the plasma applicator as claimed in claim 10, wherein the integrated power supply unit comprises an electrical circuit which is embodied to convert a voltage provided by the energy store into a voltage signal sufficient to ignite a plasma and to transmit said voltage signal to the contact of at least one of the electrode structures.

12. The power supply unit and the plasma applicator as claimed in claim 11, wherein the plasma applicator comprises a power receiving apparatus electrically connected to at least the contact of the second electrode structure, said power receiving apparatus respectively containing one or more receiver coil arrangements, and wherein electrical energy can be transferred from a transmitter coil arrangement of a power dispensing apparatus to the receiver coil arrangements in the plasma applicator by means of electromagnetic induction.

13. The power supply unit and the plasma applicator as claimed in claim 1, wherein the electrotechnical core furthermore comprises a spacer structure which is arranged adjacent to the first insulation layer on the side of the electrotechnical core facing the surface to be treated such that the spacer structure is situated between a surface to be treated and the first insulation layer during a plasma treatment.

14. The power supply unit and the plasma applicator as claimed in claim 10, wherein the plasma applicator comprises a power receiving apparatus electrically connected to at least the contact of the second electrode structure, said power receiving apparatus respectively containing one or more receiver coil arrangements, and wherein electrical energy can be transferred from a transmitter coil arrangement of a power dispensing apparatus to the receiver coil arrangements in the plasma applicator by means of electromagnetic induction.

* * * * *